(12) United States Patent
Brooks et al.

(10) Patent No.: US 7,732,461 B2
(45) Date of Patent: Jun. 8, 2010

(54) TRYCLIC NITROGEN CONTAINING COMPOUNDS AND THEIR USE AS ANTIBACTERIALS

(75) Inventors: Gerald Brooks, Harlow (GB); Ilaria Giordano, Harlow (GB); Alan Joseph Hennessy, Harlow (GB); Neil David Pearson, Harlow (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 12/298,326

(22) PCT Filed: Apr. 25, 2007

(86) PCT No.: PCT/EP2007/054079

§ 371 (c)(1),
(2), (4) Date: Oct. 24, 2008

(87) PCT Pub. No.: WO2007/122258

PCT Pub. Date: Nov. 1, 2007

(65) Prior Publication Data

US 2009/0137568 A1    May 28, 2009

(30) Foreign Application Priority Data

Apr. 26, 2006  (GB) ................. 0608263.0

(51) Int. Cl.
*C07D 471/16*    (2006.01)
*A61K 31/4375*  (2006.01)

(52) U.S. Cl. ....................... 514/292; 546/86

(58) Field of Classification Search ........... 546/86; 514/292

See application file for complete search history.

(56) References Cited

U.S. PATENT DOCUMENTS

| 2008/0221110 A1 | 9/2008 | Cailleau et al. |
| 2009/0062265 A1 | 3/2009 | Jones et al. |
| 2009/0137568 A1 | 5/2009 | Brooks et al. |

FOREIGN PATENT DOCUMENTS

| WO | WO 02/056882 | 7/2002 |
| WO | WO 02/096907 | 12/2002 |
| WO | WO 03/064431 | 8/2003 |
| WO | WO 2007/071936 | 6/2007 |
| WO | WO2008/003690 | 1/2008 |
| WO | WO2008/116815 | 10/2008 |
| WO | WO2008/125594 | 10/2008 |
| WO | WO2008/128942 | 10/2008 |
| WO | WO2008/128953 | 10/2008 |
| WO | WO2008/128962 | 10/2008 |

OTHER PUBLICATIONS

Snyder et al., PubMed Abstract (J. Med. Liban 48(4): 208-214,Jul.-Aug. 2000.*
Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*

* cited by examiner

*Primary Examiner*—Kahsay T Habte
(74) *Attorney, Agent, or Firm*—Reid S. Willis; John Lemanowicz

(57) ABSTRACT

Tricyclic nitrogen containing compounds of formula (I) and their use as antibacterials.

15 Claims, No Drawings

TRYCLIC NITROGEN CONTAINING COMPOUNDS AND THEIR USE AS ANTIBACTERIALS

This application is a 371 of International Application No. PCT/EP2007/054079 filed 25 Apr. 2007, and claims the priority of GB 0608263.0 filed 26 Apr. 2006, which applications are incorporated herein in their entirety.

This invention relates to novel compounds, compositions containing them and their use as antibacterials.

WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO06002047, WO06014580, WO06010040, WO06017326, WO06012396, WO06017468, WO06020561, WO01/25227, WO02/40474, WO02/07572, WO2004035569, WO2004089947, WO04024712, WO04024713, WO04087647, WO2005016916, WO2005097781, WO06010831, WO04035569, WO04089947, WO06021448, WO06032466 and WO06038172 disclose quinoline, naphthyridine, morpholine, cyclohexane, piperidine and piperazine derivatives having antibacterial activity. WO2004104000 discloses tricyclic condensed ring compounds capable of selectively acting on cannabinoid receptors.

This invention provides a compound of formula (I) or a pharmaceutically acceptable salt, solvate or N-oxide thereof:

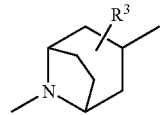

wherein:

$R^{1a}$ and $R^{1b}$ are independently selected from hydrogen; halogen; cyano; $(C_{1-6})$alkyl; $(C_{1-6})$alkylthio; trifluoromethyl; trifluoromethoxy; carboxy; hydroxy optionally substituted with $(C_{1-6})$alkyl or $(C_{1-6})$alkoxy-substituted$(C_{1-6})$alkyl; $(C_{1-6})$alkoxy-substituted$(C_{1-6})$alkyl; hydroxy$(C_{1-6})$alkyl; an amino group optionally N-substituted by one or two $(C_{1-6})$alkyl, formyl, $(C_{1-6})$alkylcarbonyl or $(C_{1-6})$alkylsulphonyl groups; or aminocarbonyl wherein the amino group is optionally substituted by $(C_{1-4})$alkyl;

$R^2$ is hydrogen, or $(C_{1-4})$alkyl, or together with $R^6$ forms Y as defined below;

A is a group (i):

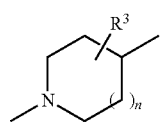

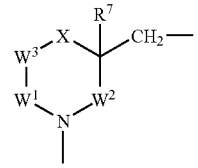

in which: $R^3$ is as defined for $R^{1a}$ or $R^{1b}$ or is oxo and n is 1 or 2:

or A is a group (ii)

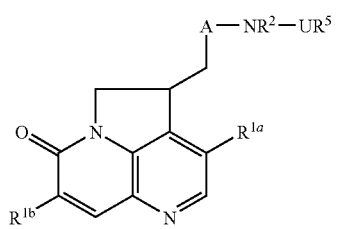

$W^1$, $W^2$ and $W^3$ are $CR^4R^8$
or $W^2$ and $W^3$ are $CR^4R^8$ and $W^1$ represents a bond between $W^3$ and N.
X is O, $CR^4R^8$, or $NR^6$;
one $R^4$ is as defined for $R^{1a}$ and $R^{1b}$ and the remainder and $R^8$ are hydrogen or one $R^4$ and $R^8$ are together oxo and the remainder are hydrogen;
$R^6$ is hydrogen or $(C_{1-6})$alkyl; or together with $R^2$ forms Y;
$R^7$ is hydrogen; halogen; hydroxy optionally substituted with $(C_{1-6})$alkyl; or $(C_{1-6})$alkyl;
Y is $CR^4R^8CH_2$; $CH_2CR^4R^8$; (C=O); $CR^4R^8$; $CR^4R^8$(C=O); or (C=O)$CR^4R^8$;
or when X is $CR^4R^8$, $R^8$ and $R^7$ together represent a bond;

U is selected from CO, and $CH_2$ and $R^5$ is an optionally substituted bicyclic carbocyclic or heterocyclic ring system (B):

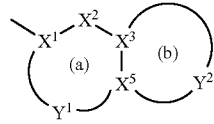

containing up to four heteroatoms in each ring in which
at least one of rings (a) and (b) is aromatic;
$X^1$ is C or N when part of an aromatic ring, or $CR^{14}$ when part of a non-aromatic ring;
$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;
$X^3$ and $X^5$ are independently N or C;
$Y^1$ is a 0 to 4 atom linker group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring;
$Y^2$ is a 2 to 6 atom linker group, each atom of $Y^2$ being independently selected from N, $NR^{13}$, O, $S(O)_x$, CO, $CR^{14}$ when part of an aromatic or non-aromatic ring or may additionally be $CR^{14}R^{15}$ when part of a non aromatic ring;

each of $R^{14}$ and $R^{15}$ is independently selected from: H; $(C_{1-4})$alkylthio; halo; carboxy$(C_{1-4})$alkyl; $(C_{1-4})$alkyl; $(C_{1-4})$alkoxycarbonyl; $(C_{1-4})$alkylcarbonyl; $(C_{1-4})$alkoxy$(C_{1-4})$alkyl; hydroxy; hydroxy$(C_{1-4})$alkyl; $(C_{1-14})$alkoxy; nitro; cyano; carboxy; amino or aminocarbonyl optionally mono- or di-substituted by $(C_{1-14})$alkyl; or $R^{14}$ and $R^{15}$ may together represent oxo;

each $R^{13}$ is independently H; trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; $(C_{1-4})$alkoxycarbonyl; $(C_{1-4})$alkylcarbonyl; $(C_{1-6})$alkylsulphonyl; aminocarbonyl wherein the amino group is optionally mono or disubstituted by $(C_{1-4})$alkyl;

each x is independently 0, 1 or 2.

This invention also provides a method of treatment of bacterial infections in mammals, particularly in man, which method comprises the administration to a mammal in need of such treatment an effective amount of a compound of formula (I), or a pharmaceutically acceptable salt, solvate or N-oxide thereof.

The invention also provides the use of a compound of formula (I), or a pharmaceutically acceptable salt, solvate or N-oxide thereof, in the manufacture of a medicament for use in the treatment of bacterial infections in mammals.

The invention also provides a pharmaceutical composition comprising a compound of formula (I), or a pharmaceutically acceptable salt, solvate or N-oxide thereof, and a pharmaceutically acceptable carrier.

In a particular aspect each $R^{1a}$ and $R^{1b}$ is independently hydrogen, $(C_{1-4})$alkoxy, $(C_{1-4})$alkylthio, $(C_{1-4})$alkyl, carboxy, hydroxymethyl or halogen; more particularly hydrogen, methoxy, methyl, cyano, or halogen.

In certain embodiments each $R^{1a}$ and $R^{1b}$ is hydrogen, methoxy, methyl, or halogen, such as chloro or fluoro. In some embodiments only one group $R^{1a}$ or $R^{1b}$ is other than hydrogen, such as $R^{1a}$ chloro or fluoro.

In a particular aspect $R^2$ is hydrogen.

Particular examples of $R^3$ include hydrogen; optionally substituted hydroxy; optionally substituted amino; halogen; $(C_{1-4})$ alkyl; 1-hydroxy-$(C_{1-4})$ alkyl; optionally substituted aminocarbonyl. More particular $R^3$ groups are hydrogen; $CONH_2$; 1-hydroxyalkyl e.g. $CH_2OH$; optionally substituted hydroxy e.g. methoxy; optionally substituted amino; and halogen, in particular fluoro. Most particularly $R^3$ is hydrogen, hydroxy, methoxy or fluoro.

In a particular aspect, when A is (ia), n is 1. In a further aspect $R^3$ is in the 3- or 4-position. In a more particular aspect, A is (ia), n is 1 and $R^3$ is in the 3-position, and more particularly is cis to the $NR^2$ group.

In particular embodiments, A is a group (ia) in which n is 1 and $R^3$ is hydrogen or hydroxy. More particularly, when A is 3-hydroxy-piperidin-4-ylamino the configuration is (3R,4S).

In a particular aspect, when A is (ii), X is $CR^4R^8$, $R^8$ is H and $R^4$ is H or OH, more particularly OH is trans to $R^7$. In a further aspect $W^1$ is a bond. In another aspect $R^7$ is H. In an additional aspect $W^1$ is a bond, $W^2$ and $W^3$ are both $CH_2$ and $R^7$ is H. Where A is 3-hydroxypyrrolidin-4-ylmethyl, in a particular aspect the configuration is (3S,4S).

In certain embodiments U is $CH_2$.

In certain embodiments $R^5$ is an aromatic heterocyclic ring (B) having 8-11 ring atoms including 2-4 heteroatoms of which at least one is N or $NR^{13}$ in which, in particular embodiments, $Y^2$ contains 2-3 heteroatoms, one of which is S and 1-2 are N, with one N bonded to $X^3$.

In alternative embodiments the heterocyclic ring (B) has ring (a) aromatic selected from optionally substituted benzo and pyrido and pyridazino and ring (b) non aromatic and $Y^2$ has 3-5 atoms, more particularly 4 atoms, including at least one heteroatom, with O, S, $CH_2$ or $NR^{13}$ bonded to $X^5$ where $R^{13}$ is other than hydrogen, and either NHCO bonded via N to $X^3$, or O, S, $CH_2$ or NH bonded to $X^3$. In a particular aspect the ring (a) contains aromatic nitrogen, and more particularly ring (a) is pyridine or pyridazine. Examples of rings (B) include optionally substituted:

(a) and (b) Aromatic 1H-pyrrolo[2,3-b]-pyridin-2-yl, 1H-pyrrolo[3,2-b]-pyridin-2-yl, 3H-imidazo[4,5-b]-pyrid-2-yl, 3H-quinazolin-4-one-2-yl, benzimidazol-2-yl, benzo[1,2,3]-thiadiazol-5-yl, benzo[1,2,5]-oxadiazol-5-yl, benzofur-2-yl, benzothiazol-2-yl, benzo[b]thiophen-2-yl, benzoxazol-2-yl, chromen-4-one-3-yl, imidazo[1,2-a]pyridin-2-yl, imidazo-[1,2-a]-pyrimidin-2-yl, indol-2-yl, indol-6-yl, isoquinolin-3-yl, [1,8]-naphthyridine-3-yl, oxazolo[4,5-b]-pyridin-2-yl, quinolin-2-yl, quinolin-3-yl, quinoxalin-2-yl, naphthalen-2-yl, 1,3-dioxo-isoindol-2-yl, benzothiophen-2-yl, 1H-benzotriazol-5-yl, 1H-indol-5-yl, 3H-benzooxazol-2-one-6-yl, 3H-benzooxazol-2-thione-6-yl, 3H-benzothiazol-2-one-5-yl, 3H-quinazolin-4-one-6-yl, benzo[1,2,3]thiadiazol-6-yl, benzo[1,2,5]thiadiazol-5-yl, benzo[1,4]oxazin-2-one-3-yl, benzothiazol-5-yl, benzothiazol-6-yl, cinnolin-3-yl, imidazo[1,2-a]pyridazin-2-yl, imidazo[1,2-b]pyridazin-2-yl, pyrazolo[1,5-a]pyrazin-2-yl, pyrazolo[1,5-a]pyridin-2-yl, pyrazolo[1,5-a]pyrimidin-6-yl, pyrazolo[5,1-c][1,2,4]triazin-3-yl, pyrido[1,2-a]pyrimidin-4-one-2-yl, pyrido[1,2-a]pyrimidin-4-one-3-yl, quinazolin-2-yl, quinoxalin-6-yl, thiazolo[3,2-a]pyrimidin-5-one-7-yl, thiazolo[5,4-b]pyridin-2-yl, thieno[3,2-b]pyridin-6-yl, thiazolo[5,4-b]pyridin-6-yl, thiazolo[4,5-b]pyridin-5-yl, [1,2,3]thiadiazolo[5,4-b]pyridin-6-yl, 2H-isoquinolin-1-one-3-yl (a) is Non Aromatic (2S)-2,3-dihydro-1H-indol-2-yl, (2S)-2,3-dihydro-benzo[1,4]dioxine-2-yl, 3-(R,S)-3,4-dihydro-2H-benzo[1,4]thiazin-3-yl, 3-(R)-2,3-dihydro-[1,4]dioxino[2,3-b]pyridin-3-yl, 3-(S)-2,3-dihydro-[1,4]dioxino[2,3-b]pyridin-3-yl, 2,3-dihydro-benzo[1,4]dioxan-2-yl, 3-substituted-3H-quinazolin-4-one-2-yl, (b) is Non Aromatic 1,1,3-trioxo-1,2,3,4-tetrahydrol $1^6$-benzo[1,4]thiazin-6-yl, benzo[1,3]dioxol-5-yl, 2,3-dihydro-benzo[1,4]dioxin-6-yl, 2-oxo-2,3-dihydro-benzooxazol-6-yl, 3-substituted-3H-benzooxazol-2-one-6-yl, 3-substituted-3H-benzooxazole-2-thione-6-yl, 3-substituted-3H-benzothiazol-2-one-6-yl, 4H-benzo[1,4]oxazin-3-one-6-yl (3-oxo-3,4-dihydro-2H-benzo[1,4]oxazin-6-yl), 4H-benzo[1,4]thiazin-3-one-6-yl (3-oxo-3,4-dihydro-2H-benzo[1,4]thiazin-6-yl), 4H-benzo[1,4]oxazin-3-one-7-yl, 4-oxo-2,3,4,5-tetrahydro-benzo[b][1,4]thiazepine-7-yl, 5-oxo-2,3-dihydro-5H-thiazolo[3,2-a]pyrimidin-6-yl, 1H-pyrido[2,3-b][1,4]thiazin-2-one-7-yl (2-oxo-2,3-dihydro-1H-pyrido[2,3-b]thiazin-7-yl), 2,3-dihydro-1H-pyrido[2,3-b][1,4]thiazin-7-yl, 2-oxo-2,3-dihydro-1H-pyrido[3,4-b]thiazin-7-yl, 2,3-dihydro-[1,4]dioxino[2,3-b]pyridin-6-yl, 2,3-dihydro-[1,4]dioxino[2,3-c]pyridin-7-yl, 2,3-dihydro-[1,4]dioxino[2,3-b]pyridin-7-yl, 3,4-dihydro-2H-benzo[1,4]oxazin-6-yl, 3,4-dihydro-2H-benzo[1,4]thiazin-6-yl, 3-oxo-3,4-dihydro-2H-pyrido[3,2-b][1,4]oxazin-6-yl, 3,4-dihydro-2H-pyrido[3,2-b][1,4]thiazin-6-yl, 3-oxo-3,4-dihydro-2H-pyrido[3,2-b][1,4]thiazin-6-yl, 3,4-dihydro-1H-quinolin-2-one-7-yl, 3,4-dihydro-1H-quinoxalin-2-one-7-yl, 6,7-dihydro-4H-pyrazolo[1,5-a]pyrimidin-5-one-2-yl, 5,6,7,8-tetrahydro-[1,8]naphthyridin-2-yl, 2-oxo-3,4-dihydro-1H-[1,8]naphthyridin-6-yl, 6-oxo-6,7-dihydro-5H-8-thia-1,2,5-triaza-naphthalen-3-yl, 2-oxo-2,3-dihydro- 1H-pyrido[3,4-b][1,4]oxazin-7-yl, 2-oxo-2,3-dihydro-1H-pyrido[2,3-b][1,4]oxazin-7-yl, 6,7-dihydro-[1,4]dioxino[2,3-d]pyrimidin-2-yl, [1,3]oxathiolo[5,4-c]pyridin-6-yl, 3,4-dihydro-2H-pyrano[2,3-c]pyridine-6-yl, 2,3-dihydro[1,4]oxathiino[2,3-c]pyridine-7-yl, 2,3-dihydrofuro[2,3-c]pyridin-5-yl, 2,3-dihydro-1-benzofuran-5-yl, indan-2-yl, 5-oxo-1,2,3,5-tetrahydro-7-indolizinyl, 2-methyl-1-oxo-1,2,3,4-tetrahydro-7-isoquinolinyl, 5,6-dihydro-4H-cyclopenta[b]thien-2-yl, 6,7-dihydro-5H-thieno[3,2-b]pyran-2-yl, 6-oxo-6,7-dihydro-5H-pyridazino[3,4-b][1,4]thiazin-3-yl.

In some embodiments $R^{13}$ is H if in ring (a) or in addition $(C_{1-4})$alkyl such as methyl or isopropyl when in ring (b). More particularly, in ring (b) $R^{13}$ is H when $NR^{13}$ is bonded to $X^3$ and $(C_{1-4})$alkyl when $NR^{13}$ is bonded to $X^5$.

In further embodiments $R^{14}$ and $R^{15}$ are independently selected from hydrogen, halo, hydroxy, $(C_{1-4})$ alkyl, $(C_{1-4})$ alkoxy, nitro and cyano. More particularly $R^{15}$ is hydrogen.

More particularly each $R^{14}$ is selected from hydrogen, chloro, fluoro, hydroxy, methyl, methoxy, nitro and cyano. Still more particularly $R^{14}$ is selected from hydrogen, fluorine or nitro.

Most particularly $R^{14}$ and $R^{15}$ are each H.

Particular groups $R^5$ include:
[1,2,3]thiadiazolo[5,4-b]pyridin-6-yl
1H-pyrrolo[2,3-b]pyridin-2-yl
2,3-dihydro-[1,4]dioxino[2,3-b]pyridin-6-yl
2,3-dihydro-[1,4]dioxino[2,3-b]pyridin-7-yl
2,3-dihydro-[1,4]dioxino[2,3-c]pyridin-7-yl
2,3-dihydro-benzo[1,4]dioxin-6-yl
2-oxo-2,3-dihydro-1H-pyrido[2,3-b][1,4]oxazin-7-yl
2-oxo-2,3-dihydro-1H-pyrido[2,3-b][1,4]thiazin-7-yl
3,4-dihydro-2H-benzo[1,4]oxazin-6-yl
3-methyl-2-oxo-2,3-dihydro-benzooxazol-6-yl
3-oxo-3,4-dihydro-2H-benzo[1,4]oxazin-6-yl
3-oxo-3,4-dihydro-2H-pyrido[3,2-b][1,4]oxazin-6-yl
3-oxo-3,4-dihydro-2H-benzo[1,4]thiazin-6-yl (4H-benzo[1,4]thiazin-3-one-6-yl)
4-oxo-4H-pyrido[1,2-a]pyrimidin-2-yl
6-nitro-benzo[1,3]dioxol-5-yl
7-fluoro-3-oxo-3,4-dihydro-2H-benzo[1,4]oxazin-6-yl
8-hydroxy-1-oxo-1,2-dihydro-isoquinolin-3-yl
8-hydroxyquinolin-2-yl
benzo[1,2,3]thiadiazol-5-yl
benzo[1,2,5]thiadiazol-5-yl
benzothiazol-5-yl
thiazolo-[5,4-b]pyridin-6-yl
3-oxo-3,4-dihydro-2H-pyrido[3,2-b][1,4]thiazin-6-yl
7-chloro-3-oxo-3,4-dihydro-2H-pyrido[3,2-b][1,4]thiazin-6-yl
7-fluoro-3-oxo-3,4-dihydro-2H-pyrido[3,2-b][1,4]thiazin-6-yl
2-oxo-2,3-dihydro-1H-pyrido[3,4-b][1,4]thiazin-7-yl
[1,3]oxathiolo[5,4-c]pyridin-6-yl
3,4-dihydro-2H-pyrano[2,3-c]pyridine-6-yl
2,3-dihydro-1,4-benzodioxin-5-carbonitro-7-yl
2,3-dihydro[1,4]oxathiino[2,3-c]pyridin-7-yl
2,3-dihydrofuro[2,3-c]pyridin-5-yl
5-fluoro-2,3-dihydro-1,4-benzodioxino-7-yl
2,3-dihydro-1-benzofuran-5-yl
6,7-dihydro-5H-thieno[3,2-b]pyran-2-yl
6-oxo-6,7-dihydro-5H-pyridazino[3,4-b][1,4]thiazin-3-yl
5-oxo-1,2,3,5-tetrahydro-7-indolizinyl
2-methyl-oxo-1,2,3,4-tetrahydro-7-isoquinolinyl
8-fluoro-2,3-dihydro-1,4-benzodioxin-6-yl
2,3-dihydro-1-benzofuran-7-carbonitrile
5,6-dihydro-4H-cyclopenta[b]thien-2-yl
6,7-dihydro-5H-thieno[3,2-b]pyran-2-yl
especially
3-oxo-3,4-dihydro-2H-pyrido[3,2-b][1,4]oxazin-6-yl
3-oxo-3,4-dihydro-2H-pyrido[3,2-b][1,4]thiazin-6-yl
2,3-dihydro-[1,4]dioxino[2,3-c]pyridin-7-yl
[1,3]oxathiolo[5,4-c]pyridin-6-yl
3,4-dihydro-2H-pyrano[2,3-c]pyridine-6-yl
[1,2,3]thiadiazolo[5,4-b]pyridin-6-yl
2,3-dihydro-1,4-benzodioxin-5-carbonitro-7-yl
8-fluoro-2,3-dihydro-1,4-benzodioxin-6-yl
3-oxo-3,4-dihydro-2H-benzo[1,4]thiazin-6-yl
2,3-dihydro[1,4]oxathiino[2,3-c]pyridin-7-yl.

When used herein, the term "alkyl" includes groups having straight and branched chains, for instance, methyl, ethyl, n-propyl, iso-propyl, n-butyl, iso-butyl, sec-butyl, t-butyl, pentyl and hexyl. The term 'alkenyl' should be interpreted accordingly.

Halo or halogen includes fluoro, chloro, bromo and iodo. Haloalkyl moieties include 1-3 halogen atoms.

Compounds within the invention contain a heterocyclyl group and may occur in two or more tautomeric forms depending on the nature of the heterocyclyl group; all such tautomeric forms are included within the scope of the invention.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Furthermore, it will be understood that phrases such as "a compound of formula (I) or a pharmaceutically acceptable salt, solvate or N-oxide thereof" are intended to encompass the compound of formula (I), an N-oxide of formula (I), a pharmaceutically acceptable salt of the compound of formula (I), a solvate of formula (I), or any pharmaceutically acceptable combination of these. Thus by way of non-limiting example used here for illustrative purpose, "a compound of formula (I) or a pharmaceutically acceptable salt or solvate thereof" may include a pharmaceutically acceptable salt of a compound of formula (I) that is further present as a solvate.

Since the compounds of formula (I) are intended for use in pharmaceutical compositions it will readily be understood that in particular embodiments they are provided in substantially pure form, for example at least 60% pure, more suitably at least 75% pure and particularly at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and more particularly from 10 to 59% of a compound of the formula (I) or pharmaceutically acceptable salt, solvate or N-oxide thereof.

Particular compounds according to the invention include those mentioned in the examples and their pharmaceutically acceptable N-oxides, salts and solvates.

Pharmaceutically acceptable salts of the above-mentioned compounds of formula (I) include the acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. Compounds of formula (I) may also be prepared as the N-oxide. The invention extends to all such derivatives.

Certain of the compounds of formula (I) may exist in the form of optical isomers, e.g. diastereoisomers and mixtures of isomers in all ratios, e.g. racemic mixtures. The invention includes all such forms, in particular the pure isomeric forms. For example the invention includes enantiomers and diastereomers at the attachment points of $NR^2$ and/or $R^3$. The different isomeric forms may be separated or resolved one from the other by conventional methods, or any given isomer may be obtained by conventional synthetic methods or by stereospecific or asymmetric syntheses.

In a further aspect of the invention there is provided a process for preparing compounds of formula (I), and pharmaceutically acceptable salts, solvates and/or N-oxides thereof, which process comprises cyclising a compound of formula (II),

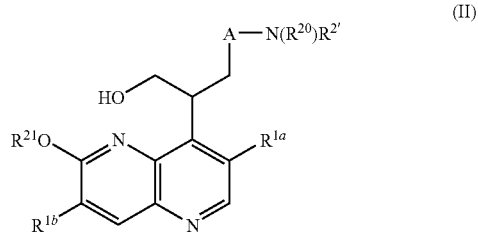

in which $R^{21}$ is $(C_{1-6})$alkyl, $R^{20}$ is $UR^5$ or a group convertible thereto and $R^{2'}$ is $R^2$ or a group convertible thereto, wherein A, $R^{1a}$, $R^{1b}$, $R^2$, U and $R^5$ are as defined in formula (I), and thereafter optionally or as necessary converting $R^{20}$ and $R^{2'}$ to $UR^5$ and $R^2$, interconverting any variable groups, and/or forming a pharmaceutically acceptable salt, solvate or N-oxide thereof.

The cyclisation reaction is effected by treatment of the compound of formula (II) with an activating agent such as methanesulphonyl chloride, p-toluenesulphonyl chloride, methanesulfonic anhydride or p-toluene sulfonic anhydride and an organic base such as triethylamine or diisopropylethylamine. Mesylate or tosylate preparation takes place under standard conditions and the cyclised compound, of formula (I) where $R^{2'}$ is $R^2$ and $R^{20}$ is $UR^5$ or of formula (IIA) where $R^{20}$ is a group convertible to $UR^5$ and $R^{2'}$ is a group convertible to $R^2$, forms in situ. Examples of $R^{21}$ include $(C_{1-4})$alkyl such as methyl.

Conveniently one of $R^{20}$ and $R^{2'}$ is an N-protecting group, such as such as t-butoxycarbonyl, benzyloxycarbonyl or 9-fluorenylmethyloxycarbonyl. This may be removed by several methods well known to those skilled in the art (for examples see "Protective Groups in Organic Synthesis, T. W. Greene and P. G. M. Wuts, Wiley-Interscience, 1999), for example conventional acid hydrolysis with, for example, trifluoroacetic acid or hydrochloric acid. The invention further provides compounds of formula (IIA) in which $R^{20}$ is hydrogen.

The free amine of formula (IIA) in which $R^{20}$ is hydrogen may be converted to $NR^2UR^5$ by conventional means such as amide formation with an acyl derivative $R^5COW$, for compounds where U is CO or, where U is $CH_2$, by alkylation with an alkyl halide $R^5CH_2$-halide in the presence of base, acylation/reduction with an acyl derivative $R^5COW$ or reductive alkylation with an aldehyde $R^5CHO$ under conventional conditions (see for examples Smith, M. B.; March, J. M. Advanced Organic Chemistry, Wiley-Interscience). The appropriate reagents containing the required $R^5$ group are known compounds or may be prepared analogously to known compounds, see for example WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144 and WO2004087145, WO2004/035569, WO2004/089947, WO2003082835, WO2002026723, WO06002047, WO06014580, WO06010040, WO06017326, WO06012396, WO06017468, WO06020561 and EP0559285.

Where $R^5$ contains an NH group, this may be protected with a suitable N-protecting group such as t-butoxycarbonyl, benzyloxycarbonyl or 9-fluorenylmethyloxycarbonyl during the coupling of the $R^5$ derivative with the free amine, The protecting group may be removed by conventional methods, such as by treatment with trifluoroacetic acid.

The compound of formula (II) may be prepared by the following Scheme 1:

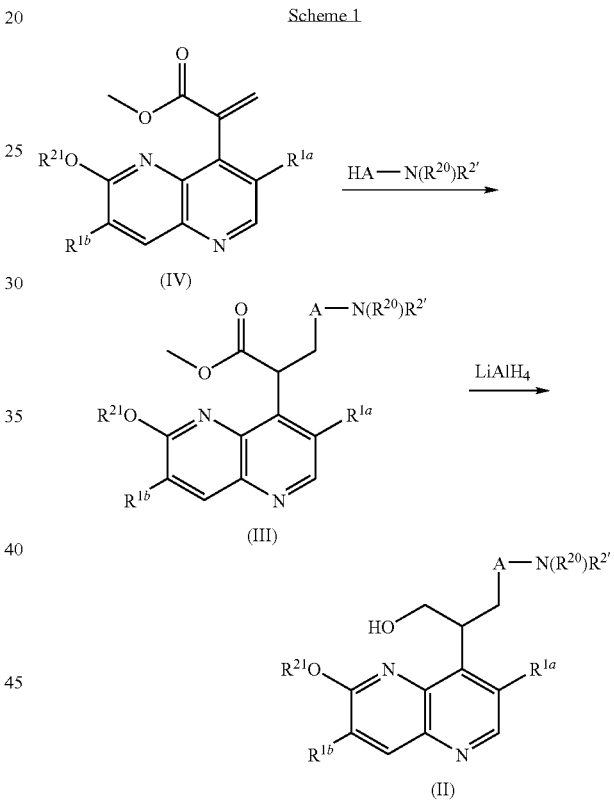

Compounds of general structure (III) may be prepared by reaction of acrylate ester (IV) with a compound $HA-N(R^{20})R^{2'}$, such as a Boc protected amino-piperidine, under conventional conditions for Michael additions (see for examples Smith, M. B.; March, J. M. Advanced Organic Chemistry, Wiley-Interscience). Reduction of (III) to (II) occurs upon treatment with lithium aluminium hydride under conventional conditions (see for examples Smith, M. B.; March, J. M. Advanced Organic Chemistry, Wiley-Interscience).

A route to intermediate (IV) is shown in Scheme 2. Acrylate (IV) may be prepared by reaction of triflate (V) where $R^{1a}$ is H or Cl with the known stannane (for synthesis of this stannane see Zhang, H. X.; Guibe, F.; Balavoine, G. J. Org. Chem. (1990), 55(6), 1857.) (VI) under typical Stille coupling conditions (for an example see Levin, Jeremy I. Tetrahedron Letters (1993), 34(39), 6211.

Scheme 2

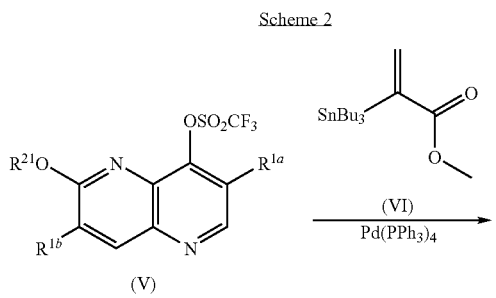

malonate with bromofluoro derivative (IX) (L=Br, $R^{1a}$=F) using Pd/Pt-Bu$_2$ gives (VIII) (for an example see Beare, Neil A.; Hartwig, John F. *J. Org. Chem.*, 2002, 67(2), 541). Also, the copper catalysed reaction of the sodium salt of dimethylmalonate with bromofluoro derivative (IX) (L=Br, $R^{1a}$=F) or bromochloro derivative (L=Br, $R^{1a}$=Cl) gives (VIII)(for an example see U.S. Pat. No. 6,156,925).

Diester (VIII) may be decarboxylated to give ester (VII) under standard conditions (for an example see Krapcho, A. Paul; Jahngen, E. G. E., Jr.; Lovey, A. J.; Short, Franklin W. *Tetrahedron Lett.*, 1974, (13), 1091) by heating a mixture of diester with LiCl in DMSO/water at 100° C. Conversion of (VII) to the acrylate (IV) may be effected by reaction with paraformaldehyde under basic conditions (for an example see Serelis, Algirdas K.; Simpson, Gregory W. *Tetrahedron Let.* 1997, 38(24), 4277.

Scheme 3

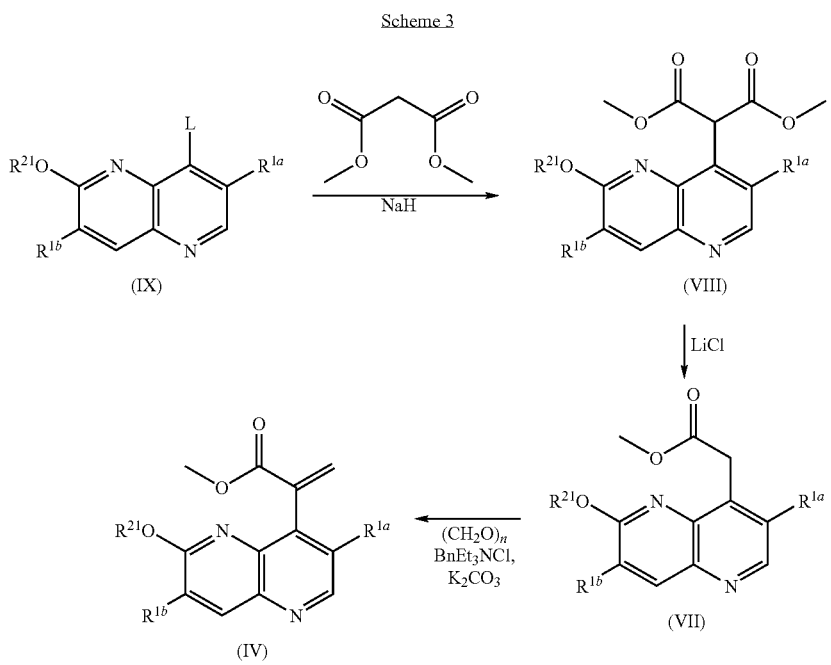

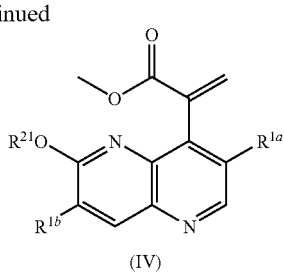

An alternative route to intermediate (IV), where $R^{1a}$ is H, Cl, F, cyano, ($C_{1-6}$)alkyl is shown in Scheme 3. L is a leaving group such as triflate or halogen e.g. bromine. For example, reaction of a chlorotriflate (TX) (L=triflate, $R^{1a}$=Cl) with the sodium salt of dimethylmalonate under basic conditions provides diester (VIII) under conventional conditions (see for an example Fellows, Ingrid M.; Kaelin, David E., Jr.; Martin, Stephen F. *J. Am. Chem. Soc.*, 2000, 122(44), 10781). The palladium catalysed reaction of the sodium salt of dimethyl- BnEt$_3$NCl=benzyltriethylammonium chloride Interconversions of $R^{1a}$, $R^{1b}$, $R^2$, A and $R^5$ are conventional, on compounds of formula (I) or earlier intermediates such as (IIA) in which $R^{20}$ is hydrogen. In compounds which contain an optionally protected hydroxy group, suitable conventional hydroxy protecting groups which may be removed without disrupting the remainder of the molecule include acyl and alkylsilyl groups. N-protecting groups are removed by conventional methods.

For example $R^{1a}$ or $R^{1b}$ methoxy is convertible to $R^{1a}$ or $R^{1b}$ hydroxy by treatment with lithium and diphenylphosphine (general method described in Ireland et al, *J. Amer. Chem. Soc.*, 1973, 7829) or HBr. Alkylation of the hydroxy group with a suitable alkyl derivative bearing a leaving group such as halide, yields $R^{1a}$ or $R^{1b}$ substituted alkoxy. $R^{1a}$ halogen is convertible to other $R^{1a}$ by conventional means, for example to hydroxy, alkylthiol (via thiol) and amino using metal catalysed coupling reactions, for example using copper as reviewed in Synlett (2003), 15, 2428-2439 and Angewandte Chemie, International Edition, 2003, 42(44), 5400-5449. $R^{1a}$ fluoro may be converted to methoxy by treatment with sodium methoxide in methanol. $R^{1b}$ halo such as bromo may be introduced by the general method of M. A. Alonso et al, Tetrahedron 2003, 59(16), 2821 or P. Imming et al, Eur. J. Med. Chem., 2001, 36(4), 375. $R^{1b}$ halo such as chloro may be introduced by treatment with N-chlorosuccinimide. $R^{1a}$ or $R^{1b}$ halo such as bromo may be converted to cyano by treatment with copper (I) cyanide in N,N-dimethylformamide. $R^{1a}$ or $R^{1b}$ carboxy may be obtained by conventional hydrolysis of $R^{1a}$ or $R^{1b}$ cyano, and the carboxy converted to hydroxymethyl by conventional reduction.

Compounds of formula HA-N($R^{20}$)$R^{2'}$ (V), and (IX) are known compounds or may be prepared analogously to known compounds, see for example WO2004/035569, WO2004/089947, WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO2003082835, WO2002026723, WO06002047 and WO06014580.

Further details for the preparation of compounds of formula (I) are found in the examples.

The antibacterial compounds according to the invention may be formulated for administration in any convenient way for use in human or veterinary medicine, by analogy with other antibacterials.

The pharmaceutical compositions of the invention include those in a form adapted for oral, topical or parenteral use and may be used for the treatment of bacterial infection in mammals including humans.

The composition may be formulated for administration by any route. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-1000 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 30 mg/kg per day.

The compound of formula (I) may be the sole therapeutic agent in the compositions of the invention or a combination with other antibacterials. If the other antibacterial is a β-lactam then a β-lactamase inhibitor may also be employed.

Compounds of formula (I) may be used in the treatment of bacterial infections caused by a wide range of organisms including both Gram-negative and Gram-positive organisms. Some compounds of formula (I) may be active against more than one organism. This may be determined by the methods described herein.

All publications, including but not limited to patents and patent applications, cited in this specification are herein incorporated by reference as if each individual publication were specifically and individually indicated to be incorporated by reference herein as though fully set forth.

The following examples illustrate the preparation of certain compounds of formula (I) and the activity of certain compounds of formula (I) against various bacterial organisms.

EXAMPLES AND EXPERIMENTAL

General

Abbreviations in the Examples:

RT=room temperature

ES=Electrospray mass spec.

LCMS=Liquid chromatography mass spec.

APCI+=Atmospheric pressure chemical ionisation mass spec

MDAP=mass directed preparative HPLCsurrey07

Certain reagents are also abbreviated herein. DME refers to dimethoxyethane, DMF refers to dimethylformamide, DMSO refers to dimethylsulfoxide, HATU refers to (0-(7-azabenzotriazol-1-yl)-N,N,N',N'-tetramethyl-uronium-hexafluorophosphate, TFA refers to trifluoroacetic acid, THF refers to tetrahydrofuran, TEA refers to triethylamine, Pd/C refers to palladium on carbon catalyst.

Proton nuclear magnetic resonance ($^1$H NMR) spectra were recorded at 400 or 250 MHz, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. CDCl$_3$ is deuteriochloroform, DMSO-d$_6$ is hexadeuteriodimethylsulfoxide, and CD$_3$OD is tetradeuteriomethanol. Mass spectra were obtained using electrospray (ES) ionization techniques. Elemental analyses were performed by Quantitative Technologies Inc., Whitehouse, N.J. All temperatures are reported in degrees Celsius. E. Merck Silica Gel 60 F-254 thin layer plates were used for thin layer chromatography. SCX is an ion exchange column containing strong cation exchange resin (benzene sulfonic acid) supplied by Varian, USA Chiralpak AD and AD-H columns comprise of silica for preparative columns (5 um particle size AD-H and 10 um particle size AD, 21 mm ID×250 mm L; 20 uM particle size AD, 101 mm ID×250 mm L) coated with Amylose tris(3,5-dimethylphenylcarbamate). Chiralpak AS-H column comprise of amylose tris[(S)-alpha-methylbenzylcarbamate) coated onto 5 um silica. Chiralpak IA column comprise of amylose tris(3,5-dimethylphenylcarbamate) immobilized onto 5 um silica. (Chiral Technologies USA). Measured retention times are dependent on the precise conditions of the chromatographic procedures. Where quoted below in the Examples they are indicative of the order of elution.

Celite® is a filter aid composed of acid-washed diatomaceous silica, and is a trademark of Manville Corp., Denver, Colo. Amberlyst®A21 is a weakly basic, macroreticular resin with alkyl amine functionality, ®Registered trademark of Rohm & Haas Co. MP-carbonate refers to macroporous triethylammonium methylpolystyrene carbonate (Argonaut Technologies).

Reactions involving metal hydrides including lithium hydride, lithium aluminium hydride, di-isobutylaluminium hydride, sodium hydride, sodium borohydride, sodium triacetoxyborohydride, (polystyrylmethyl)trimethylammonium cyanoborohydride are carried out under argon.

As will be understood by the skilled chemist, references to preparations carried out according to, in a similar manner to, by the general procedure of or method of other preparations, may encompass variations in routine parameters such as time, temperature, workup conditions, minor changes in reagent amounts etc.

Example 1

4-[(4-{[(3-Oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one Dihydrochloride

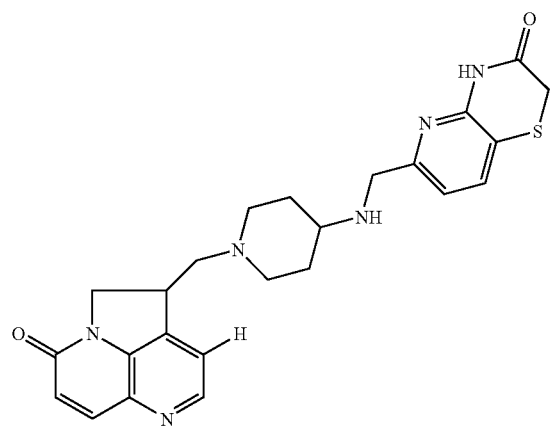

(a) Methyl 2-[6-(methyloxy)-1,5-naphthyridin-4-yl]-2-propenoate

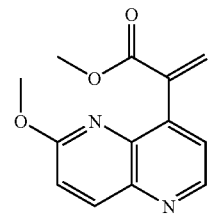

To a solution of 1,1,1-Trifluoro-methanesulfonic acid 6-methoxy-[1,5]naphthyridin-4-yl ester (for a synthesis see WO2003010138, Example 1(b))(5.936 g, 15.83 mmol) in DMF (10 ml) was added methyl 2-(tributylstannanyl)-2-propenoate (for a synthesis of this stannane see Zhang, H. X.; Guibe, F.; Balavoine, G. *J. Org. Chem.* (1990), 55(6), 1857.) (7.312 g, 23.74 mmol), Pd(PPh$_3$)$_4$ (1.83 g, 1.58 mmol), CuI (2.26 g, 11.87 mmol) and LiCl (673 mg, 15.83 mmol). The reaction was stirred for 1 h at 25° C. after which time the solvent was evaporated. The residue was chromatographed on silica eluting with a gradient of 10% ethyl acetate in hexane affording the desired compound as a brown solid (3.603 g, 93%).

MS (ES+) m/z 245 (MH$^+$, 100%)

(b) Methyl 3-[4-({[(1,1-dimethylethyl)oxy]carbonyl}amino)-1-piperidinyl]-2-[6-(methyloxy)-1,5-naphthyridin-4-yl]propanoate

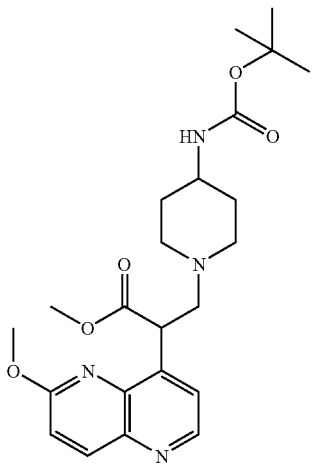

To a solution of methyl 2-[6-(methyloxy)-1,5-naphthyridin-4-yl]-2-propenoate (2.53 g, 10.37 mmol) in DMF (4 ml) and tetramethylguanidine (0.1 ml) was added 1,1-dimethylethyl 4-piperidinylcarbamate (2.08 g, 10.37 mmol). The reaction was stirred for 1 hour at 70° C. after which time the solvent was evaporated. The residue was chromatographed on silica eluting with a gradient of 5% methanol in dichloromethane affording the desired compound as a yellow solid (2.66 g, 58%).

MS (ES+) m/z 445 (MH+, 25%), 345 (100%).

(c) 1,1-dimethylethyl (1-{3-hydroxy-2-[6-(methyloxy)-1,5-naphthyridin-4-yl]propyl}-4-piperidinyl)carbamate

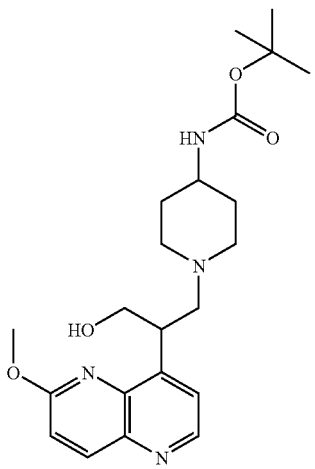

To a solution of methyl 3-[4-({[(1,1-dimethylethyl)oxy]carbonyl}amino)-1-piperidinyl]-2-[6-(methyloxy)-1,5-naphthyridin-4-yl]propanoate (1.70 g, 3.83 mmol) in tetrahydrofuran (40 ml) at −78° C. was added lithium aluminium hydride (1M in diethyl ether, 4.59 ml, 4.59 mmol). The reaction was then stirred at −78° C. for 0.5 h before water (10 ml), then 2M NaOH solution (10 ml) and finally water (10 ml) was added and the mixture warmed to ambient temperature and then filtered and evaporated. The residue was subjected to column chromatography on silica gel using a 0-5% methanol in dichloromethane gradient affording the desired compound as a white solid (601 mg, 38%).

MS (ES+) m/z 417 (MH+, 15%), 317 (100%).

(d) 1,1-dimethylethyl{1-[(7-oxo-4,5-dihydro-7H-pyrrolo[3,2,1-de]-1,5-naphthyridin-4-yl)methyl]-4-piperidinyl}carbamate

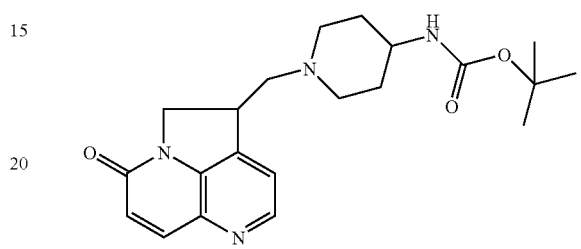

To a solution of 1,1-dimethylethyl (1-{3-hydroxy-2-[6-(methyloxy)-1,5-naphthyridin-4-yl]propyl}-4-piperidinyl)carbamate (501 mg, 1.20 mmol) in dichloromethane (5 ml) and triethylamine (200 µl, 1.45 mmol) at 0° C. was added methanesulfonyl chloride (112 µl, 1.145 mmol) and the mixture was warmed to ambient temperature. The reaction was stirred for 1 hour at 25° C. and then was treated with water (20 ml). The aqueous phase was separated and further extracted with 10% methanol in dichloromethane (2×100 ml). The combined organic layers were dried and the solvent was evaporated to give the crude mesylate which was used without further purification.

To a solution of crude mesylate in dichloromethane (5 ml) was added DBU and the reaction stirred at ambient temperature for 1 h. Chloroform (5 ml) was then added and the reaction heated at 50° C. for 1 h after which time the solvent was evaporated. The residue was subjected to column chromatography on silica gel using a 10% methanol in dichloromethane gradient. This provided the desired compound as a yellow solid (95 mg, 22%).

MS (ES+) m/z 385 (MH+, 25%), 285 (100%).

(e) 4-[(4-amino-1-piperidinyl)methyl]-4,5-dihydro-7H-pyrrolo[3,2,1-de]-1,5-naphthyridin-7-one To a solution of 1,1-dimethylethyl {1-[(7-oxo-4,5-dihydro-7H-pyrrolo[3,2,1-de]-1,5-naphthyridin-4-yl)methyl]-4-piperidinyl}carbamate (91 mg, 0.24 mmol) in chloroform (1 ml) was added HCl (4M in 1,4-dioxane) (2 ml) and the solution was stirred for 1 hour at 25° C. after which time the solvent was evaporated. The dihydrochloride salt of 4-[(4-amino-1-piperidinyl)methyl]-4,5-dihydro-7H-pyrrolo[3,2,1-de]-1,5-naphthyridin-7-one was used without further purification.

(f) Title Compound

To a solution of the dihydrochloride salt of 4-[(4-amino-1-piperidinyl)methyl]-4,5-dihydro-7H-pyrrolo[3,2,1-de]-1,5-naphthyridin-7-one (56 mg, 0.158 mmol) in methanol (0.4 ml), dichloromethane (1.6 ml) was added triethylamine (110 µl, 0.79 mmol) and 3-oxo-3,4-dihydro-2H-pyrido[3,2-b][1,4]thiazine-6-carboxaldehyde (for a synthesis see WO2003087098, Example 301(d)) (31 mg, 0.158 mmol). This mixture was stirred for 18 h at 25° C. before NaBH₄ (6 mg, 0.158 mmol) was added and the reaction stirred for a further 0.5 h after which time the solvent was evaporated and the residue was subjected to column chromatography on silica gel using a 0-30% methanol in dichloromethane gradient. This provided the free base of the title compound as a yellow solid (30 mg, 41%).

$^1$H NMR δ (d$_4$-MeOH) 1.25-1.35 (2H, m), 1.52-1.71 (2H, m), 1.98-2.25 (4H, m), 2.60-2.85 (2H, m), 2.95-3.25 (2H, m), 3.62 (2H, s), 3.51-4.16 (2H, m), 4.25 (1H, dd, J 13 and 9 Hz), 4.55 (1H, dd, J 13 and 4 Hz), 6.88 (1H, d J 9 Hz), 7.05 (1H, d, J 9 Hz), 7.58 (1H, d, J 8 Hz), 7.72 (1H, d, J 10 Hz), 7.99 (1H, d, J 30 Hz), 8.48 (1H, d, J 8 Hz).

MS (ES+) m/z 463 (MH⁺, 100%).

Treatment of the free base of the title compound with 4M HCl in 1,4-dioxane and subsequent evaporation to dryness gave the dihydrochloride salt.

Example 2

3-Chloro-4-({4-[(2,3-dihydro[1,4]dioxino[2,3-c]pyridin-7-ylmethyl)amino]-1-piperidinyl}methyl)-4,5-dihydro-7H-pyrrolo[3,2,1-de]-1,5-naphthyridin-7-one Hydrochloride

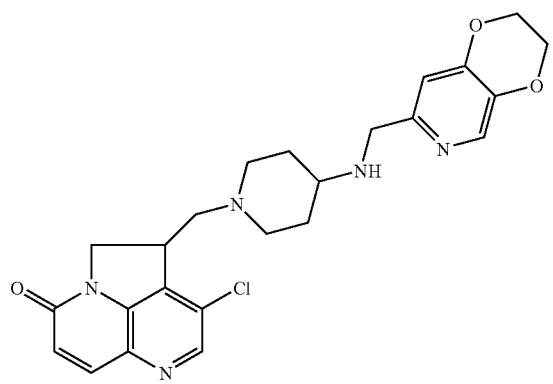

(a) Dimethyl[3-chloro-6-(methyloxy)-1,5-naphthyridin-4-yl]propanedioate

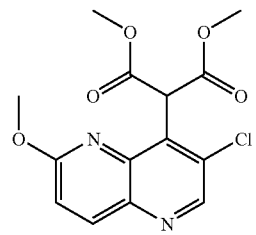

Method 1

To a solution of dimethylmalonate (82 ml, 715 mmol) in N,N-dimethylformamide (1400 ml) at 0° C. was added sodium hydride (60% dispersion in oil)(28.6 g, 715 mmol). The mixture was stirred for 0.5 h and sonicated for 0.5 h before adding 1,1,1-trifluoro-methanesulfonic acid 3-chloro-6-methoxy-[1,5]naphthyridin-4-yl ester (for a synthesis see WO2004058144, Example 1(b)) (88.88 g, containing some oil, estimated to contain 81.8 g, 238.5 mmol, of triflate). The reaction mixture was then heated at 50° C. for 12 h. The reaction was cooled, treated with ethyl acetate, water and HCl (2N) (340 ml). The organic phase was washed twice with water, the total aqueous re-extracted with ethyl acetate and this extract water-washed. The total organic phase was dried and the solvent was removed under reduced pressure. The residue was kept under high vacuum overnight, treated with toluene and stirred for 1 h. Filtration gave the desired compound. The toluene solution was subjected to column chromatography on silica gel using a hexane and ethyl acetate gradient to provide more of the desired compound; (total yield: 62.72 g, 81%).

MS (ES+) m/z 325 (MH⁺, 100%).

Method 2

(i) 8-bromo-7-chloro-2-(methyloxy)-1,5-naphthyridine

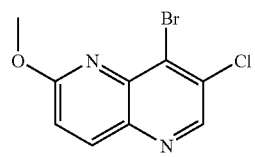

To a solution of 3-chloro-6-(methyloxy)-1,5-naphthyridin-4(1H)-one (3-chloro-6-(methyloxy)-1,5-naphthyridin-4-ol, for a synthesis see WO2004058144, Example 1(a) (5.1 g, 24.28 mmol) in DMF (50 ml) at 0° C. was added phosphorous tribromide dropwise (2.77 ml, 29.1 mmol) keeping the internal temperature below 20° C. The reaction mixture was then stirred at 10° C. for 0.5 h and then at 25° C. for 1 h. The mixture was then poured on 200 ml of water and the water basified to neutral pH with potassium carbonate. The solid formed was filtered off, washed with water and dried in the oven and then in the desiccator to afford the desired compound (5.8 g, 88%).

MS (ES+) m/z 274 (MH⁺, 100%).

(ii) Dimethyl[3-chloro-6-(methyloxy)-1,5-naphthyridin-4-yl]propanedioate

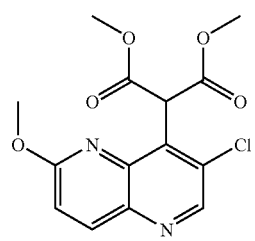

To a solution of dimethylmalonate (68.6 ml, 600 mmol) in 1,4-dioxane (600 ml) under Argon was added sodium hydride (60% dispersion in oil)(22 g, 550 mmol). The mixture was stirred at 75° C. for 2 h before adding 8-bromo-7-chloro-2-(methyloxy)-1,5-naphthyridine (54.5 g, 200 mmol) and copper(I) bromide (10 g, 69.7 mmol). The reaction mixture was then heated at 100° C. for 18 h. The reaction was cooled, treated with ethyl acetate, water and HCl (2N) (175 ml) and filtered through Celite. The aqueous phase (pH=3) was extracted with ethyl acetate. The organic phase was washed with water, dried and the solvent was removed under reduced pressure. The residue was subjected to column chromatography on silica gel using a hexane and ethyl acetate gradient (15%-25% ethyl acetate/hexane) to provide the desired compound (63 g, 97%).

MS (ES+) m/z 325 (MH+, 100%).

(b) Methyl[3-chloro-6-(methyloxy)-1,5-naphthyridin-4-yl]acetate

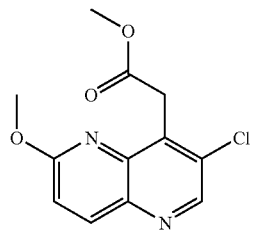

To a solution of dimethyl[3-chloro-6-(methyloxy)-1,5-naphthyridin-4-yl]propanedioate (56.23 g, 173 mmol) in DMSO (1210 ml) was added lithium chloride (14.9 g, 350 mmol) and water (3.24 ml, 180 mmol). The mixture was heated to 100° C. for 16 h then cooled and treated with ethyl acetate and water. The organic phase was washed twice with water, the aqueous extracted with ethyl acetate and this water-washed. The combined organic phases were dried and the solvent was removed. The residue was subjected to column chromatography on silica gel using a hexane and ethyl acetate gradient to provide the desired compound containing a little of the starting material (43.3 g, 94%).

MS (ES+) m/z 267 (MH+, 100%).

(c) Methyl 2-[3-chloro-6-(methyloxy)-1,5-naphthyridin-4-yl]-2-propenoate

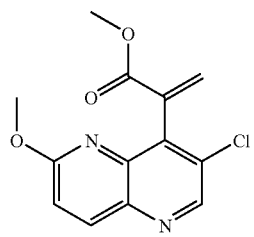

A mixture of methyl[3-chloro-6-(methyloxy)-1,5-naphthyridin-4-yl]acetate (43.3 g, 162 mmol), benzyltriethylammonium chloride (71.2 g, 313 mmol), potassium carbonate (42 g, 304 mmol) and paraformaldehyde (42 g) in cyclohexane (1060 ml) was heated at 80° C. for 24 h, cooled and treated with ethyl acetate and water. After separation, the aqueous was extracted with ethyl acetate. The combined organic phases were dried and the solvent was removed. The residue was subjected to column chromatography on silica gel using hexane/15% ethyl acetate to provide the desired compound (40.2 g, 89%).

MS (ES+) m/z 279 (MH+, 100%).

(d) Methyl 2-[3-chloro-6-(methyloxy)-1,5-naphthyridin-4-yl]-3-[4-({[(1,1-dimethylethyl)oxy]carbonyl}amino-1-piperidinyl}propanoate

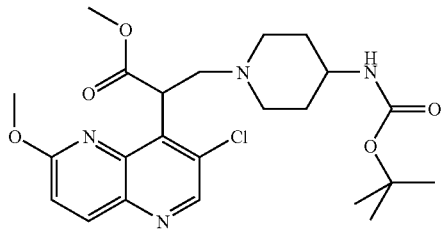

A mixture of methyl 2-[3-chloro-6-(methyloxy)-1,5-naphthyridin-4-yl]-2-propenoate (4.94 g, 17.75 mmol), 4-t-butoxycarbonylaminopiperidine (3.5 g, 19 mmol) and 1,1,3,3-tetramethylguanidine (0.3 ml) in DMF (20 ml) was heated at 80° C. for 7 hours, cooled and evaporated to dryness. Chromatography, eluting with 15% ethyl acetate/dichloromethane, gave the product mixed with a little starting material and a little DMF (8.76 g).

MS (APCI+) m/z 479 (MH+, 100%).

(e) 1,1-Dimethylethyl (1-{2-[3-chloro-6-(methyloxy)-1,5-naphthyridin-4-yl]-3-hydroxypropyl}-4-piperidinyl)carbamate

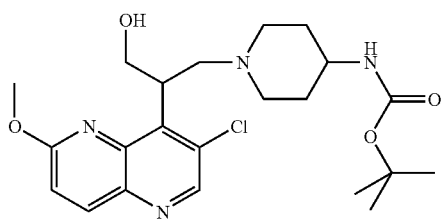

A solution of methyl 2-[3-chloro-6-(methyloxy)-1,5-naphthyridin-4-yl]-3-[4-({[(1,1-dimethylethyl)oxy]carbonyl}amino-1-piperidinyl}propanoate (4.25 g, 8.9 mmol) in THF (100 ml) at −70° C. under argon was treated dropwise with a 1M solution of lithium aluminium hydride in THF (10.5 ml) and allowed to warm gradually to 0° C. The solution was stirred at this temperature for 3 hours, treated with water (0.79 ml), 2N sodium hydroxide (1.48 ml) and water (1.7 ml), stirred 1 hour at room temperature and filtered. The solid was washed with THF, the total filtrate was evaporated and the residue chromatographed, eluting with methanol/dichloromethane to give product (2.17 g, 54%).

MS (APCI+) m/z 451 (MH+, 100%).

(f) 1,1-Dimethylethyl{1-[(3-chloro-7-oxo-4,5-dihydro-7H-pyrrolo[3,2,1-de]-1,5-naphthyridin-4-yl)methyl]-4-piperidinyl}carbamate

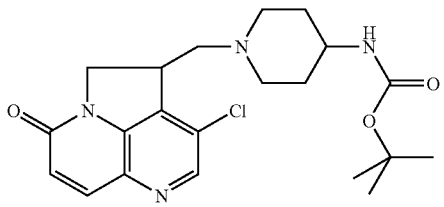

To a solution of 1,1-dimethylethyl(1-{2-[3-chloro-6-(methyloxy)-1,5-naphthyridin-4-yl]-3-hydroxypropyl}-4-piperidinyl)carbamate (3.08 g of an impure batch, considered to contain 2 g, 4.44 mmol) in dichloromethane (20 ml) at 0° C. was added triethylamine (0.97 ml, 7 mmol) and methanesulfonyl chloride (0.426 ml, 5.5 mmol). The reaction was warmed to room temperature and stirred for 18 h and then heated at 35° C. for 7 h. The reaction mixture was then diluted with dichloromethane and washed with aqueous sodium bicarbonate solution. The aqueous phase was extracted twice with dichloromethane and the combined organic phases were dried and the solvent was removed. The residue was subjected to column chromatography on silica gel using a dichloromethane and methanol gradient to provide the desired compound (1.475 g, 79%).

MS (ES+) m/z 419 (MH+, 20%), 319 (100%).

(g) 4-[(4-Amino-1-piperidinyl)methyl]-3-chloro-4,5-dihydro-7H-pyrrolo[3,2,1-de]-1,5-naphthyridin-7-one

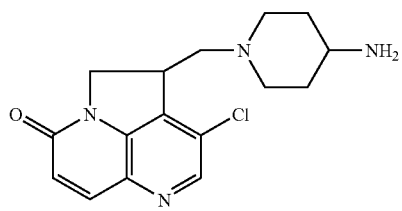

A suspension of 1,1-dimethylethyl{1-[(3-chloro-7-oxo-4,5-dihydro-7H-pyrrolo[3,2,1-de]-1,5-naphthyridin-4-yl)methyl]-4-piperidinyl}carbamate (1.475 g, 4.63 mmol) in dichloromethane (15 ml) was treated with trifluoroacetic acid (12 ml) and stirred at room temperature for 1 h. The reaction mixture was evaporated and then treated with aqueous sodium bicarbonate solution and a 4:1 dichloromethane:methanol solution. The aqueous phase was extracted about 15 times with a 4:1 dichloromethane:methanol solution and then the combined organic phases were dried and the solvent was removed. The residue was subjected to column chromatography on silica gel using a dichloromethane, methanol and aqueous ammonia gradient to provide the desired compound (0.94 g, 84%).

MS (ES+) m/z 319 (MH+, 30%), 152 (100%).

(h) Title Compound

A mixture of 4-[(4-amino-1-piperidinyl)methyl]-3-chloro-4,5-dihydro-7H-pyrrolo[3,2,1-de]-1,5-naphthyridin-7-one (75 mg, 0.236 mmol), 2,3-dihydro[1,4]dioxino[2,3-c]pyridine-7-carboxaldehyde (for a synthesis see WO2004058144, Example 2(c)) (39 mg, 0.236 mmol) and 3A molecular sieves in chloroform (1.5 ml) and methanol (1.5 ml) was heated at 65° C. for 3 h, cooled and then sodium triacetoxyborohydride (100 mg, 0.472 mmol) was added. The reaction was stirred at room temperature for 18 h, filtered through kieselguhr and evaporated. The residue was treated with aqueous sodium bicarbonate solution and a 4:1 dichloromethane:methanol mixture. The aqueous phase was extracted twice with a 4:1 dichloromethane:methanol mixture and then the combined organic phases were dried and the solvent was removed under reduced pressure. The residue was subjected to column chromatography on silica gel using a dichloromethane, methanol and aqueous ammonia gradient to provide the free base of the title compound (0.087 g, 79%).

$^1$H NMR δ (CDCl$_3$) 1.35-1.5 (2H, m), 1.8-2.0 (2H, m), 2.11 (1H, dt), 2.28 (1H, dt), 2.40-2.60 (2H, m), 2.73 (1H, broad d), 2.95-3.05 (2H, m), 3.80 (2H, s), 3.95-4.05 (1H, m), 4.25-4.35 (4H, m), 4.42 (1H, dd, J 13 and 9 Hz), 4.58 (1H, dd, J 13 and 4 Hz), 6.83 (1H, s), 6.87 (1H, d, J 10 Hz), 7.88 (1H, d, J 10 Hz), 8.11 (1H, s), 8.38 (1H, s). MS (ES+) m/z 468 (MH+, 40%), 150 (100%).

The free base of the title compound was converted to the hydrochloride by dissolving in dichloromethane/methanol and adding 1 equivalent of 1M HCl/diethyl ether then evaporating to dryness. MS as that of free base.

Example 3A

Racemic 3-chloro-4-[(4-{[(3-oxo-3,4-dihydro-2H-pyrido[3,2-h][1,4]thiazin-6-yl)methyl]amino}-1-piperidinyl)methyl]-4,5-dihydro-7H-pyrrolo[3,2,1-de]-1,5-naphthyridin-7-one Hydrochloride

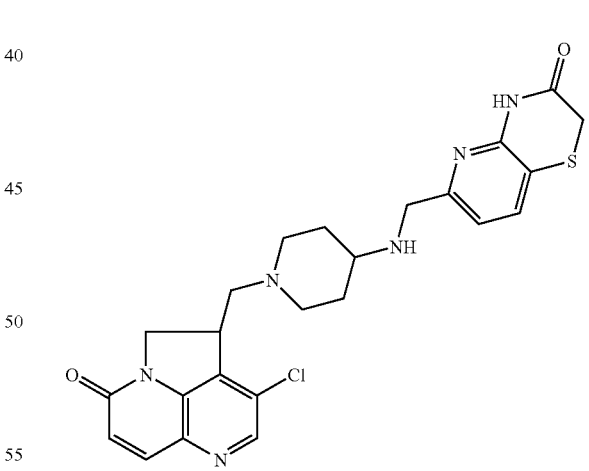

The free base of the title compound was prepared according to Example 2(h) from 4-[(4-amino-1-piperidinyl)methyl]-3-chloro-4,5-dihydro-7H-pyrrolo[3,2,1-de]-1,5-naphthyridin-7-one (150 mg) and 3-oxo-3,4-dihydro-2H-pyrido[3,2-b][1,4]thiazine-6-carbaldehyde (for a synthesis see WO2003087098, Example 301(d)) (92 mg) in 88% yield.

$^1$H NMR δ (CDCl$_3$) 1.35-1.5 (2H, m), 1.8-2.0 (2H, m), 2.11 (1H, dt), 2.28 (1H, dt), 2.40-2.60 (2H, m), 2.74 (1H, broad d), 2.95-3.05 (2H, m), 3.48 (2H, s), 3.84 (2H, s), 3.95-4.05 (1H, m), 4.42 (1H, dd, J 13 and 9 Hz), 4.58 (1H, dd, J 13 and 4 Hz), 6.87 (1H, d, J 10 Hz), 6.99 (1H, d, J 8 Hz), 7.58 (1H, d, J 8 Hz), 7.89 (1H, d, J 10 Hz), 8.11 (1H, s), 8.29 (1H, broad s), 8.38 (1H, s).

MS (ES+) m/z 497 (MH$^+$, 40%), 291 (100%).

A portion of the free base of the title compound was converted to the hydrochloride by dissolving in chloroform and adding 1 equivalent of 1M HCl/diethyl ether then evaporating to dryness. MS as that of free base.

Example 3B

Racemic 3-chloro-4-[(4-{[(3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one dihydrochloride Racemic 3-chloro-4-[(4-{[(3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one was converted to the dihydrochloride by dissolving in chloroform and adding 1M HCl/diethyl ether then evaporating to dryness. MS as that of free base.

Examples 4 and 5

3-Chloro-4-[(4-{[(3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one Dihydrochloride Enantiomer 1 and Enantiomer 2

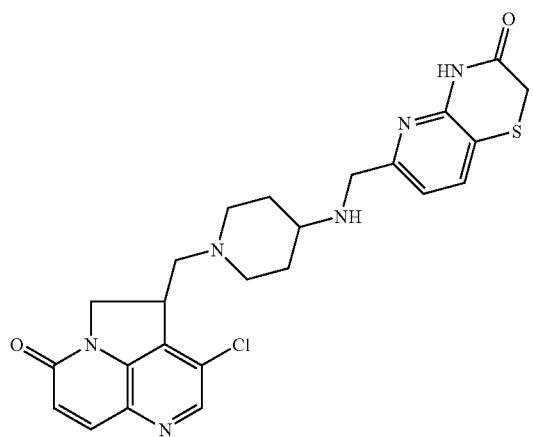

Racemic 3-chloro-4-[(4-{[(3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one) (60 mg) was dissolved in N-methylpyrrolidinone (3 mL) and resolved through multiple injections (100×0.6 mg substrate injection) on a Chiralpak IL column (5 microns) eluting with 0.1% isopropylamine in CH$_3$CN and 0.1% isopropylamine in iso-propyl alcohol at a flow rate of 1.0 mL/minute with UV detection at 320 nm. 3-Chloro-4-[(4-{[(3-oxo-3,4-dihydro-2H-pyrido[3,2-b][1,4]thiazin-6-yl)methyl]amino)-1-piperidinyl)methyl]-4,5-dihydro-7H-pyrrolo[3,2,1-de]-1,5-naphthyridin-7-one) fast running enantiomer (>99% ee, retention time 10.8 minutes, designated Enantiomer 1) (31 mg after conversion into dihydrochloride salt) and 3-chloro-4-[(4-{[(3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one) slow running enantiomer (98% ee, retention time 13.2 minutes, designated Enantiomer 2) (31 mg after conversion into dihydrochloride salt) were obtained.

Enantiomer 1 showed [α]$_D$+31.7° (methanol, c=1.00%, 25° C.)
Enantiomer 2 showed [α]$_D$−31.4° (methanol, c=1.00%, 25° C.)

Example 6

3-Chloro-4-[(4-{[(3-oxo-3,4-dihydro-2H-pyrido[3,2-b][1,4]oxazin-6-yl)methyl]amino}-1-piperidinyl)methyl]-4,5-dihydro-7H-pyrrolo[3,2,1-de]-1,5-naphthyridin-7-one Hydrochloride

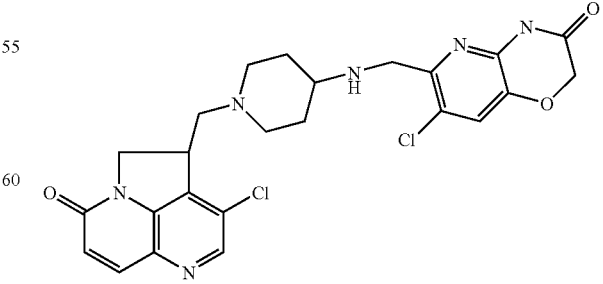

The free base of the title compound was prepared from 4-[(4-amino-1-piperidinyl)methyl]-3-chloro-4,5-dihydro-7H-pyrrolo[3,2,1-de]-1,5-naphthyridin-7-one (75 mg) and 3-oxo-3,4-dihydro-2H-pyrido[3,2-b][1,4]oxazine-6-carboxaldehyde (for a synthesis see WO2003087098, Example 31(e)) (42 mg) according to the general method of Example 2(h) in 76% yield.

$^1$H NMR δ (CDCl$_3$) 1.35-1.5 (2H, m), 1.8-2.0 (2H, m), 2.11 (1H, dt), 2.28 (1H, dt), 2.40-2.60 (2H, m), 2.74 (1H, broad d), 2.95-3.05 (2H, m), 3.82 (2H, s), 3.95-4.05 (1H, m), 4.42 (1H, dd, J 13 and 9 Hz), 4.59 (1H, dd, J 13 and 4 Hz), 4.64 (2H, s), 6.87 (1H, d, J 10 Hz), 6.94 (1H, d, J 8 Hz), 7.21 (1H, d, J 8 Hz), 7.89 (1H, d, J 10 Hz), 8.11 (1H, s), 8.38 (1H, s). MS (ES+) m/z 481 (MH$^+$, 15%), 163 (100%).

The free base of the title compound was converted to the hydrochloride by dissolving in chloroform and adding 1 equivalent of 1M HCl/diethyl ether then evaporating to dryness. MS as that of free base.

Example 7

3-Chloro-4-[(4-{[(7-chloro-3-oxo-3,4-dihydro-2H-pyrido[3,2-b][1,4]oxazin-6-yl)methyl]amino}-1-piperidinyl)methyl]4,5-dihydro-7H-pyrrolo[3,2,1-de]-1,5-naphthyridin-7-one Hydrochloride The free base of the title compound was prepared from 4-[(4-amino-1-piperidinyl)methyl]-3-chloro-4,5-dihydro- 7H-pyrrolo[3,2,1-de]-1,5-naphthyridin-7-one (75 mg) and 7-chloro-3-oxo-3,4-dihydro-2H-pyrido[3,2-b][1,4]oxazine-6-carboxaldehyde (for a synthesis see WO2003064421, Example 15(c)) (50 mg) according to the general method of Example 2(h) in 84% yield.

$^1$H NMR δ (CDCl$_3$) 1.45-1.6 (2H, m), 1.85-2.05 (2H, m), 2.13 (1H, dt), 2.30 (1H, dt), 2.49 (1H, t), 2.55-2.65 (1H, m), 2.76 (1H, broad d), 2.95-3.10 (2H, m), 3.96 (2H, s), 3.95-4.05 (1H, m), 4.42 (1H, dd, J 13 and 9 Hz), 4.59 (1H, dd, J 13 and 4 Hz), 4.64 (2H, s), 6.87 (1H, d, J 10 Hz), 7.25 (1H, s), 7.89 (1H, d, J 10 Hz), 8.11 (1H, s), 8.38 (1H, s). MS (ES+) m/z 515 (MH$^+$, 20%), 197 (100%).

The free base of the title compound was converted to the hydrochloride by dissolving in chloroform and adding 1 equivalent of 1M HCl/diethyl ether then evaporating to dryness. MS as that of free base.

Example 8

3-Chloro-4-[(4-{[(8-fluoro-2,3-dihydro-1,4-benzodioxin-6-yl)methyl]amino}-1-piperidinyl)methyl]-4,5-dihydro-7H-pyrrolo[3,2,1-de]-1,5-naphthyridin-7-one Hydrochloride

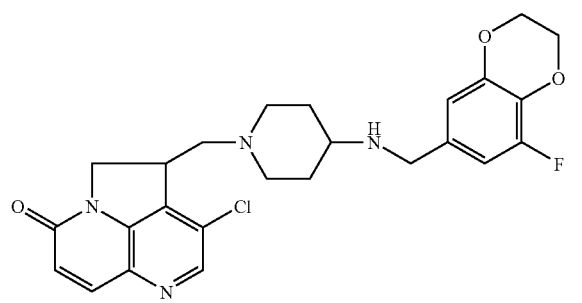

(a) 3-fluoro-4,5-dihydroxybenzaldehyde

To a solution of 3-fluoro-4-hydroxy-5-(methyloxy)benzaldehyde (5.0 g, 29.4 mmol) in dichloromethane (80 ml) at 0° C. was added boron tribromide (43 ml, 1M solution in dichloromethane) dropwise and then the reaction was allowed to stir for 1 h at rt before the solvent was removed under reduced pressure and the residue acidified with aqueous HCl (1M). The resultant solid was filtered, washed with water and dried in vacuo to give the desired compound (0.66 g, 14%).

MS (ES+) m/z 157 (MH$^+$, 100%).

(b) 8-fluoro-2,3-dihydro-1,4-benzodioxin-6-carboxaldehyde

To a solution of 3-fluoro-4,5-dihydroxybenzaldehyde (0.66 g, 4.2 mmol) in DMF (30 ml) was added potassium carbonate (1.15 g, 8.3 mmol) and 1,2-dibromoethane (0.72 ml, 8.3 mmol) and the resultant mixture was heated to 80° C. for 18 h before the solvent was removed under reduced pressure. The reaction mixture was then treated with dichloromethane and water. The aqueous phase was extracted twice with dichloromethane and the combined organic phases were dried and the solvent was removed under reduced pressure to give the desired compound as a cream solid (0.73 g, 95%).

MS (ES+) m/z 183 (MH$^+$, 100%).

(c) Title Compound

The free base of the title compound was prepared from 4-[(4-amino-1-piperidinyl)methyl]-3-chloro-4,5-dihydro-7H-pyrrolo[3,2,1-de]-1,5-naphthyridin-7-one (32 mg) and 8-fluoro-2,3-dihydro-1,4-benzodioxin-6-carboxaldehyde (18.2 mg) according to the general method of Example 2(h) in 56% yield.

$^1$H NMR δ (CDCl$_3$) 1.35-1.5 (2H, m), 1.8-2.0 (2H, m), 2.10 (TH, dt), 2.27 (1H, dt), 2.40-2.60 (2H, m), 2.72 (TH, broad d), 2.95-3.05 (2H, m), 3.69 (2H, s), 3.95-4.05 (1H, m), 4.25-4.35 (4H, m), 4.42 (1H, dd, J 13 and 9 Hz), 4.58 (1H, dd, J 13 and 4 Hz), 6.60-6.70 (2H, m), 6.87 (1H, d, J 10 Hz), 7.89 (1H, d, J 10 Hz), 8.38 (1H, s). MS (APCI+) m/z 485 (MH$^+$, 70%), 219 (100%).

The free base of the title compound was converted to the hydrochloride by dissolving in chloroform and adding 1 equivalent of 1M HCl/diethyl ether then evaporating to dryness. MS as that of free base.

Example 9

N-{1-[(3-Chloro-7-oxo-4,5-dihydro-7H-pyrrolo[3,2,1-de]-1,5-naphthyridin-4-yl)methyl]-4-piperidinyl}-3-oxo-3,4-dihydro-2H-pyrido[3,2-b][1,4]thiazine-6-carboxamide Hydrochloride

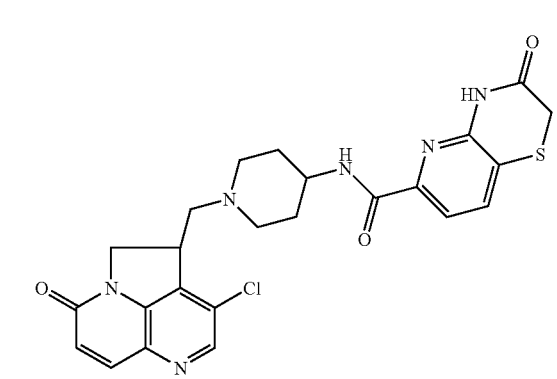

To a solution of 3-oxo-3,4-dihydro-2H-pyrido[3,2-b][1,4]thiazine-6-carboxylic acid (for a synthesis see WO2003087098, Example 301(b)) (50 mg, 0.236 mmol), 4-[(4-amino-1-piperidinyl)methyl]-3-chloro-4,5-dihydro-7H-pyrrolo[3,2,1-de]-1,5-naphthyridin-7-one (75 mg, 0.236 mmol) and triethylamine (0.066 ml 0.472 mmol) in DMF (2 ml) was added HATU (95 mg, 0.25 mmol) and the reaction was stirred at room temperature for 18 h. The reaction mixture was then evaporated to dryness, kept under high vacuum for 30 minutes, treated with dichloromethane and aqueous sodium bicarbonate solution and stirred vigorously for 30 minutes. The solid was filtered off, washed with water and dichloromethane and dried in vacuo to provide the free base of the title compound (100 mg, 83%).

$^1$H NMR δ (d$_6$-DMSO) 1.45-1.6 (2H, m), 1.8-1.95 (2H, m), 2.17 (1H, t), 2.36 (1H, t), 2.60-2.80 (2H, m), 2.91 (1H, dd), 3.01 (1H, broad d), 3.63 (2H, s), 3.75-3.85 (1H, m), 4.10-4.20 (TH, m), 4.25-4.45 (2H, m), 6.82 (TH, d, J 10 Hz), 7.58 (1H, d, J 8 Hz), 7.95 (1H, d, J 8 Hz), 7.99 (1H, d, J 10 Hz), 8.05 (1H, d, J 8 Hz), 8.45 (1H, s).

MS (ES−) m/z 509 ([M−H]$^−$, 100%).

The free base of the title compound was converted to the hydrochloride by suspending in ice-cooled 1:1 chloroform/methanol and adding 1 equivalent of 1M HCl/diethyl ether (solution obtained), then evaporating to dryness. MS as that of free base.

Example 10

4-({4-[(2,3-dihydro[1,4]dioxino[2,3-c]pyridin-7-ylmethyl)amino]-1-piperidinyl}methyl)-3-fluoro-4,5-dihydro-7H-pyrrolo[3,2,1-de]-1,5-naphthyridin-7-one Hydrochloride

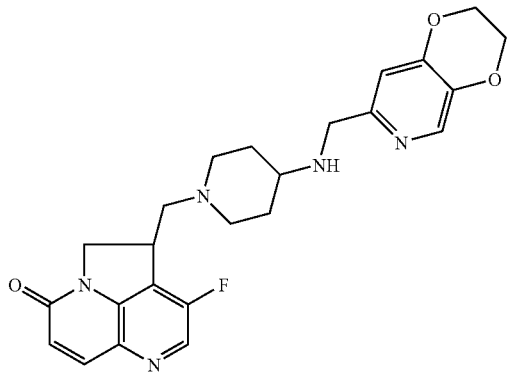

(a) Dimethyl[3-fluoro-6-(methyloxy)-1,5-naphthyridin-4-yl]propanedioate

Method 1

To a solution of dimethylmalonate (6.05 ml, 53 mmol) in dry 1,4-dioxane (200 ml) was added sodium hydride (60% dispersion in oil)(2.12 g, 53 mmol). The mixture was stirred for 10 mins. and sonicated for 10 minutes before adding palladium acetate (0.5 g, 2.2 mmol). Argon was bubbled through for a short time, then 8-bromo-7-fluoro-2-(methyloxy)-1,5-naphthyridine (for a synthesis see WO2004058144, Example 53(g)) (5 g, 19.4 mmol) and tri-tert-butylphosphine (0.5 g, 2.5 mmol) were added. The reaction mixture was then heated at 95° C. under argon for 96 h. The reaction mixture was then cooled and treated with water, HCl (2N, 26.5 ml) and ethyl acetate. The organic phase was dried and the solvent was removed under reduced pressure. The residue was subjected to column chromatography on silica gel using hexane/20% ethyl acetate to provide the desired compound (3.55 g, about 80% pure).

MS (APCI+) m/z 309 (MH+, 100%).

Method 2

A solution of dimethylmalonate (68.6 ml, 600 mmol) in dry 1,4-dioxane (750 ml) under argon was stirred with an overhead stirrer and treated with sodium hydride (22 g of a 60% dispersion in oil, 550 mmol). When bubbling subsided, the mixture was heated to 80° C. for 2.5 hours, by which time it was an even slurry. Copper(I) bromide (10 g) was added and, after 5 minutes, 8-bromo-7-fluoro-2-(methyloxy)-1,5-naphthyridine (51.4 g, 200 mmol). The temperature was raised to 100° C. and stirring continued for 20 hours. The mixture was cooled, poured into ethyl acetate (1 litre)/water (1 litre)/2N HCl (175 ml), shaken and filtered through kieselguhr. The pH of the aqueous phase was adjusted to 3-4, the mixture shaken and separated. The organic phase was washed with dilute brine, the aqueous phase was extracted with ethyl acetate and washed, and the total organic solvent was dried and evaporated. Chromatography using a hexane/ethyl acetate gradient provided the desired compound (56.08 g, 90%).

(b) Methyl[3-fluoro-6-(methyloxy)-1,5-naphthyridin-4-yl]acetate

A mixture of dimethyl[3-fluoro-6-(methyloxy)-1,5-naphthyridin-4-yl]propanedioate (52 g, 169 mmol), lithium chloride (14.5 g, 340 mmol) and water (3.43 ml, 190 mmol) in DMSO (1175 ml) was heated at 100° C. for 24 hours and cooled. The solution was shaken with water and ethyl acetate, separated and the organic phase washed twice with water. The total aqueous was re-extracted with ethyl acetate and this water-washed. The combined organic phase was dried and evaporated and the residue chromatographed, using a hexane/ethyl acetate gradient, to give the desired product containing about 10% of starting material (35.79 g).

(c) Methyl 2-[3-fluoro-6-(methyloxy)-1,5-naphthyridin-4-yl]-2-propenoate

A mixture of methyl[3-fluoro-6-(methyloxy)-1,5-naphthyridin-4-yl]acetate (35.79 g, 143 mmol), benzyltriethylammonium chloride (51.5 g), potassium carbonate (30.4 g) and paraformaldehyde (30.4 g) in cyclohexane (1 litre) was stirred at 80° C. under argon overnight, cooled and shaken with water and ethyl acetate. After separation, the aqueous was re-extracted with ethyl acetate and the combined organic phases dried and evaporated. Chromatography, eluting with 15% ethyl acetate/hexane, provided the product (24.66 g, 66%).

(d) Methyl 3-[4-({[(1,1-dimethylethyl)oxy]carbonyl}amino)-1-piperidinyl]-2-[3-fluoro-6-(methyloxy)-1,5-naphthyridin-4-yl]propanoate A mixture of methyl 2-[3-fluoro-6-(methyloxy)-1,5-naphthyridin-4-yl]-2-propenoate (15 g, 57.3 mmol), 4-t-butoxycarbonylaminopiperidine (13.2 g, 66 mmol) and 1,1,3,3-tetramethylguanidine (1 ml) in DMF (65 ml) was heated at 80° C. for 5 hours, cooled and evaporated. Chromatography (methanol/dichloromethane gradient) gave the product (26.63 g) containing about 9% DMF by weight.

(e) 1,1-Dimethylethyl (1-{2-[3-fluoro-6-(methyloxy)-1,5-naphthyridin-4-yl]-3-hydroxypropyl}-4-piperidinyl)carbamate A solution of methyl 3-[4-({[(1,1-dimethylethyl)oxy]carbonyl}amino)-1-piperidinyl]-2-[3-fluoro-6-(methyloxy)-1,5-naphthyridin-4-yl]propanoate (26.63 g, containing about 9% DMF by weight, estimate 52.5 mmol) was stirred under argon at −70° C. and treated with a 1M solution of lithium aluminium hydride in THF (60 ml). The mixture was allowed to warm to −10° C., stirred in an ice bath for 2 hours, treated with water (4.5 ml), 2N NaOH solution (8.44 ml) and water (9.7 ml) and stirred a further 30 minutes. The solid was filtered off and washed with THF and the filtrate evaporated. Chromatography of the residue (methanol/dichloromethane gradient) gave the product (18.28 g).

MS (APCI+) m/z 435 (MH+, 100%).

(f) 1,1-Dimethylethyl {1-[(3-fluoro-7-oxo-4,5-dihydro-7H-pyrrolo[3,2,1-de]-1,5-naphthyridin-4-yl)methyl]-4-piperidinyl}carbamate A solution of 1,1-dimethylethyl (1-{2-[3-fluoro-6-(methyloxy)-1,5-naphthyridin-4-yl]-3-hydroxypropyl}-4-piperidinyl)carbamate (18.28 g, containing some non-alcohol impurity and a little MeOH, judged to contain 40 mmol alcohol-containing compounds) in dichloromethane (180 ml) was stirred under argon, ice-cooled and treated with triethylamine (11.1 ml, 80 mmol) and methanesulfonic anhydride (8.7 g, 50 mmol). After 1 hour the solution was heated to reflux for 2 days, evaporated and redissolved in chloroform (180 ml). This solution was heated under argon at 55° C. for 3 days, cooled, washed with aqueous sodium bicarbonate and the aqueous twice re-extracted with chloroform. The combined organic phases were dried and evaporated. Chromatography of the residue (methanol/dichloromethane gradient) and rechromatography of some impure fractions gave the product (13.35 g, containing 12.5% dichloromethane by weight).

MS (ES+) m/z 425 (MNa+, 20%), 303 (100%).

(g) 4-[(4-Amino-1-piperidinyl)methyl]-3-fluoro-4,5-dihydro-7H-pyrrolo[3,2,1-de]-1,5-naphthyridin-7-one A solution of 1,1-dimethylethyl {1-[(3-fluoro-7-oxo-4,5-dihydro-7H-pyrrolo[3,2,1-de]-1,5-naphthyridin-4-yl)methyl]-4-piperidinyl}carbamate (13.35 g, containing about 12.5% dichloromethane) in dichloromethane (125 ml) was ice-cooled, treated with TFA (100 ml), stirred at room temperature for 1 hour and evaporated. The residue was shaken with aqueous sodium bicarbonate (excess) and 15% methanol/dichloromethane, separated and the aqueous extracted about 50 times with 15% methanol/dichloromethane. The combined organic phases were dried and evaporated and the residue chromatographed using dichloromethane/methanol/0.88 ammonia 9:1:0.1 to give the product (8.1 g).

MS (APCI+) m/z 303 (MH+, 50%), 202 (100%).

(h) Title Compound

The free base of the title compound was prepared from 4-[(4-amino-1-piperidinyl)methyl]-3-fluoro-4,5-dihydro-7H-pyrrolo[3,2,1-de]-1,5-naphthyridin-7-one (32 mg) and 2,3-dihydro[1,4]dioxino[2,3-c]pyridine-7-carboxaldehyde (for a synthesis see WO2004058144, Example 2(c) (17.5 mg) according to the general method of Example 2(h), (32 mg, 67%).

$^1$H NMR δ (CDCl$_3$) 1.35-1.5 (2H, m), 1.8-2.0 (2H, m), 2.11 (1H, dt), 2.24 (1H, dt), 2.50-2.60 (2H, m), 2.75-2.90 (2H, m), 2.96 (1H, broad d), 3.80 (2H, s), 4.05-4.15 (1H, m), 4.25-4.35 (4H, m), 4.40-4.55 (2H, m), 6.80-6.90 (2H, m), 7.88 (1H, d, J 10 Hz), 8.11 (1H, s), 8.32 (1H, s). MS (ES+) m/z 452 (MH+, 40%), 150 (100%).

The free base of the title compound was converted to the hydrochloride by dissolving in chloroform and adding 1 equivalent of 1M HCl/diethyl ether then evaporating to dryness. MS as that of free base.

Example 11

3-Fluoro-4-[(4-{[(3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one Hydrochloride

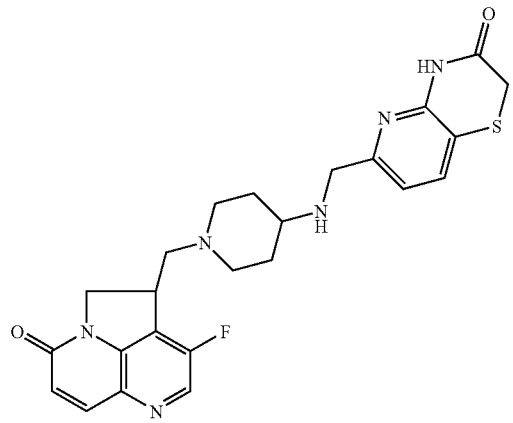

The free base of the title compound was prepared from 4-[(4-amino-1-piperidinyl)methyl]-3-fluoro-4,5-dihydro-7H-pyrrolo[3,2,1-de]-1,5-naphthyridin-7-one and 3-oxo-3,4-dihydro-2H-pyrido[3,2-b][1,4]thiazine-6-carboxaldehyde (for a synthesis see WO2003087098, Example 301(d)) according to the general method of Example 2(h) in 65% yield.

$^1$H NMR δ (CDCl$_3$) 1.4-1.55 (2H, m), 1.8-2.0 (2H, m), 2.12 (1H, dt), 2.24 (1H, dt), 2.50-2.60 (2H, m), 2.75-2.90 (2H, m), 2.98 (1H, broad d), 3.48 (2H, s), 3.85 (2H, s), 4.05-4.15 (1H, m), 4.40-4.55 (2H, m), 6.83 (1H, d, J 10 Hz), 6.99 (1H, d, J 8 Hz), 7.58 (1H, d, J 8 Hz), 7.89 (1H, d, J 10 Hz), 8.21 (1H, broad s), 8.33 (1H, s). MS (ES+) m/z 481 (MH+, 30%), 179 (100%).

The free base of the title compound was converted to the hydrochloride by dissolving in chloroform and adding 1 equivalent of 1M HCl/diethyl ether then evaporating to dryness. MS as that of free base.

Example 12

N-{1-[(3-Fluoro-7-oxo-4,5-dihydro-7H-pyrrolo[3,2,1-de]-1,5-naphthyridin-4-yl)methyl]-4-piperidinyl}-3-oxo-3,4-dihydro-2H-pyrido[3,2-b][1,4]oxazine-6-carboxamide hydrochloride

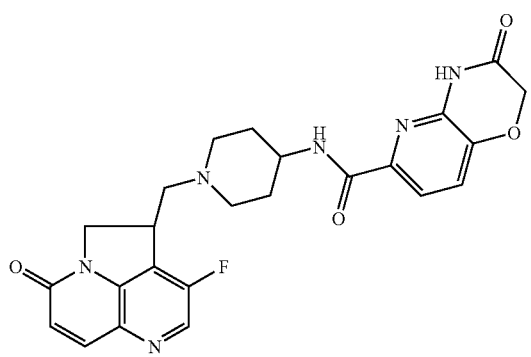

A mixture of 4-[(4-amino-1-piperidinyl)methyl]-3-fluoro-4,5-dihydro-7H-pyrrolo[3,2,1-de]-1,5-naphthyridin-7-one (0.35 mmol, mixed with some DMF) and 3-oxo-3,4-dihydro-2H-pyrido[3,2-b][1,4]oxazine-6-carboxylic acid (for a synthesis see WO2004058144, Example 65) (68 mg, 0.5 mmol) in DMF (3 ml) was treated with triethylamine (0.243 ml, 1.75 mmol) and HATU (145 mg, 0.38 mmol) and stirred at room temperature overnight. Solvent was evaporated and the residue dried under high vacuum and treated with dichloromethane and aqueous sodium bicarbonate solution. After stirring vigorously for 30 minutes, the solid was filtered off, washed with water and dichloromethane and dried to provide the free base of the title compound (82 mg, 49%).

$^1$H NMR δ (d$_6$-DMSO) 1.45-1.6 (2H, m), 1.8-1.95 (2H, m), 2.17 (1H, t), 2.30 (1H, t), 2.60-2.80 (2H, m), 2.82 (1H, broad d), 2.95 (1H, broad d), 3.7-3.85 (1H, m), 4.15-4.3 (2H, m), 4.35-4.45 (1H, m), 4.74 (2H, s), 6.77 (1H, d, J 10 Hz), 7.46 (1H, d, J 8 Hz), 7.60 (1H, d, J 8 Hz), 7.86 (1H, d, J 8 Hz), 7.98 (1H, d, J 10 Hz), 8.45 (1H, s), 11.35 (1H, broad s).

MS (ES−) m/z 477 ([M−H]$^-$, 100%).

The free base of the title compound was converted to the hydrochloride by suspending in chloroform/methanol and adding 1 equivalent of 1M HCl/diethyl ether (solution obtained), then evaporating to dryness. MS as that of free base.

Example 13

3-Chloro-4-[((3R,4S)-4-{[(7-fluoro-2,3-dihydro-1,4-benzodioxin-6-yl)methyl]amino}-3-hydroxy-1-piperidinyl)methyl]-4,5-dihydro-7H-pyrrolo[3,2,1-de]-1,5-naphthyridin-7-one, Diastereomer 1 Hydrochloride

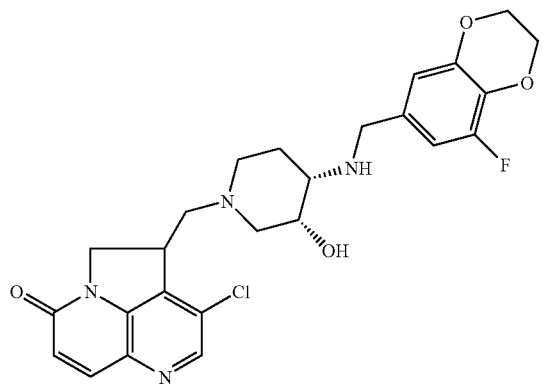

(a) Racemic methyl 2-[3-chloro-6-(methyloxy)-1,5-naphthyridin-4-yl]-3-[(3R,4S)-4-({[(1,1-dimethylethyl)oxy]carbonyl}amino-3-hydroxy-1-piperidinyl}propanoate A mixture of methyl 2-[3-chloro-6-(methyloxy)-1,5-naphthyridin-4-yl]-2-propenoate (1.86 g, 6.67 mmol), 1,1-dimethylethyl[(3R,4S)-3-hydroxy-4-piperidinyl]carbamate (for a synthesis see WO2004058144, Example 5(c), Enantiomer 1) (1.5 g) and 10 drops of 1,1,3,3-tetramethylguanidine in DMF (7.5 ml) was heated at 80° C. under argon for 4 hours, cooled and evaporated. Chromatography of the residue (eluting with 1% methanol/dichloromethane) gave the product (3.33 g), about 90% pure (major impurity DMF).

MS (APCI+) m/z 495 (MH$^+$, 100%).

(b) Racemic 1,1-dimethylethyl((3R,4S)-1-{2-[3-chloro-6-(methyloxy)-1,5-naphthyridin-4-yl]-3-hydroxypropyl}-3-hydroxy-4-piperidinyl)carbamate A solution of racemic methyl 2-[3-chloro-6-(methyloxy)-1,5-naphthyridin-4-yl]-3-[(3R,4S)-4-({[(1,1-dimethylethyl)oxy]carbonyl}amino-3-hydroxy-1-piperidinyl}propanoate (0.425 g) in THF (10 ml) at −70° C. under argon was treated with a 1M solution of lithium aluminium hydride in THF (1.05 ml) and allowed to warm to 0° C. The mixture was stirred in an ice bath for 2 hours, treated with water (0.079 ml), 2N NaOH solution (0.148 ml) and water (0.17 ml), stirred overnight, filtered through kieselguhr and evaporated. The reaction was repeated using a solution of racemic methyl 2-[3-chloro-6-(methyloxy)-1,5-naphthyridin-4-yl]-3-[(3R,4S)-4-({[(1,1-dimethylethyl)oxy]carbonyl}amino-3-hydroxy-1-piperidinyl}propanoate (2.9 g) in THF (68 ml) and a 1M solution of lithium aluminium hydride in THF (7.1 ml). The crude products of the 2 reactions were combined and chromatographed using a methanol/dichloromethane gradient to give the product (1.828 g, 58%).

MS (APCI+) m/z 467 (MH$^+$, 100%).

(c) Racemic 1,1-dimethylethyl{(3R,4S)-1-[(3-chloro-7-oxo-4,5-dihydro-7H-pyrrolo[3,2,1-de]-1,5-naphthyridin-4-yl)methyl]-3-hydroxy-4-piperidinyl}carbamate To a solution of racemic 1,1-dimethylethyl((3R,4S)-1-{2-[3-chloro-6-(methyloxy)-1,5-naphthyridin-4-yl]-3-hydroxypropyl}-3-hydroxy-4-piperidinyl)carbamate (100 mg, 0.214 mmol) in dichloromethane (1 ml) at 0° C. was added triethylamine (0.045 ml, 0.321 mmol) and toluenesulfonyl chloride (45 mg, 0.236 mmol). The reaction was warmed to room temperature, stirred for 118 h, when LCMS indicated a good conversion to the desired product. The reaction was repeated, using a solution of racemic 1,1-dimethylethyl ((3R,4S)-1-{2-[3-chloro-6-(methyloxy)-1,5-naphthyridin-4-yl]-3-hydroxypropyl}-3-hydroxy-4-piperidinyl)carbamate (1.728 g, 3.71 mmol) in dichloromethane (18 ml), triethylamine (0.78 ml, 5.6 mmol) and toluenesulfonyl chloride (815 mg, 4.25 mmol) (in this case stirring was continued for 3 days). The 2 reaction mixtures were combined then treated with dichloromethane and aqueous sodium bicarbonate solution. The aqueous phase was extracted twice with dichloromethane and the combined organic phases were dried and the solvent was removed. The residue was subjected to column chromatography on silica gel using a dichloromethane and methanol gradient to provide the desired compound (1.30 g, 76%).

MS (APCI+) m/z 435 (MH$^+$, 10%), 335 (100%).

(d) Racemic 4-{[(3R,4S)-4-amino-3-hydroxy-1-piperidinyl]methyl}-3-chloro-4,5-dihydro-7H-pyrrolo[3,2,1-de]-1,5-naphthyridin-7-one This compound was prepared from racemic 1,1-dimethylethyl{(3R,4S)-1-[(3-chloro-7-oxo-4,5-dihydro-7H-pyrrolo[3,2,1-de]-1,5-naphthyridin-4-yl)methyl]-3-hydroxy-4-piperidinyl}carbamate according to the general method of Example 2(g) (but requiring about 30 extractions of the aqueous solution with 4:1 dichloromethane/methanol) in 60% yield.

MS (APCI+) m/z 335 (MH$^+$, 100%).

(e) 4-{[(3R,4S)-4-Amino-3-hydroxy-1-piperidinyl]methyl}-3-chloro-4,5-dihydro-7H-pyrrolo[3,2,1-de]-1,5-naphthyridin-7-one Diastereomer 1 and Diastereomer 2

Racemic 4-{[(3R,4S)-4-amino-3-hydroxy-1-piperidinyl]methyl}-3-chloro-4,5-dihydro-7H-pyrrolo[3,2,1-de]-1,5-naphthyridin-7-one (400 mg) was subjected to preparative HPLC on Chiralpak AD. This procedure gave the faster running diastereomer (Diastereomer 1, 132 mg) in 99.6% de and the slower running diastereomer (Diastereomer 2, 134 mg) in 98.6% de.

(f) Title Compound

The free base of the title compound was prepared from 4-{[(3R,4S)-4-amino-3-hydroxy-1-piperidinyl]methyl}-3-chloro-4,5-dihydro-7H-pyrrolo[3,2,1-de]-1,5-naphthyridin-7-one Diastereomer 1 and 8-fluoro-2,3-dihydro-1,4-benzodioxin-6-carboxaldehyde according to the general method of Example 2(h), (I 5 mg, 48%).

$^1$H NMR δ (CDCl$_3$) 1.6-1.8 (2H, m), 2.2-2.4 (2H, m), 2.45-2.60 (2H, m), 2.71 (1H, broad d), 3.05-3.2 (2H, m), 3.71 (2H, ABq), 3.87 (1H, broad s), 3.95-4.05 (1H, m), 4.25-4.35 (4H, m), 4.46 (1H, dd, J 13 and 8 Hz), 4.53 (1H, dd, J 13 and 4 Hz), 6.6-6.7 (2H, m), 6.87 (1H, d, J 10 Hz), 7.89 (1H, d, J 10 Hz), 8.39 (1H, s).

MS (ES+) m/z 501 (MH$^+$, 40%), 167 (100%).

The free base of the title compound was converted to the hydrochloride by dissolving in chloroform and adding 1 equivalent of 1M HCl/diethyl ether then evaporating to dryness. MS as that of free base.

Example 14

3-Chloro-4-[((3R,4S)-4-{[(7-fluoro-2,3-dihydro-1,4-benzodioxin-6-yl)methyl]amino}-3-hydroxy-1-piperidinyl)methyl]-4,5-dihydro-7H-pyrrolo[3,2,1-de]-1,5-naphthyridin-7-one, Diastereomer 2 Hydrochloride

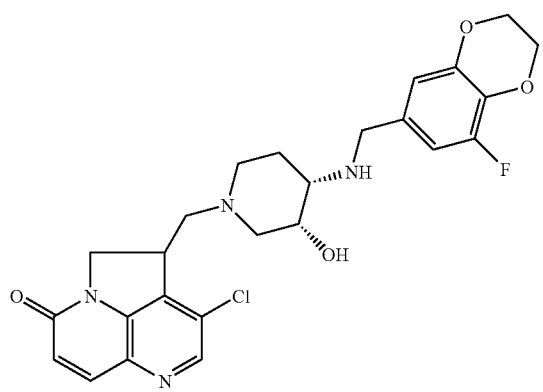

The free base of the title compound was prepared from 4-{[(3R,4S)-4-amino-3-hydroxy-1-piperidinyl]methyl}-3-chloro-4,5-dihydro-7H-pyrrolo[3,2,1-de]-1,5-naphthyridin-7-one Diastereomer 2 and 8-fluoro-2,3-dihydro-1,4-benzodioxin-6-carboxaldehyde according to the general method of Example 2(h), (16 mg, 42%).

$^1$H NMR δ (CDCl$_3$) 1.6-1.8 (2H, m), 2.16 (1H, dt), 2.40-2.60 (3H, m), 2.78 (1H, broad d), 2.93 (1H, broad d), 3.08 (1H, dd, J 13 and 4 Hz), 3.70 (2H, ABq), 3.84 (1H, broad s), 3.95-4.05 (1H, m), 4.25-4.35 (4H, m), 4.46 (1H, dd, J 13 and 9 Hz), 4.54 (1H, dd, J 13 and 4 Hz), 6.6-6.75 (2H, m), 6.87 (1H, d, J 10 Hz), 7.89 (1H, d, J 10 Hz), 8.39 (1H, s).

MS (APCI+) m/z 501 (MH$^+$, 40%), 167 (100%).

The free base of the title compound was converted to the hydrochloride by dissolving in chloroform and adding 1 equivalent of 1M HCl/diethyl ether then evaporating to dryness. MS as that of free base.

Example 15

4-({(3R,4S)-4-[(2,3-Dihydro[1,4]dioxino[2,3-c]pyridin-7-ylmethyl)amino]-3-hydroxy-1-piperidinyl}methyl)-3-fluoro-4,5-dihydro-7H-pyrrolo[3,2,1-de]-1,5-naphthyridin-7-one Hydrochloride

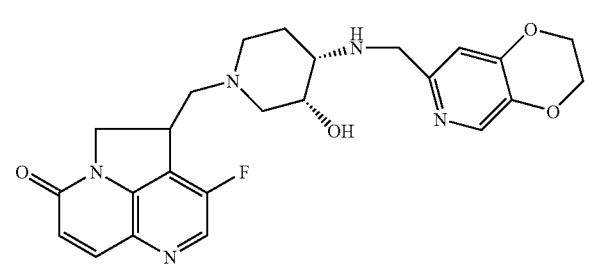

(a) Racemic methyl 2-[3-fluoro-6-(methyloxy)-1,5-naphthyridin-4-yl]-3-[(3R,4S)-4-({[(1,1-dimethylethyl)oxy]carbonyl}amino-3-hydroxy-1-piperidinyl}propanoate A mixture of methyl 2-[3-fluoro-6-(methyloxy)-1,5-naphthyridin-4-yl]-2-propenoate (1.74 g, 6.67 mmol), 1,1-dimethylethyl[(3R,4S)-3-hydroxy-4-piperidinyl]carbamate (for a synthesis see WO2004058144, Example 5(c), cis-(3-hydroxy-piperidin-4-yl-carbamic acid tert-butyl ester Enantiomer 1) (1.5 g) and 10 drops of 1,1,3,3-tetramethylguanidine in DMF (7.5 ml) was heated at 80° C. under argon for 3 hours, cooled and evaporated. Chromatography of the residue (eluting with a methanol/dichloromethane gradient) gave the product (3.27 g), about 90% pure (major impurity DMF).

MS (ES+) m/z 479 (MH$^+$, 100%).

(b) Racemic 1,1-dimethylethyl((3R,4S)-1-{2-[3-fluoro-6-(methyloxy)-1,5-naphthyridin-4-yl]-3-hydroxypropyl}-3-hydroxy-4-piperidinyl)carbamate A solution of racemic methyl 2-[3-fluoro-6-(methyloxy)-1,5-naphthyridin-4-yl]-3-[(3R,4S)-4-({[(1,1-dimethylethyl)oxy]carbonyl}amino-3-hydroxy-1-piperidinyl]propanoate (2.91 g, 6.1 mmol) in THF (70 ml) at −70° C. under argon was treated with a 1M solution of lithium aluminium hydride in THF (7.0 ml), allowed to warm to 0° C. and stirred in an ice bath for 2 hours. The mixture was treated with water (0.525 ml), 2N NaOH solution (0.985 ml) and water (1.13 ml), stirred 1 hour and filtered. The filtrate was evaporated and the residue chromatographed using a methanol/dichloromethane gradient to give the product (1.895 g, 69%).

MS (ES+) m/z 451 (MH$^+$, 100%).

(c) Racemic 1,1-dimethylethyl{(3R,4S)-1-[(3-fluoro-7-oxo-4,5-dihydro-7H-pyrrolo[3,2,1-de]-1,5-naphthyridin-4-yl)methyl]-3-hydroxy-4-piperidinyl}carbamate To a solution of racemic 1,1-dimethylethyl((3R,4S)-1-{2-[3-fluoro-6-(methyloxy)-1,5-naphthyridin-4-yl]-3-hydroxypropyl}-3-hydroxy-4-piperidinyl)carbamate (450 mg, 1 mmol) in chloroform (5 ml) at 0° C. was added triethylamine (0.278 ml, 2 mmol) and toluenesulfonic anhydride (359 mg, 1.1 mmol). The reaction was warmed to room temperature while stirring for 2 h and heated at 50° C. overnight, when LCMS indicated an essentially complete reaction. The procedure was repeated using a solution of racemic 1,1-dimethylethyl((3R,4S)-1-{2-[3-fluoro-6-(methyloxy)-1,5-naphthyridin-4-yl]-3-hydroxypropyl}-3-hydroxy-4-piperidinyl)carbamate (1.445 g, 3.22 mmol) in chloroform (15 ml), triethylamine (0.893 ml, 6.4 mmol) and toluenesulfonic anhydride (1.153 g, 3.53 mmol). The 2 reaction mixtures were combined and washed with aqueous sodium bicarbonate solution. The aqueous phase was extracted twice with chloroform and the combined organic phases were dried and the solvent was removed. The residue was subjected to column chromatography on silica gel using a dichloromethane and methanol gradient to provide the desired compound (1.423 g, 80%).

MS (ES+) m/z 419 (MH+, 10%), 319 (100%).

(d) Racemic 4-{[(3R,4S)-4-amino-3-hydroxy-1-piperidinyl]methyl}-3-fluoro-4,5-dihydro-7H-pyrrolo[3,2,1-de]-1,5-naphthyridin-7-one A solution of racemic 1,1-dimethylethyl{(3R,4S)-1-[(3-fluoro-7-oxo-4,5-dihydro-7H-pyrrolo[3,2,1-de]-1,5-naphthyridin-4-yl)methyl]-3-hydroxy-4-piperidinyl}carbamate (200 mg) in acetic acid (6 ml) was treated with a 4M solution of HCl in 1,4-dioxane (2 ml), stirred 2 h at room temperature and evaporated to dryness. A part solution/part suspension of this material in dichloromethane (8.5 ml) and methanol (1.5 ml) was treated with MP-carbonate resin (obtained from Argonaut Technologies) (1.2 g), stirred for 3 h, filtered and the resin washed well with 1:1 dichloromethane/methanol. The filtrate was evaporated and the residue chromatographed on silica gel, eluting with dichloromethane/methanol/0.88 ammonia (89:11:1.1) to give product (133 mg, 87%).

MS (ES+) m/z 319 (MH+, 100%).

(e) Title Compound

The free base of the title compound was prepared from racemic 4-{[(3R,4S)-4-amino-3-hydroxy-1-piperidinyl]methyl}-3-fluoro-4,5-dihydro-7H-pyrrolo[3,2,1-de]-1,5-naphthyridin-7-one and 2,3-dihydro[1,4]dioxino[2,3-c]pyridine-7-carboxaldehyde (for a synthesis see WO2004058144, Example 2(c)) according to the general method of Example 2(h), chromatographing with dichloromethane/methanol/0.88 ammonia 95:5:0.5 (20 mg, 42%).

1H NMR δ (CDCl3) 1.6-1.8 (2H, m), 2.15-2.50 (2H, m), 2.55-2.70 (2H, m), 2.8-3.1 (3H, m), 3.8-3.9 (3H, m), 4.05-4.15 (1H, m), 4.25-4.35 (4H, m), 4.35-4.45 (1H, m), 4.45-4.55 (1H, m), 6.8-6.9 (2H, m), 7.89 (1H, d, J 10 Hz), 8.10 (1H, s), 8.33 (1H, s).

MS (ES+) m/z 468 (MH+, 50%), 150 (100%).

The free base of the title compound was converted to the hydrochloride by dissolving in chloroform and adding 1 equivalent of 1M HCl/diethyl ether then evaporating to dryness. MS as that of free base.

Example 16

4-({(3R,4S)-4-[(2,3-Dihydro-1-benzofuran-5-ylmethyl)amino]-3-hydroxy-1-piperidinyl}methyl)-3-fluoro-4,5-dihydro-7H-pyrrolo[3,2,1-de]-1,5-naphthyridin-7-one Hydrochloride

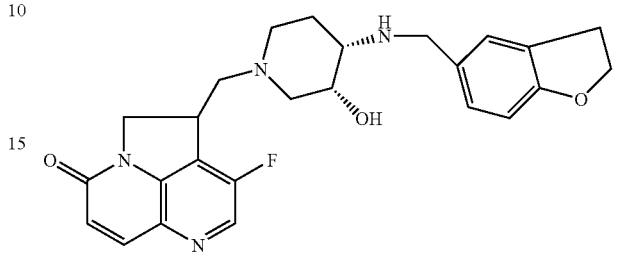

The free base of the title compound was synthesised from racemic 4-{[(3R,4S)-4-amino-3-hydroxy-1-piperidinyl]methyl}-3-fluoro-4,5-dihydro-7H-pyrrolo[3,2,1-de]-1,5-naphthyridin-7-one and 2,3-dihydro-1-benzofuran-5-carboxaldehyde according to the general method of Example 2(h), in 25% yield.

MS (ES+) m/z 451 (MH+, 20%), 133 (100%).

The free base of the title compound was converted to the hydrochloride by dissolving in chloroform and adding 1 equivalent of 1M HCl/diethyl ether then evaporating to dryness. MS as that of free base.

Example 17

4-({(3R,4S)-4-[(2,3-Dihydro-1,4-benzodioxin-6-ylmethyl)amino]-3-hydroxy-1-piperidinyl}methyl)-3-fluoro-4,5-dihydro-7H-pyrrolo[3,2,1-de]-1,5-naphthyridin-7-one Hydrochloride

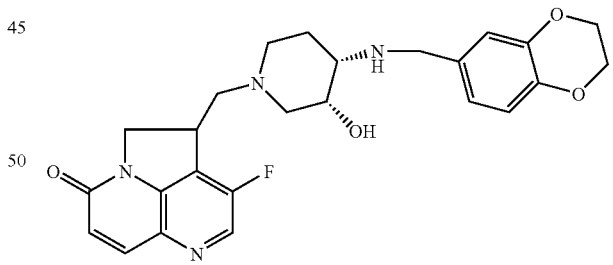

The free base of the title compound was synthesised from racemic 4-{[(3R,4S)-4-amino-3-hydroxy-1-piperidinyl]methyl}-3-fluoro-4,5-dihydro-7H-pyrrolo[3,2,1-de]-1,5-naphthyridin-7-one and 2,3-dihydro-1,4-benzodioxin-6-carboxaldehyde (Aldrich) according to the general method of Example 2(h), in 37% yield.

MS (ES+) m/z 467 (MH+, 30%), 149 (100%).

The free base of the title compound was converted to the hydrochloride by dissolving in chloroform and adding 1 equivalent of 1M HCl/diethyl ether then evaporating to dryness. MS as that of free base.

Example 18

3-chloro-4-[((3R,4S)-4-{[(7-Fluoro-3-oxo-3,4-dihydro-2H-1,4-benzothiazin-6-yl)methyl]amino}-3-hydroxy-1-piperidinyl)methyl]-4,5-dihydro-7H-pyrrolo[3,2,1-de]-1,5-naphthyridin-7-one Diastereomer 1 Hydrochloride

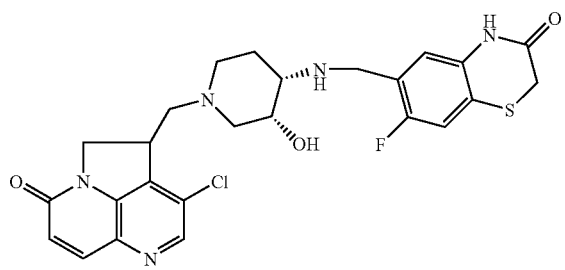

The free base of the title compound was synthesised from 4-{[(3R,4S)-4-amino-3-hydroxy-1-piperidinyl]methyl}-3-chloro-4,5-dihydro-7H-pyrrolo[3,2,1-de]-1,5-naphthyridin-7-one Diasteromer 1 and 7-fluoro-3-oxo-3,4-dihydro-2H-benzo[1,4]thiazine-6-carboxaldehyde (for a synthesis see WO2002056882, Example 22(g)) according to the general method of Example 2(h), in 38% yield.

MS (ES+) m/z 552 (MNa+, 40%), 530 (MH+, 40%), 196 (100%).

The free base of the title compound was converted to the hydrochloride by dissolving in chloroform and adding 1 equivalent of 1M HCl/diethyl ether then evaporating to dryness. MS as that of free base.

Example 19

3-Chloro-4-[((3R,4S)-4-{[(7-fluoro-3-oxo-3,4-dihydro-2H-1,4-benzothiazin-6-yl)methyl]amino}-3-hydroxy-1-piperidinyl)methyl]-4,5-dihydro-7H-pyrrolo[3,2,1-de]-1,5-naphthyridin-7-one Diastereomer 2 Hydrochloride

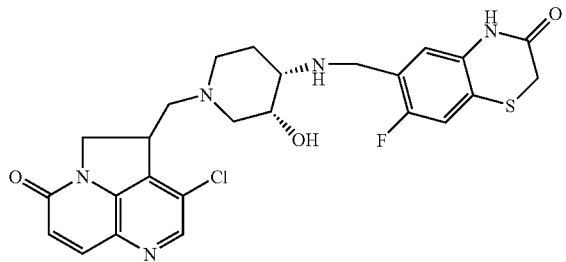

The free base of the title compound was synthesised from 4-{[(3R,4S)-4-amino-3-hydroxy-1-piperidinyl]methyl}-3-chloro-4,5-dihydro-7H-pyrrolo[3,2,1-de]-1,5-naphthyridin-7-one Diasteromer 2 and 7-fluoro-3-oxo-3,4-dihydro-2H-benzo[1,4]thiazine-6-carboxaldehyde (for a synthesis see WO2002056882, Example 22(g)), according to the general method of Example 2(h), in 35% yield.

MS (ES+) m/z 552 (MNa+, 40%), 530 (MH+, 40%), 196 (100%).

The free base of the title compound was converted to the hydrochloride by dissolving in chloroform and adding 1 equivalent of 1M HCl/diethyl ether then evaporating to dryness. MS as that of free base.

Example 20

3-Chloro-4-[((3R,4S)-3-hydroxy-4-{[(3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one hydrochloride

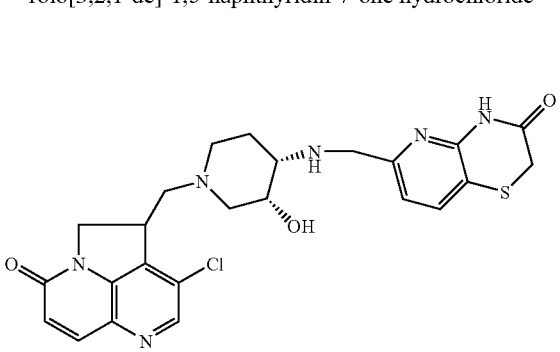

The free base of the title compound was synthesised from racemic 4-{[(3R,4S)-4-amino-3-hydroxy-1-piperidinyl]methyl}-3-chloro-4,5-dihydro-7H-pyrrolo[3,2,1-de]-1,5-naphthyridin-7-one and 3-oxo-3,4-dihydro-2H-pyrido[3,2-b][1,4]thiazine-6-carboxaldehyde (for a synthesis see WO2003087098, Example 301(d)) according to the general method of Example 2(h), in 49% yield.

MS (ES+) m/z 513 (MH+, 40%), 179 (100%).

The free base of the title compound was converted to the hydrochloride by dissolving in chloroform and adding 1 equivalent of 1M HCl/diethyl ether then evaporating to dryness. MS as that of free base.

Example 21

N-{(3R,4S)-1-[(3-Chloro-7-oxo-4,5-dihydro-7H-pyrrolo[3,2,1-de]-1,5-naphthyridin-4-yl)methyl]-3-hydroxy-4-piperidinyl}-3-oxo-3,4-dihydro-2H-pyrido[3,2-b][1,4]thiazine-6-carboxamide

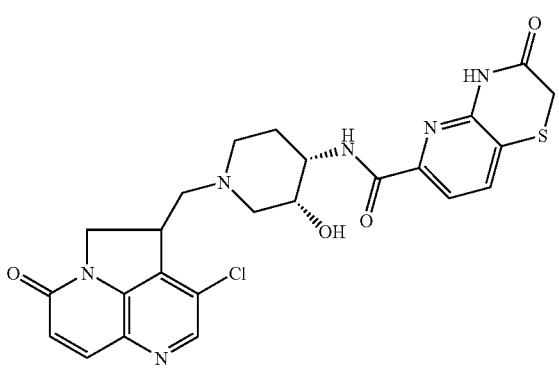

The free base of the title compound was synthesised from racemic 4-{[(3R,4S)-4-amino-3-hydroxy-1-piperidinyl]methyl}-3-chloro-4,5-dihydro-7H-pyrrolo[3,2,1-de]-1,5-naphthyridin-7-one (79 mg), 3-oxo-3,4-dihydro-2H-pyrido[3,2-b][1,4]thiazine-6-carboxylic acid (for a synthesis see WO2003087098, Example 301(b)) (50 mg), triethylamine (0.066 ml) and HATU (95 mg) in DMF (2 ml) according to the general method of Example 9 in 59% yield.

MS (ES+) m/z 549 (MNa+, 20%), 527 (MH+, 20%), 321 (100%).

The free base of the title compound was converted to the hydrochloride by dissolving in chloroform/methanol 1:1 and adding 1 equivalent of 1M HCl/diethyl ether then evaporating to dryness. MS as that of free base.

Example 22

3-Chloro-4-({(3R,4S)-4-[(2,3-dihydro[1,4]dioxino[2,3-c]pyridin-7-ylmethyl)amino]-3-hydroxy-1-piperidinyl}methyl)-4,5-dihydro-7H-pyrrolo[3,2,1-de]-1,5-naphthyridin-7-one Hydrochloride

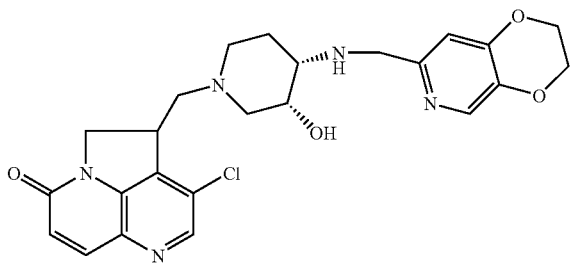

The free base of the title compound was synthesised from racemic 4-{[(3R,4S)-4-amino-3-hydroxy-1-piperidinyl]methyl}-3-chloro-4,5-dihydro-7H-pyrrolo[3,2,1-de]-1,5-naphthyridin-7-one and 2,3-dihydro[1,4]dioxino[2,3-c]pyridine-7-carboxaldehyde (for a synthesis see WO2004058144, Example 2(c)) according to the general method of Example 2(h), in 58% yield MS (ES+) m/z 506 (MNa+, 20%), 484 (MH+, 60%), 150 (100%).

The free base of the title compound was converted to the hydrochloride by dissolving in chloroform and adding 1 equivalent of 1M HCl/diethyl ether then evaporating to dryness. MS as that of free base.

Example 23

3-Chloro-4-[(4-{[(3-oxo-3,4-dihydro-2H-1,4-benzoxazin-6-yl)methyl]amino}-1-piperidinyl)methyl]-4,5-dihydro-7H-pyrrolo[3,2,1-de]-1,5-naphthyridin-7-one Hydrochloride

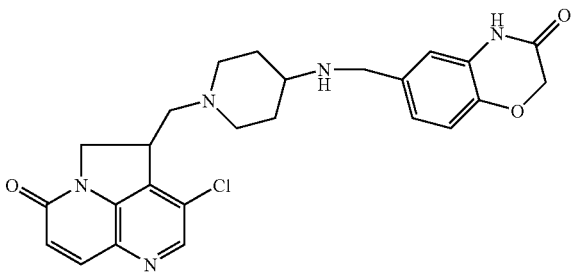

The free base of the title compound was synthesised from 4-[(4-amino-1-piperidinyl)methyl]-3-chloro-4,5-dihydro-7H-pyrrolo[3,2,1-de]-1,5-naphthyridin-7-one and 3-oxo-3,4-dihydro-2H-benzo[1,4]oxazine-6-carboxaldehyde (for a synthesis see WO2002056882, Example 5(b)), according to the general method of Example 2(h), in 69% yield.

MS (ES+) m/z 480 (MH+, 40%), 162 (100%).

The free base of the title compound was converted to the hydrochloride by dissolving in chloroform and adding 1 equivalent of 1M HCl/diethyl ether then evaporating to dryness. MS as that of free base.

Example 24

3-Chloro-4-({4-[(2,3-dihydro[1,4]dioxino[2,3-c]pyridin-7-ylmethyl)amino]-1-piperidinyl}methyl)-4,5-dihydro-7H-pyrrolo[3,2,1-de]-1,5-naphthyridin-7-one Enantiomer 1 Hydrochloride

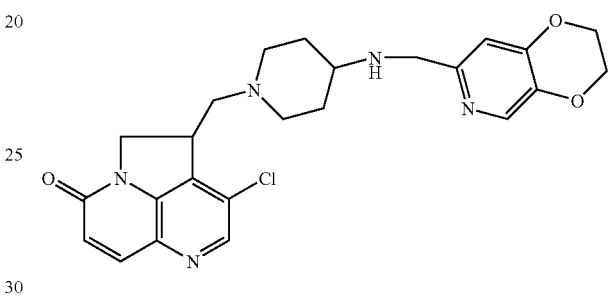

(a) 4-[(4-amino-1-piperidinyl)methyl]-3-chloro-4,5-dihydro-7H-pyrrolo[3,2,1-de]-1,5-naphthyridin-7-one (Enantiomers 1 & 2)

Racemic 4-[(4-amino-1-piperidinyl)methyl]-3-chloro-4,5-dihydro-7H-pyrrolo[3,2,1-de]-1,5-naphthyridin-7-one (5.5 g) was subjected to preparative HPLC on Chiralpak AD. This procedure gave the faster running enantiomer (Enantiomer 1, 2.6 g) in >99% ee and the slower running enantiomer (Enantiomer 2, 2.6 g) in 99% ee.

(b) Title Compound

A mixture of 4-[(4-amino-1-piperidinyl)methyl]-3-chloro-4,5-dihydro-7H-pyrrolo[3,2,1-de]-1,5-naphthyridin-7-one Enantiomer 1 (500 mg) and 2,3-dihydro[1,4]dioxino[2,3-c]pyridine-7-carboxaldehyde (for a synthesis see WO2004058144, Example 2(c)) (260 mg) in chloroform (10 ml)/methanol (10 ml) with 3A molecular sieves under argon was left overnight and then heated at 65° C. for 4 hours. After cooling, the mixture was treated with sodium triacetoxyborohydride (665 mg), stirred overnight and work-up completed according to the general method of Example 2(h) to give free base of the title compound (626 mg containing 3% dichloromethane by weight, 82%).

$^1$H NMR δ (CDCl$_3$) 1.35-1.55 (2H, m), 1.8-2.0 (2H, m), 2.11 (1H, dt), 2.28 (1H, dt), 2.4-2.6 (2H, m), 2.72 (1H, br d), 2.95-3.1 (2H, m), 3.80 (2H, s), 3.95-4.05 (1H, m), 4.25-4.35 (4H, m), 4.35-4.45 (1H, m), 4.55-4.65 (1H, m), 6.83 (1H, s), 6.87 (1H, d, J 10 Hz), 7.88 (1H, d, J 10 Hz), 8.10 (1H, s), 8.38 (1H, s). MS (ES+) m/z 468 (MH+, 30%), 150 (100%).

The free base of the title compound was converted to the hydrochloride by dissolving in chloroform and adding 1 equivalent of 1M HCl/diethyl ether, then evaporating to dryness. MS as that of free base.

Example 25

3-Chloro-4-({4-[(2,3-dihydro[1,4]dioxino[2,3-c]pyridin-7-ylmethyl)amino]-1-piperidinyl}methyl)-4,5-dihydro-7H-pyrrolo[3,2,1-de]-1,5-naphthyridin-7-one Enantiomer 2 Hydrochloride

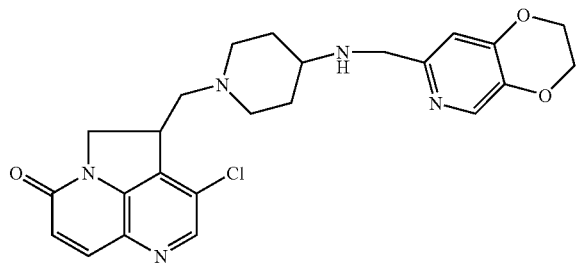

The free base of the title compound was prepared from 4-[(4-amino-1-piperidinyl)methyl]-3-chloro-4,5-dihydro-7H-pyrrolo[3,2,1-de]-1,5-naphthyridin-7-one Enantiomer 2 and 2,3-dihydro[1,4]dioxino[2,3-c]pyridine-7-carboxaldehyde (for a synthesis see WO2004058144, Example 2(c)) according to the general method of Example 24(b) in 84% yield.

$^1$H NMR δ (CDCl$_3$) 1.35-1.55 (2H, m), 1.8-2.0 (2H, m), 2.11 (1H, dt), 2.28 (1H, dt), 2.4-2.6 (2H, m), 2.72 (1H, br d), 2.95-3.1 (2H, m), 3.80 (2H, s), 3.95-4.05 (1H, m), 4×25-4.35 (4H, m), 4.35-4.45 (1H, m), 4.55-4.65 (1H, m), 6.83 (1H, s), 6.87 (1H, d, J 10 Hz), 7.88 (1H, d, J 10 Hz), 8.10 (1H, s), 8.38 (1H, s). MS (ES+) m/z 468 (MH$^+$, 30%), 150 (100%).

The free base of the title compound was converted to the hydrochloride by dissolving in chloroform and adding 1 equivalent of 1M HCl/diethyl ether then evaporating to dryness. MS as that of free base.

Example 26

3-Chloro-4-({4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one Enantiomer 1 Hydrochloride

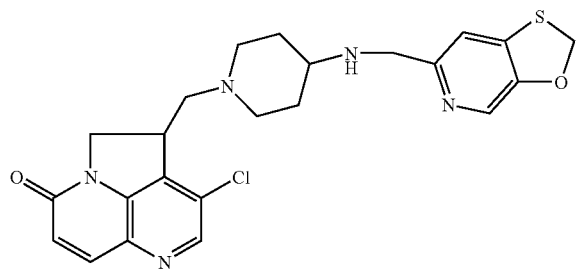

The free base of the title compound was prepared from 4-[(4-amino-1-piperidinyl)methyl]-3-chloro-4,5-dihydro-7H-pyrrolo[3,2,1-de]-1,5-naphthyridin-7-one Enantiomer 1 and [1,3]oxathiolo[5,4-c]pyridine-6-carbaldehyde (for a synthesis see WO2004058144, Example 61) according to the general method of Example 24(b), in 68% yield.

$^1$H NMR δ (CDCl$_3$) 1.35-1.55 (2H, m), 1.8-2.0 (2H, m), 2.11 (1H, dt), 2.28 (1H, dt), 2.4-2.6 (2H, m), 2.73 (1H, br d), 2.95-3.1 (2H, m), 3.83 (2H, s), 3.95-4.05 (1H, m), 4.42 (1H, dd, J 13 and 9 Hz), 4.58 (1H, dd, J 13 and 4 Hz), 5.73 (2H, s), 6.87 (1H, d, J 10 Hz), 7.21 (1H, s), 7.88 (1H, d, J 10 Hz), 8.01 (1H, s), 8.38 (1H, s). MS (ES+) m/z 470 (MH$^+$, 30%), 152 (100%).

The free base of the title compound was converted to the hydrochloride by dissolving in chloroform and adding 1 equivalent of 1M HCl/diethyl ether, then evaporating to dryness. MS as that of free base.

Example 27

3-Chloro-4-({4-[(3,4-dihydro-2H-pyrano[2,3-c]pyridin-6-ylmethyl)amino]-1-piperidinyl}methyl)-4,5-dihydro-7H-pyrrolo[3,2,1-de]-1,5-naphthyridin-7-one Enantiomer 1 Hydrochloride

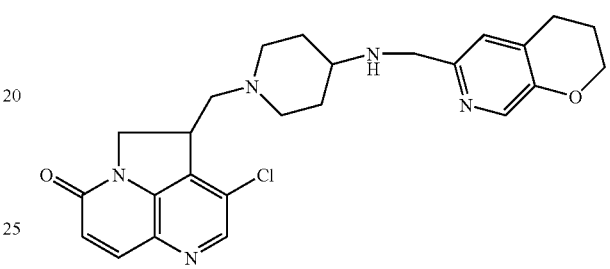

The free base of the title compound was prepared from 4-[(4-amino-1-piperidinyl)methyl]-3-chloro-4,5-dihydro-7H-pyrrolo[3,2,1-de]-1,5-naphthyridin-7-one Enantiomer 1 and 3,4-dihydro-2H-pyrano[2,3-c]pyridine-6-carbaldehyde (for a synthesis see WO2004058144, Example 126(e)) according to the general method of Example 24(b) in 72% yield.

$^1$H NMR δ (CDCl$_3$) 1.35-1.55 (2H, m), 1.8-1.95 (2H, m), 1.95-2.05 (2H, m), 2.11 (1H, dt), 2.28 (1H, dt), 2.47 (1H, dd), 2.5-2.6 (1H, m), 2.7-2.8 (3H, m), 2.95-3.1 (2H, m), 3.80 (2H, s), 3.95-4.05 (1H, m), 4.1-4.2 (2H, m), 4.42 (1H, dd, J 13 and 9 Hz), 4.58 (1H, dd, J 13 and 4 Hz), 6.87 (1H, d, J 10 Hz), 6.99 (1H, s), 7.88 (1H, d, J 10 Hz), 8.09 (1H, s), 8.38 (1H, s). MS (APCI+) m/z 466 (MH$^+$, 30%), 219 (100%).

The free base of the title compound was converted to the hydrochloride by dissolving in chloroform and adding 1 equivalent of 1M HCl/diethyl ether, then evaporating to dryness. MS as that of free base.

Example 28

3-Chloro-4-[(4-{[(3-oxo-3,4-dihydro-2H-pyrido[3,2-b][1,4]oxazin-6-yl)methyl]amino}-1-piperidinyl)methyl]-4,5-dihydro-7H-pyrrolo[3,2,1-de]-1,5-naphthyridin-7-one Enantiomer 1 Hydrochloride

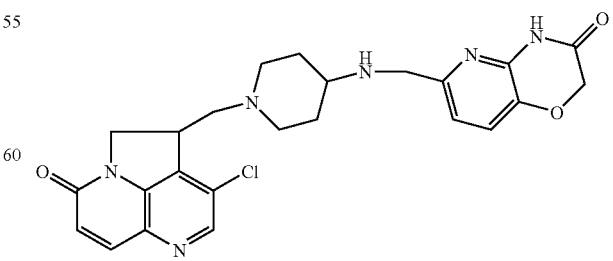

The free base of the title compound was prepared from 4-[(4-amino-1-piperidinyl)methyl]-3-chloro-4,5-dihydro- 7H-pyrrolo[3,2,1-de]-1,5-naphthyridin-7-one Enantiomer 1 and 3-oxo-3,4-dihydro-2H-pyrido[3,2-b][1,4]oxazine-6-carboxaldehyde (for a synthesis see WO2003087098, Example 31(e)) according to the general method of Example 24(b) in 52% yield.

$^1$H NMR δ (CDCl$_3$) 1.35-1.55 (2H, m), 1.8-2.0 (2H, m), 2.11 (1H, dt), 2.28 (1H, dt), 2.4-2.6 (2H, m), 2.74 (1H, br d), 2.95-3.1 (2H, m), 3.83 (2H, s), 3.95-4.05 (1H, m), 4.42 (1H, dd, J 13 and 9 Hz), 4.57 (1H, dd, J 13 and 4 Hz), 4.64 (2H, s), 6.87 (1H, d, J 10 Hz), 6.94 (1H, d, J 8 Hz), 7.21 (1H, d, J 8 Hz), 7.89 (1H, d, J 10 Hz), 8.38 (1H, s). MS (ES+) m/z 481 (MH$^+$, 30%), 163 (100%).

The free base of the title compound was converted to the hydrochloride by dissolving in chloroform and adding 1 equivalent of 1M HCl/diethyl ether, then evaporating to dryness. MS as that of free base.

Example 29

3-Chloro-4-[(4-{[(3-oxo-3,4-dihydro-2H-1,4-benzothiazin-6-yl)methyl]amino}-1-piperidinyl)methyl]-4,5-dihydro-7H-pyrrolo[3,2,1-de]-1,5-naphthyridin-7-one Enantiomer 1 Hydrochloride

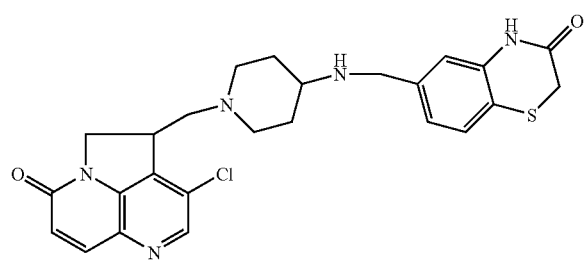

The free base of the title compound was prepared from 4-[(4-amino-1-piperidinyl)methyl]-3-chloro-4,5-dihydro-7H-pyrrolo[3,2,1-de]-1,5-naphthyridin-7-one Enantiomer 1 and 3-oxo-3,4-dihydro-2H-benzo[1,4]thiazine-6-carboxaldehyde (for a synthesis see WO2002056882, Example 6(c)) according to the general method of Example 24(b) in 53% yield.

$^1$H NMR δ (CDCl$_3$) 1.35-1.55 (2H, m), 1.8-2.0 (2H, m), 2.11 (1H, dt), 2.28 (1H, dt), 2.4-2.6 (2H, m), 2.73 (1H, br d), 2.95-3.1 (2H, m), 3.42 (2H, s), 3.77 (2H, s), 3.95-4.05 (1H, m), 4.42 (1H, dd, J 13 and 9 Hz), 4.59 (1H, dd, J 13 and 4 Hz), 6.8-6.9 (2H, m), 6.98 (1H, dd, J 8 and 1 Hz), 7.26 (1H, d, J 8 Hz), 7.89 (1H, d, J 10 Hz), 8.04 (1H, br s), 8.38 (1H, s). MS (APCI+) m/z 518 (MNa$^+$), 496 (MH$^+$, 10%), 219 (100%).

The free base of the title compound was converted to the hydrochloride by dissolving in chloroform and adding 1 equivalent of 1M HCl/diethyl ether then evaporating to dryness. MS as that of free base.

Example 30

3-Chloro-4-[(4-{[(2-oxo-2,3-dihydro-1H-pyrido[2,3-b][1,4]thiazin-7-yl)methyl]amino}-1-piperidinyl)methyl]-4,5-dihydro-7H-pyrrolo[3,2,1-de]-1,5-naphthyridin-7-one Enantiomer 1 Hydrochloride

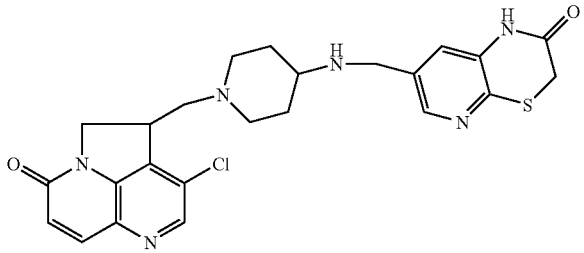

The free base of the title compound was prepared from 4-[(4-amino-1-piperidinyl)methyl]-3-chloro-4,5-dihydro-7H-pyrrolo[3,2,1-de]-1,5-naphthyridin-7-one Enantiomer 1 and 2-oxo-2,3-dihydro-1H-pyrido[2,3-b][1,4]thiazine-7-carbaldehyde (for a synthesis see WO2004058144 Example 48(e)) according to the general method of Example 24(b) in 49% yield.

$^1$H NMR δ (CDCl$_3$/CD$_3$OD) 1.35-1.55 (2H, m), 1.8-2.0 (2H, m), 2.11 (1H, dt), 2.28 (1H, dt), 2.4-2.6 (2H, m), 2.76 (1H, br d), 2.95-3.1 (2H, m), 3.55 (2H, s), 3.77 (2H, s), 3.95-4.05 (1H, m), 4.45 (1H, dd, J 13 and 9 Hz), 4.56 (1H, dd, J 13 and 4 Hz), 6.89 (1H, d, J 10 Hz), 7.21 (1H, d, J 1.5 Hz), 7.93 (1H, d, J 10 Hz), 8.06 (1H, d, J 1.5 Hz), 8.40 (1H, s). MS (APCI+) m/z 497 (MH$^+$, 5%), 226 (100%).

The free base of the title compound was converted to the hydrochloride by dissolving in chloroform/methanol and adding 1 equivalent of 1M HCl/diethyl ether, then evaporating to dryness. MS as that of free base.

Example 31

7-[({(3R,4S)-1-[(3-Chloro-7-oxo-4,5-dihydro-7H-pyrrolo[3,2,1-de]-1,5-naphthyridin-4-yl)methyl]-3-hydroxy-4-piperidinyl}amino)methyl]-2,3-dihydro-1,4-benzodioxin-5-carbonitrile Diastereomer 1 Hydrochloride

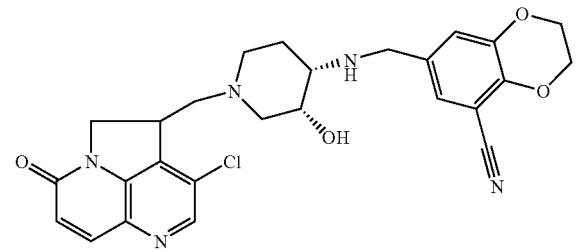

(a) 3-Bromo-4-hydroxy-5-methoxybenzaldehyde

To a solution of vanillin (30.40 g, 0.20 mol) in glacial acetic acid (200 ml) was added bromine (46.79 g, 0.29 mol) in glacial acetic acid (20 ml) at 100 over a period of 1 h. Additional acetic acid (100 ml) was added to the thickening mixture and the reaction was stirred for 24 h at ambient temperature. The reaction was diluted with ice-water (300 ml) and then the precipitate was filtered and washed with water and dried in vacuo to give the desired compound (40.69 g, 89%).

MS (ES) m/z 230 (M+H)+.

(b) 3-Bromo-4,5-dihydroxybenzaldehyde

To a solution of 3-bromo-4-hydroxy-5-methoxybenzaldehyde (12.1 g, 0.52 mol) in dichloromethane (200 ml) was added 1.0 M boron tribromide in dichloromethane (2.2 eq, 115 ml) at 0°. The reaction was stirred at 0° for 20 min, then at ambient temperature for 2.5 h. The reaction was then cooled to 0°, and quenched by the slow addition of methanol. The solvents were removed under reduced pressure and the trimethyl borate was removed by azeotropation with added methanol. Drying in vacuo yielded the desired product (11.51 g, 100%).

MS (ES) m/z 217 (M+H)+.

(c) 8-Bromo-2,3-dihydro-1,4-benzodioxin-6-carbaldehyde

To a solution of 3-bromo-4,5-dihydroxybenzaldehyde (11.5 g, 0.52 mol) in dimethylformamide (220 ml) was added cesium carbonate (50.7 g, 1.56 mol). The mixture was stirred at ambient temperature for 30 min, then 1,2-dibromoethane (12.76 g, 0.68 mol) were added. After heating at 80° for 4 h, the dimethylformamide was removed under reduced pressure. The residue was partitioned between water and ethyl acetate, and the organic layer was washed with brine and dried. The crude product was purified by flash column chromatography (silica gel, 4:1 hexane:ethyl acetate) to give the desired compound as an off-white solid (9.57 g, 75%).

MS (ES) m/z 243 (M+H)+.

(d) 8-Cyano-2,3-dihydro-1,4-benzodioxin-6-carbaldehyde

To a solution of 8-bromo-2,3-dihydro-1,4-benzodioxin-6-carbaldehyde (4.60 g, 0.189 mol) in dimethylacetamide (45 mL) was added copper(I) cyanide (1.82 g, 0.203 mol). The reaction was refluxed for 4 h, and then concentrated under reduced pressure. The residue was partitioned between ~1:1 water:ethyl acetate; the inorganic material was removed by filtration and washed well with warm ethyl acetate. The combined ethyl acetate layer and washings were washed with water, brine and dried. The crude product was triturated with cold ethyl acetate and chilled. The solid was filtered, washed with cold 8:1 hexane:ethyl acetate and vacuum dried to give a white solid (2.29 g). An additional 0.656 g was obtained from the concentrated filtrate by flash column chromatography (silica gel, 4-1 and 2:1 hexane:ethyl acetate gradient) for a total yield of 82%.

MS (ES) m/z 190 (M+H)+.

(e) Title Compound

The free base of the title compound was prepared from 4-{[(3R,4S)-4-amino-3-hydroxy-1-piperidinyl]methyl}-3-chloro-4,5-dihydro-7H-pyrrolo[3,2,1-de]-1,5-naphthyridin-7-one Diastereomer 1 and 8-cyano-2,3-dihydro-1,4-benzodioxin-6-carbaldehyde according to the general method of Example 24(b), (53%).

1H NMR δ (CDCl3) 1.6-1.8 (2H, m), 2.2-2.4 (2H, m), 2.45-2.60 (2H, m), 2.73 (1H, broad d), 3.05-3.2 (2H, m), 3.73 (2H, ABq), 3.88 (1H, broad s), 3.95-4.05 (1H, m), 4.25-4.40 (4H, m), 4.4-4.6 (2H, m), 6.88 (1H, d, J 10 Hz), 7.10-7.15 (2H, m), 7.89 (1H, d, J 10 Hz), 8.39 (1H, s). MS (ES+) m/z 508 (MH+, 40%), 174 (100%).

The free base of the title compound was converted to the hydrochloride by dissolving in chloroform and adding 1 equivalent of 1M HCl/diethyl ether, then evaporating to dryness. MS as that of free base.

Example 32

3-Chloro-4-({(3R,4S)-3-hydroxy-4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one Diastereomer 1 hydrochloride

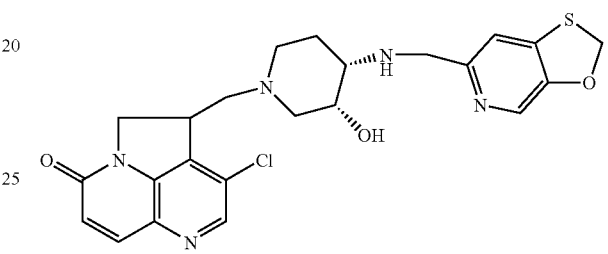

The free base of the title compound was prepared from 4-{[(3R,4S)-4-amino-3-hydroxy-1-piperidinyl]methyl}-3-chloro-4,5-dihydro-7H-pyrrolo[3,2,1-de]-1,5-naphthyridin-7-one Diastereomer 1 and [1,3]oxathiolo[5,4-c]pyridine-6-carbaldehyde (for a synthesis see WO2004058144, Example 61) according to the general method of Example 24(b), (61

1H NMR δ (CDCl3) 1.6-1.8 (2H, m), 2.2-2.4 (2H, m), 2.51 (1H, dd, J 13 and 11 Hz), 2.55-2.65 (1H, m), 2.65-2.75 (1H, m), 3.05-3.15 (2H, m), 3.87 (3H, s, broad at base), 3.95-4.05 (1H, m), 4.46 (1H, dd, J 13 and 8 Hz), 4.53 (1H, dd, J 13 and 4 Hz), 5.74 (2H, s), 6.87 (1H, d, J 10 Hz), 7.23 (1H, s), 7.89 (1H, d, J 110 Hz), 8.01 (1H, s), 8.39 (1H, s). MS (ES+) m/z 486 (MH+, 100%), 280 (100%).

The free base of the title compound was converted to the hydrochloride by dissolving in chloroform and adding 1 equivalent of 1M HCl/diethyl ether, then evaporating to dryness. MS as that of free base.

Example 33

3-Chloro-4-({(3R,4S)-4-[(3,4-dihydro-2H-pyrano[2,3-c]pyridin-6-ylmethyl)amino]-3-hydroxy-1-piperidinyl}methyl)-4,5-dihydro-7H-pyrrolo[3,2,1-de]-1,5-naphthyridin-7-one Hydrochloride

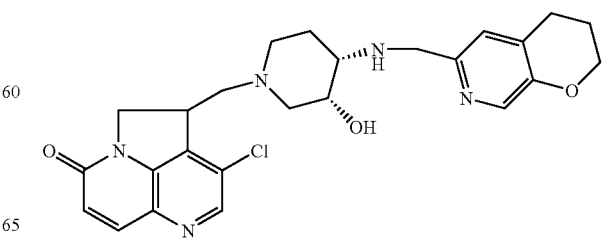

The free base of the title compound was prepared from racemic 4-{[(3R,4S)-4-amino-3-hydroxy-1-piperidinyl]methyl}-3-chloro-4,5-dihydro-7H-pyrrolo[3,2,1-de]-1,5-naphthyridin-7-one and 3,4-dihydro-2H-pyrano[2,3-c]pyridine-6-carbaldehyde (for a synthesis see WO2004058144, Example 126(e)) according to the general method of Example 24(b), chromatographing with dichloromethane/methanol/0.88 ammonia 95:5:0.5, in 50% yield.

MS (ES+) m/z 482 (MH+, 20%), 242 (100%).

The free base of the title compound was converted to the hydrochloride by dissolving in chloroform and adding 1 equivalent of 1M HCl/diethyl ether, then evaporating to dryness. MS as that of free base.

Example 34

3-Chloro-4-({4-[(2,3-dihydro[1,4]oxathiino[2,3-c]pyridin-7-ylmethyl)amino]-1-piperidinyl}methyl)-4,5-dihydro-7H-pyrrolo[3,2,1-de]-1,5-naphthyridin-7-one Enantiomer 1 Hydrochloride

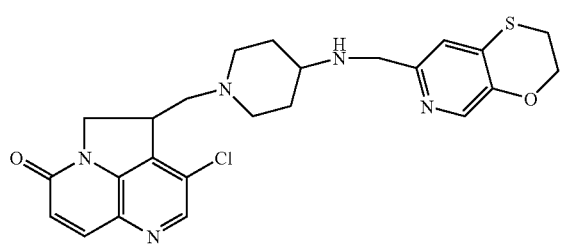

The free base of the title compound was prepared from 4-[(4-amino-1-piperidinyl)methyl]-3-chloro-4,5-dihydro-7H-pyrrolo[3,2,1-de]-1,5-naphthyridin-7-one Enantiomer 1 and 2,3-dihydro[1,4]oxathiino[2,3-c]pyridine-7-carbaldehyde (for a synthesis see WO2004058144, Example 60) according to the general method of Example 24(b), chromatographing with dichloromethane/methanol/0.88 ammonia 95:5:0.5, in 78% yield.

$^1$H NMR δ (CDCl$_3$) 1.35-1.5 (2H, m), 1.8-2.0 (2H, m), 2.11 (1H, dt), 2.28 (1H, dt), 2.40-2.60 (2H, m), 2.73 (1H, broad d), 2.95-3.05 (2H, m), 3.1-3.2 (2H, m), 3.80 (2H, s), 3.95-4.05 (1H, m), 4.35-4.45 (3H, m), 4.58 (1H, dd, J 13 and 4 Hz), 6.87 (1H, d, J 10 Hz), 7.01 (1H, s), 7.88 (1H, d, J 10 Hz), 8.03 (1H, s), 8.38 (1H, s). MS (ES+) m/z 484 (MH+, 20%), 243 (100%).

The free base of the title compound was converted to the hydrochloride by dissolving in dichloromethane and adding 1 equivalent of 1M HCl/diethyl ether, then evaporating to dryness. MS as that of free base.

Example 35

3-Chloro-4-({4-[(2,3-dihydrofuro[2,3-c]pyridin-5-ylmethyl)amino]-1-piperidinyl}methyl)-4,5-dihydro-7H-pyrrolo[3,2,1-de]-1,5-naphthyridin-7-one Enantiomer 1 Hydrochloride

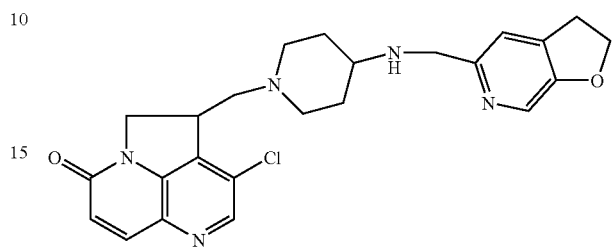

The free base of the title compound was prepared from 4-[(4-amino-1-piperidinyl)methyl]-3-chloro-4,5-dihydro-7H-pyrrolo[3,2,1-de]-1,5-naphthyridin-7-one Enantiomer 1 and 2,3-dihydrofuro[2,3-c]pyridine-5-carbaldehyde according to the general method of Example 24(b), chromatographing with dichloromethane/methanol/0.88 ammonia 95:5:0.5, in 68% yield.

MS (ES+) m/z 452 (MH+, 60%), 227 (100%).

The free base of the title compound was converted to the hydrochloride by dissolving in chloroform and adding 1 equivalent of 1M HCl/diethyl ether, then evaporating to dryness. MS as that of free base.

Example 36

(4R)-4-({4-[(2,3-Dihydro[1,4]dioxino[2,3-c]pyridin-7-ylmethyl)amino]-1-piperidinyl}methyl)-3-fluoro-4,5-dihydro-7H-pyrrolo[3,2,1-de]-1,5-naphthyridin-7-one Enantiomer 1 Hydrochloride

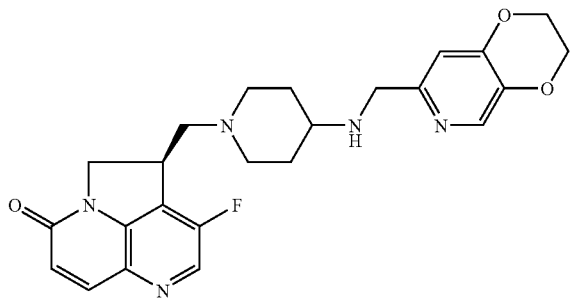

(a) 4-[(4-Amino-1-piperidinyl)methyl]-3-fluoro-4,5-dihydro-7H-pyrrolo[3,2,1-de]-1,5-naphthyridin-7-one Enantiomers 1 and 2

Racemic 4-[(4-amino-1-piperidinyl)methyl]-3-fluoro-4,5-dihydro-7H-pyrrolo[3,2,1-de]-1,5-naphthyridin-7-one (7.8 g) was subjected to preparative HPLC on Chiralpak AS. This procedure gave the faster running enantiomer (Enantiomer 1, 3.8 g) in >99% ee and the slower running enantiomer (Enantiomer 2, 3.9 g) in 98.6% ee.

(b) 4-Bromo-N-(1-{[(4S)-3-fluoro-7-oxo-4,5-dihydro-7H-pyrrolo[3,2,1-de]-1,5-naphthyridin-4-yl]methyl}-4-piperidinyl)benzamide, Methanol Solvate (2:1)

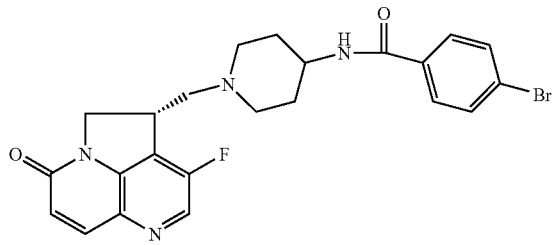

A solution of 4-[(4-amino-1-piperidinyl)methyl]-3-fluoro-4,5-dihydro-7H-pyrrolo[3,2,1-de]-1,5-naphthyridin-7-one Enantiomer 2 (200 mg, 0.664 mmol) in dichloromethane (5 ml) was treated with triethylamine (0.139 ml, 1 mmol), ice-cooled under argon and treated with 4-bromobenzoyl chloride (150 mg, 0.682 mmol). The solution was shaken with excess aqueous sodium bicarbonate solution, separated and the aqueous re-extracted twice with 15% methanol/dichloromethane. The combined organic extracts were dried and evaporated and the residue chromatographed using dichloromethane/methanol/0.88 ammonia 96:4:0.4 to give 4-bromo-N-(1-{[(4S)-3-fluoro-7-oxo-4,5-dihydro-7H-pyrrolo[3,2,1-de]-1,5-naphthyridin-4-yl]methyl}-4-piperidinyl)benzamide (280 mg, 87%).

MS (ES+) m/z 485 and 487 (MH+, 40%), 295 and 297 (100%).

Crystallisation from methanol gave the title compound, suitable for X-ray crystallographic analysis.

The crystal and molecular structures of the title compound were determined from 3-dimensional X-ray diffraction data. The study confirmed the atomic connectivity, with derived bond distances and angles being fully consistent with the proposed structure. The structure determination also allowed the unambiguous assignment of absolute configuration (4S).

(c) Title Compound

The free base of the title compound was prepared from (4R)-4-[(4-amino-1-piperidinyl)methyl]-3-fluoro-4,5-dihydro-7H-pyrrolo[3,2,1-de]-1,5-naphthyridin-7-one (Enantiomer 1) and 2,3-dihydro[1,4]dioxino[2,3-c]pyridine-7-carboxaldehyde (for a synthesis see WO2004058144, Example 2(c)) according to the general method of Example 24(b), chromatographing with dichloromethane/methanol/0.88 ammonia 95:5:0.5, in 81% yield.

$^1$H NMR δ (CDCl$_3$) 1.35-1.5 (2H, m), 1.8-2.0 (2H, m), 2.11 (1H, dt), 2.24 (1H, dt), 2.50-2.60 (2H, m), 2.75-2.90 (2H, m), 2.96 (1H, broad d), 3.80 (2H, s), 4.05-4.15 (1H, m), 4.25-4.35 (4H, m), 4.40-4.55 (2H, m), 6.80-6.90 (2H, m), 7.88 (1H, d, J 10 Hz), 8.11 (1H, s), 8.32 (1H, s). MS (ES+) m/z 452 (MH+, 40%), 150 (100%).

The free base of the title compound was converted to the hydrochloride by dissolving in dichloromethane and adding 1 equivalent of 1M HCl/diethyl ether, then evaporating to dryness. MS as that of free base.

Example 37

(4R)-4-({4-[(3,4-Dihydro-2H-pyrano[2,3-c]pyridin-6-ylmethyl)amino]-1-piperidinyl}methyl)-3-fluoro-4,5-dihydro-7H-pyrrolo[3,2,1-de]-1,5-naphthyridin-7-one Hydrochloride

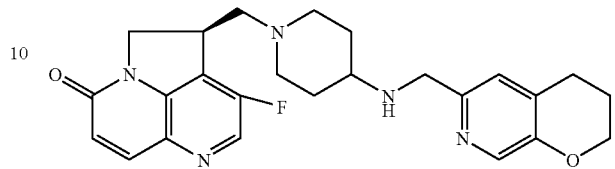

(4R)-4-[(4-amino-1-piperidinyl)methyl]-3-fluoro-4,5-dihydro-7H-pyrrolo[3,2,1-de]-1,5-naphthyridin-7-one Enantiomer 1 (200 mg, 0.66 mmol) and 3,4-dihydro-2H-pyrano[2,3-c]pyridine-6-carbaldehyde (for a synthesis see WO2004058144, Example 126(e)) (107 mg, 0.66 mmol) were dissolved in methanol (30 ml) and acetic acid (3 ml). The solution was treated with (polystyrylmethyl)trimethylammonium cyanoborohydride (Novabiochem) (4.1 mmol/g, 0.9 g), and the mixture stirred at room temperature overnight. The mixture was filtered, and the filtrate evaporated. The residue was subjected to column chromatography on silica gel using a dichloromethane/2M methanolic ammonia gradient to provide the free base of the title compound (0.188 g, 64%).

$^1$H NMR δ (CDCl$_3$) 1.45-1.55 (2H, m), 1.85-2.06 (4H, m), 2.11 (1H, dt), 2.24 (1H, dt), 2.50-2.63 (2H, m), 2.75-2.88 (4H, m), 2.96 (1H, broad d), 3.85 (2H, s), 4.05-4.20 (1H, m), 4.25-4.35 (2H, m), 4.46-4.50 (2H, m), 6.83 (2H, d, J 10 Hz), 7.00 (1H, s), 7.88 (1H, d, J 10 Hz), 8.08 (1H, s), 8.32 (1H, s). MS (ES+) m/z 472 (MNa+, 20%), 450 (MH+, 40%), 148 (100%).

The free base of the title compound was converted to the hydrochloride by dissolving in dichloromethane and adding 1 equivalent of 1M HCl/diethyl ether then evaporating to dryness. MS as that of free base.

Example 38

(4R)-3-Fluoro-4-({4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one Enantiomer 1 Hydrochloride

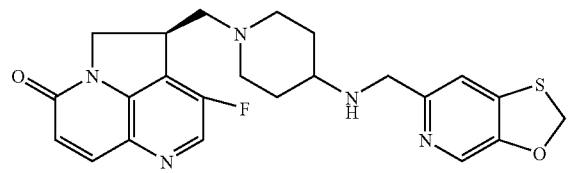

The free base of the title compound was prepared from (4R)-4-[(4-amino-1-piperidinyl)methyl]-3-fluoro-4,5-dihydro-7H-pyrrolo[3,2,1-de]-1,5-naphthyridin-7-one Enantiomer 1 and [1,3]oxathiolo[5,4-c]pyridine-6-carbaldehyde (for a synthesis see WO2004058144, Example 61) in 84% yield according to the general method of Example 2(h), except that the reaction was stirred for 1 hr after the addition of sodium triacetoxyborohydride.

$^1$H NMR (CDCl$_3$) 1.46-1.51 (2H, m), 1.86-1.93 (2H, m), 2.09-2.14 (1H, m), 2.21-2.27 (1H, m), 2.50-2.56 (2H, m), 2.81-2.95 (2H, m), 2.97-2.98 (1H, broad d), 3.83 (2H, s), 4.04-4.11 (1H, m), 4.48 (2H, d, J 16 Hz), 5.74 (2H, s), 6.83 (1H, d, J 10 Hz), 7.21 (1H, s), 7.89 (1H, d, J 10 Hz), 8.01 (1H, s), 8.32 (1H, s).

MS (ES+) m/z 454 (MH+100%).

The free base of the title compound was converted to the hydrochloride by dissolving in methanol and adding 1 equivalent of 1M HCl/diethyl ether then evaporating to dryness. MS as that of free base.

Example 39

(4R)-3-Fluoro-4-[(4-{[(3-oxo-3,4-dihydro-2H-pyrido[3,2-b][1,4]oxazin-6-yl)methyl]amino}-1-piperidinyl)methyl]-4,5-dihydro-7H-pyrrolo[3,2,1-de]-1,5-naphthyridin-7-one Enantiomer 1 Hydrochloride

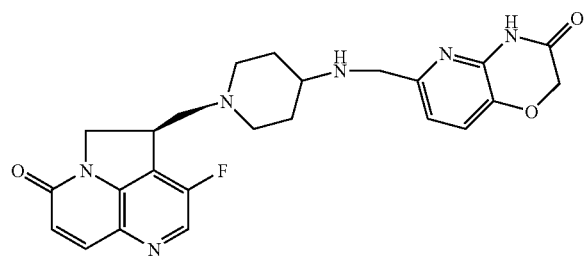

The free base of the title compound was prepared from (4R)-4-[(4-amino-1-piperidinyl)methyl]-3-fluoro-4,5-dihydro-7H-pyrrolo[3,2,1-de]-1,5-naphthyridin-7-one Enantiomer 1 and 3-oxo-3,4-dihydro-2H-pyrido[3,2-b][1,4]oxazine-6-carboxaldehyde (for a synthesis see WO2003087098, Example 31(e)) according to the general method of Example 24(b), (82%).

$^1$H NMR δ (CDCl$_3$) 1.35-1.55 (2H, m), 1.8-2.0 (2H, m), 2.12 (1H, dt), 2.24 (1H, dt), 2.5-2.6 (2H, m), 2.8-2.9 (2H, m), 2.9-3.0 (1H, m), 3.83 (2H, s), 4.0-4.1 (1H, m), 4.4-4.5 (2H, m), 4.64 (2H, s), 6.83 (1H, d, J 10 Hz), 6.94 (1H, d, J 8 Hz), 7.21 (1H, d, J 8 Hz), 7.89 (1H, d, J 10 Hz), 8.33 (1H, d, J 1 Hz).

MS (ES+) m/z 465 (MH$^+$, 100%).

The free base of the title compound was converted to the hydrochloride by dissolving in chloroform and adding 1 equivalent of 1M HCl/diethyl ether, then evaporating to dryness. MS as that of free base.

Example 40

(4R)-3-Fluoro-4-[(4-{[(3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one Enantiomer 1 Hydrochloride

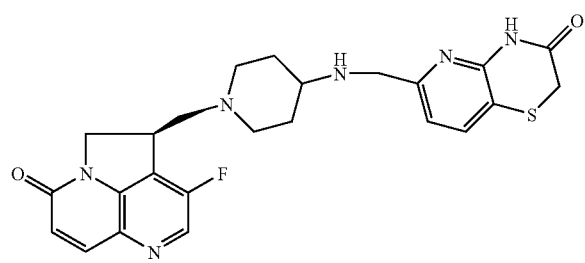

The free base of the title compound was prepared from (4R)-4-[(4-amino-1-piperidinyl)methyl]-3-fluoro-4,5-dihydro-7H-pyrrolo[3,2,1-de]-1,5-naphthyridin-7-one Enantiomer 1 and 3-oxo-3,4-dihydro-2H-pyrido[3,2-b][1,4]thiazine-6-carboxaldehyde (for a synthesis see WO2003087098, Example 301 (d)) according to the general method of Example 24(b), chromatographing with dichloromethane/methanol/0.88 ammonia 93:7:0.7 (80%).

$^1$H NMR δ (CDCl$_3$) 1.4-1.55 (2H, m), 1.8-2.0 (2H, m), 2.12 (1H, dt), 2.24 (1H, dt), 2.50-2.60 (2H, m), 2.75-2.90 (2H, m), 2.98 (1H, broad d), 3.48 (2H, s), 3.85 (2H, s), 4.05-4.15 (1H, m), 4.40-4.55 (2H, m), 6.83 (1H, d, J 10 Hz), 6.99 (1H, d, J 8 Hz), 7.58 (1H, d, J 8 Hz), 7.89 (1H, d, J 10 Hz), 8.26 (1H, broad s), 8.33 (1H, d, J 1 Hz).

MS (ES+) m/z 481 (MH$^+$, 100%).

The free base of the title compound was converted to the hydrochloride by dissolving in chloroform and adding 1 equivalent of 1M HCl/diethyl ether, then evaporating to dryness. MS as that of free base.

Example 41

(4S)-4-({4-[(2,3-Dihydro[1,4]dioxino[2,3-c]pyridin-7-ylmethyl)amino]-1-piperidinyl}methyl)-3-fluoro-4,5-dihydro-7H-pyrrolo[3,2,1-de]-1,5-naphthyridin-7-one Enantiomer 2 Hydrochloride

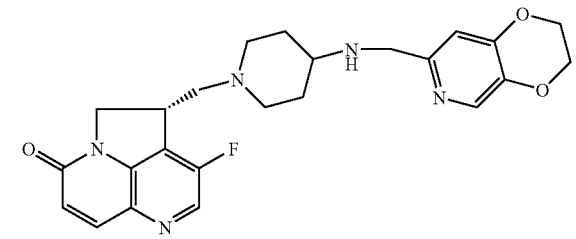

The free base of the title compound was prepared from (4S)-4-[(4-amino-1-piperidinyl)methyl]-3-fluoro-4,5-dihydro-7H-pyrrolo[3,2,1-de]-1,5-naphthyridin-7-one Enantiomer 2 and 2,3-dihydro[1,4]dioxino[2,3-c]pyridine-7-carboxaldehyde (for a synthesis see WO2004058144, Example 2(c)) according to the general method of Example 24(b), (77%).

$^1$H NMR δ (CDCl$_3$) 1.35-1.5 (2H, m), 1.8-2.0 (2H, m), 2.11 (1H, dt), 2.24 (1H, dt), 2.50-2.60 (2H, m), 2.75-2.90 (2H, m), 2.96 (1H, broad d), 3.80 (2H, s), 4.05-4.15 (1H, m), 4.25-4.35 (4H, m), 4.40-4.55 (2H, m), 6.80-6.90 (2H, m), 7.88 (1H, d, J 10 Hz), 8.11 (1H, s), 8.32 (1H, s).

MS (ES+) m/z 452 (MH$^+$, 40%), 150 (100%).

The free base of the title compound was converted to the hydrochloride by dissolving in dichloromethane and adding 1 equivalent of 1M HCl/diethyl ether, then evaporating to dryness. MS as that of free base.

Example 42

(4R)-4-({4-[(2,3-Dihydro[1,4]oxathiino[2,3-c]pyridin-7-ylmethyl)amino]-1-piperidinyl}methyl)-3-fluoro-4,5-dihydro-7H-pyrrolo[3,2,1-de]-1,5-naphthyridin-7-one Enantiomer 1 Hydrochloride

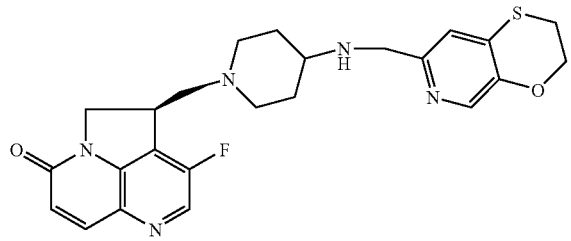

The free base of the title compound was prepared from (4R)-4-[(4-amino-1-piperidinyl)methyl]-3-fluoro-4,5-dihydro-7H-pyrrolo[3,2,1-de]-1,5-naphthyridin-7-one Enantiomer 1 and 2,3-dihydro[1,4]oxathiino[2,3-c]pyridine-7-carbaldehyde (for a synthesis see WO2004058144, Example 60) in 50% yield according to the general method of Example 2(h), except that the reaction was stirred for 1 hr after the addition of sodium triacetoxyborohydride.

$^1$H NMR CDCl$_3$) 1.42-1.51 (2H, m), 1.86-1.93 (2H, m), 2.09-2.13 (1H, m), 2.20-2.27 (1H, m), 2.45-2.56 (2H, m), 2.79-2.87 (2H, m), 2.85-2.98 (1H, broad d), 3.16-3.18 (2H, m), 3.79 (2H, s), 4.05-4.09 (1H, m), 4.3-4.41 (2H, m), 4.42-4.48 (2H, m), 6.83 (1H, d, J 10 Hz), 7.00 (1H, s), 7.89 (1H, d, J 10 Hz), 8.10 (1H, s), 8.32 (1H, s).

MS (ES+) m/z 468 (MH+50%).

The free base of the title compound was converted to the hydrochloride by dissolving in methanol and adding 1 equivalent of 1M HCl/diethyl ether then evaporating to dryness. MS as that of free base.

Example 43

(4R)-4-({4-[(2,3-dihydrofuro[2,3-c]pyridin-5-ylmethyl)amino]-1-piperidinyl}methyl)-3-fluoro-4,5-dihydro-7H-pyrrolo[3,2,1-de]-1,5-naphthyridin-7-one Enantiomer 1 Hydrochloride

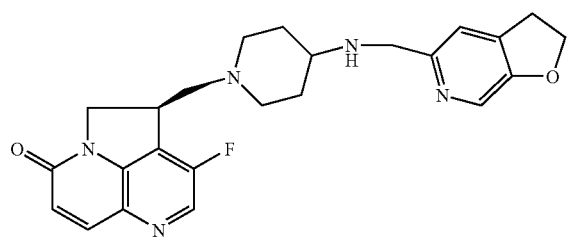

(a) {5-({[4-(Methyloxy)phenyl]methyl}oxy)-4-[(trimethylsilyl)ethynyl]-2-pyridinyl}methyl Acetate

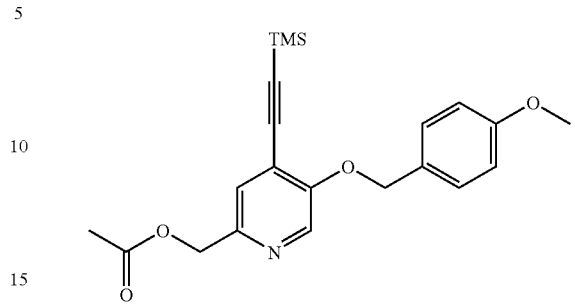

(5-({[4-(Methyloxy)phenyl]methyl}oxy)-4-{[(trifluoromethyl)sulfonyl]oxy}-2-pyridinyl)methyl acetate (10 g, 23 mmol) (for a synthesis see WO2004058144, Example 60(d)) was dissolved in acetonitrile (400 ml) and triethylamine (65 ml) and treated with trimethylsilyl acetylene (10 ml, 69 mmol). The mixture was then degassed several times and put under an atmosphere of argon. Copper(I) iodide (0.44 g, 2.3 mmol) and bis(triphenylphosphine)palladium(II) chloride (0.645 g, 0.9 mmol) was added and the mixture heated at 45° C. for 18 h. The mixture was allowed to cool and filtered. The filtrate was concentrated in vacuo and the residue partitioned between ethyl acetate and water. The organic layer was dried then evaporated to dryness. Chromatography on silica gel eluting with 40-60 petrol and ethyl acetate gradient provided the desired compound (8.45 g, 96%).

MS (APCI+) m/z 384 (MH+, 100%).

(b) {5-Hydroxy-4-[(trimethylsilyl)ethynyl]-2-pyridinyl}methyl Acetate

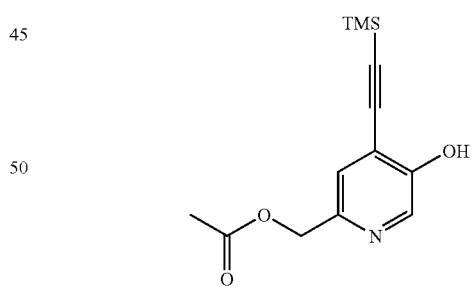

{5-({[4-(Methyloxy)phenyl]methyl}oxy)-4-[(trimethylsilyl)ethynyl]-2-pyridinyl}methyl acetate (8.45 g, 22 mmol) was dissolved in dichloromethane (70 ml) and treated with triethylsilane (3.3 ml) and trifluoroacetic acid (9.4 ml) at ambient temperature for 18 h. The mixture was evaporated to dryness and chromatographed on silica gel eluting with methanol and dichloromethane gradient to provide the desired compound as the TFA salt (8.3 g, 100%).

MS (APCI+) m/z 264 (MH+, 40%).

(c) Mixture of furo[2,3-c]pyridin-5-ylmethyl acetate and [2-(trimethylsilyl)furo[2,3-c]pyridin-5-yl]methyl Acetate

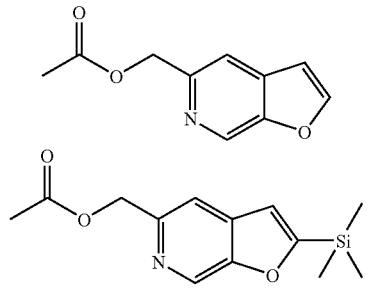

{5-Hydroxy-4-[(trimethylsilyl)ethynyl]-2-pyridinyl}methyl acetate (8.3 g, 22 mmol) was dissolved in pyridine (200 ml) and treated with copper(I) iodide (5.2 g, 27 mmol) then heated under reflux for 18 h. The mixture was allowed to cool then evaporated to dryness. The residue was partitioned between water and ethyl acetate then filtered through kieselguhr. The organic layer was separated washed with more water then saturated brine solution then dried. Chromatography on silica gel eluting with 40-60 petrol and ethyl acetate gradient provided the two title compounds, (1.15 g, 27%) of furo[2,3-c]pyridin-5-ylmethyl acetate and (1.3 g, 22%) of [2-(trimethylsilyl)furo[2,3-c]pyridin-5-yl]methyl acetate.

MS (ES+) m/z 192 (MH+, 40%) and m/z 264 (MH+, 100%)

(d) Furo[2,3-c]pyridin-5-ylmethanol

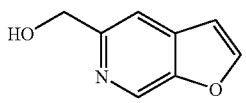

[2-(Trimethylsilyl)furo[2,3-c]pyridin-5-yl]methyl acetate (1.3 g, 4.9 mmol) was dissolved in ethanol (50 ml) and treated with potassium carbonate (0.82 g, 5.9 mmol) and heated under reflux for 18 hrs. The mixture was evaporated to dryness and the residue partitioned between ethyl acetate and water. The organic layer was dried, filtered and evaporated to yield the title compound (0.66 g).

Also to yield the desired compound: Furo[2,3-c]pyridin-5-ylmethyl acetate (1.15 g, 6 mmol) was dissolved in 1,4-dioxane (30 ml) and water (10 ml) and treated with 2N sodium hydroxide solution (12 ml) and stirred at RT for 18 h. The mixture was then partitioned between ethyl acetate and water, the organic layer was dried and evaporated to dryness to provide the desired compound (0.63 g).

MS (ES+) m/z 150 (MH+, 90%).

(e) 2,3-Dihydrofuro[2,3-c]pyridin-5-ylmethanol

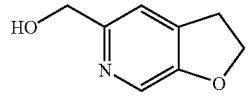

Furo[2,3-c]pyridin-5-ylmethanol (1.29 g, 8.7 mmol) was dissolved in ethanol (50 ml) and hydrogenated under 1 atmosphere of hydrogen at room temperature over 10% palladium on carbon for 18 h. The mixture was filtered and the filtrate evaporated to dryness to provide the desired compound (1.31 g, 100%).

MS (ES+) m/z 152 (MH+, 100%).

(f) 2,3-Dihydrofuro[2,3-c]pyridine-5-carbaldehyde

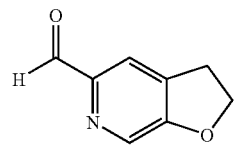

2,3-Dihydrofuro[2,3-c]pyridin-5-ylmethanol (1.31 g, 8.7 mmol) was dissolved in dichloromethane (100 ml) and treated with manganese dioxide (6 g, 69 mmol) at ambient temperature with vigorous stirring for 18 h. The mixture was filtered through kieselguhr and the filtrate evaporated to dryness to provide the desired compound (0.9 g, 70%).

MS (ES+) m/z 150 (MH+, 100%).

(g) Title Compound

The title compound was prepared from (4R)-4-[(4-amino-1-piperidinyl)methyl]-3-fluoro-4,5-dihydro-7H-pyrrolo[3,2,1-de]-1,5-naphthyridin-7-one Enantiomer 1 and 2,3-dihydrofuro[2,3-c]pyridine-5-carbaldehyde according to the general method of Example 2(h), but stirring for 1 hr after the addition of the sodium triacetoxyborohydride. The free base of the title compound was obtained in 77% yield.

$^1$H NMR CDCl$_3$) 1.40-1.52 (2H, m), 1.86-1.93 (2H, m), 2.09-2.13 (1H, m), 2.20-2.26 (1H, m), 2.51-2.57 (2H, m), 2.80-2.88 (2H, m), 2.96-2.99 (1H, broad d), 3.20-3.40 (2H, m), 3.85 (2H, s), 4.05-4.09 (1H, m), 4.47-4.49 (2H, m), 4.58-4.63 (2H, m), 6.83 (1H, d, J 10 Hz), 7.21 (1H, s), 7.89 (1H, d, J 10 Hz), 8.10 (1H, s), 8.32 (1H, s).

MS (ES+) m/z 436 (MH+, 100%).

The free base of the title compound was converted to the hydrochloride by dissolving in chloroform and adding 1 equivalent of 1M HCl/diethyl ether then evaporating to dryness. MS as that of free base.

Example 44

4-({cis-4-[(2,3-Dihydro[1,4]dioxino[2,3-c]pyridin-7-ylmethyl)amino]-3-fluoro-1-piperidinyl}methyl)-3-fluoro-4,5-dihydro-7H-pyrrolo[3,2,1-de]-1,5-naphthyridin-7-one Hydrochloride

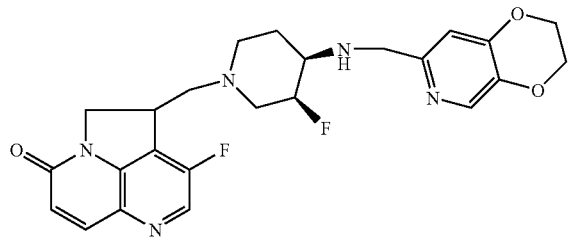

(a) Racemic methyl 2-[3-fluoro-6-(methyloxy)-1,5-naphthyridin-4-yl]-3-[(cis)-3-fluoro-4-({[(phenylmethyl)oxy]carbonyl}amino)-1-piperidinyl]propanoate

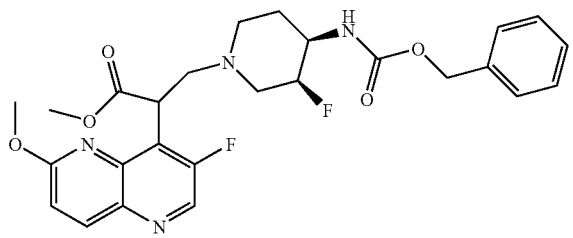

A solution of methyl 2-[3-fluoro-6-(methyloxy)-1,5-naphthyridin-4-yl]-2-propenoate (953 mg, 3.63 mmol), cis-phenylmethyl[3-fluoro-4-piperidinyl]carbamate Enantiomer 2 (for a synthesis see WO2004058144, prepared by analogy to Examples 142(b), (c) and (d) from the Enantiomer 2 of Example 142(a)) (1.1 g, 4.35 mmol) and 1,1,3,3-tetramethylguanidine (6 drops) in DMF (3.5 ml) was heated at 80° C. under argon for 3 hours, cooled and evaporated. Chromatography, eluting with 1% methanol/dichloromethane, gave the product in 100% yield.

MS (ES+) m/z 515 (MH+, 100%).

(b) Racemic phenylmethyl((cis-3-fluoro-1-{2-[3-fluoro-6-(methyloxy)-1,5-naphthyridin-4-yl]-3-hydroxypropyl}-4-piperidinyl)carbamate

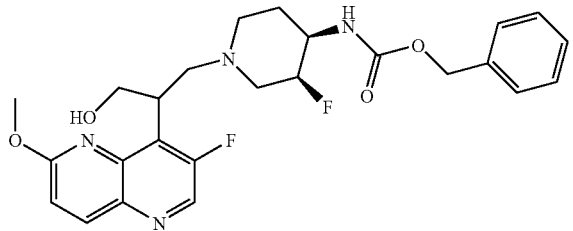

A solution of racemic methyl 2-[3-fluoro-6-(methyloxy)-1,5-naphthyridin-4-yl]-3-[(cis)-3-fluoro-4-({[(phenylmethyl)oxy]carbonyl}amino)-1-piperidinyl]propanoate (1.87 g, 3.63 mmol) in THF (40 ml) under argon at −70° C. was treated dropwise with a solution of lithium aluminium hydride in THF (4.18 ml) and allowed to warm slowly to −10° C. After stirring for 1 hour in an ice bath, the mixture was treated with water (0.314 ml), 2N NaOH solution (0.590 ml) and water (0.675 ml), stirred 30 minutes and filtered. The filtrate was evaporated and the residue chromatographed using a dichloromethane/methanol gradient to give the desired product (1.44 g, 81%).

MS (APCI+) m/z 487 (MH+, 100%).

(c) Racemic phenylmethyl {cis-3-fluoro-1-[(3-fluoro-7-oxo-4,5-dihydro-7H-pyrrolo[3,2,1-de]-1,5-naphthyridin-4-yl)methyl]-4-piperidinyl}carbamate

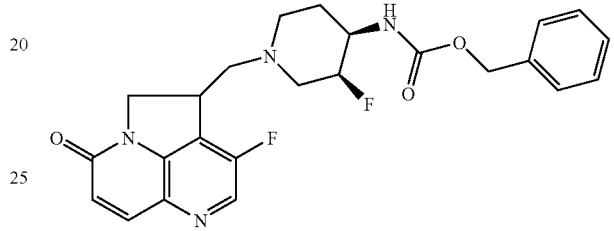

To a solution of racemic phenylmethyl((cis-3-fluoro-1-{2-[3-fluoro-6-(methyloxy)-1,5-naphthyridin-4-yl]-3-hydroxypropyl}-4-piperidinyl)carbamate (1.44 g, 2.96 mmol) in dichloromethane (13.5 ml) at 0° C. was added triethylamine (0.834 ml, 6 mmol) and methanesulfonic anhydride (0.644 g, 3.7 mmol). After 1 hour the reaction was warmed to room temperature, stirred for 20 h, heated at 40° C. for 3 days and then treated with dichloromethane and aqueous sodium bicarbonate solution. The aqueous phase was extracted twice with dichloromethane and the combined organic phases were dried and the solvent was removed. The residue was subjected to column chromatography on silica gel using a 2% methanol in dichloromethane eluent to provide the desired compound (1.218 g, 90%).

MS (APCI+) m/z 455 (MH+, 20%), 265 (100%).

(d) 4-{[cis-4-amino-3-fluoro-1-piperidinyl]methyl}-3-fluoro-4,5-dihydro-7H-pyrrolo[3,2,1-de]-1,5-naphthyridin-7-one

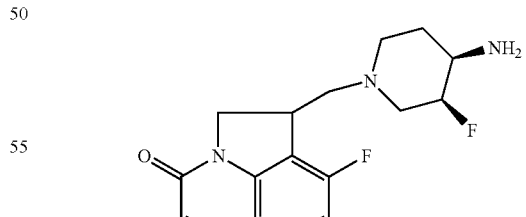

A solution of racemic phenylmethyl {cis-3-fluoro-1-[(3-fluoro-7-oxo-4,5-dihydro-7H-pyrrolo[3,2,1-de]-1,5-naphthyridin-4-yl)methyl]-4-piperidinyl}carbamate (1.218 g) in ethanol (20 ml)/1,4-dioxane (5 ml) was treated with 10% Pd/C (600 mg) and stirred under hydrogen at atmospheric pressure for 5 hours. After filtration through kieselguhr, the filtrate was evaporated and the residue chromatographed on silica gel, eluting with dichloromethane/methanol/0.88 aqueous ammonia, to give the desired compound (745 mg, 86%).

MS (APCI+) m/z 321 (MH+, 100%).

(e) Title Compound

The free base of the title compound was prepared from 4-{[cis-4-amino-3-fluoro-1-piperidinyl]methyl}3-fluoro-4,5-dihydro-7H-pyrrolo[3,2,1-de]-1,5-naphthyridin-7-one and 2,3-dihydro[1,4]dioxino[2,3-c]pyridine-7-carboxaldehyde (for a synthesis see WO2004058144, Example 2(c)) according to the general method of Example 2(h), chromatographing with dichloromethane/methanol/0.88 ammonia 95:5:0.5, in 82% yield.

$^1$H NMR δ (CDCl$_3$) 1.6-1.8 (2H, m), 2.15-3.3 (7H, m), 3.8-4.2 (4H, m), 4.25-4.35 (4H, m), 4.40-4.55 (2H, m), 6.83 (1H, d, J 10 Hz), 6.90 (1H, s), 7.88 (1H, d, J 10 Hz), 8.10 (1H, s), 8.33 (1H, s). MS (ES+) m/z 470 (MH+, 100%).

The free base of the title compound was converted to the hydrochloride by dissolving in chloroform and adding 1 equivalent of 1M HCl/diethyl ether, then evaporating to dryness. MS as that of free base.

Example 45

3-fluoro-4-[(cis-3-fluoro-4-{[(3-oxo-3,4-dihydro-2H-pyrido[3,2-b][1,4]oxazin-6-yl)methyl]amino}-1-piperidinyl)methyl]-4,5-dihydro-7H-pyrrolo[3,2,1-de]-1,5-naphthyridin-7-one Hydrochloride

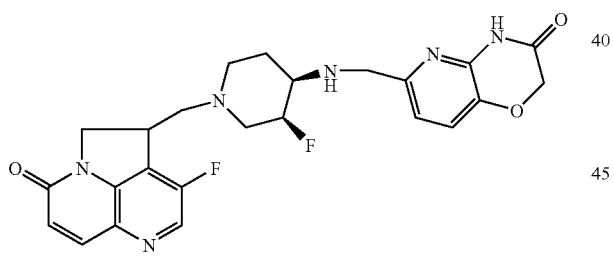

The free base of the title compound was synthesised from 4-{[cis-4-amino-3-fluoro-1-piperidinyl]methyl}-3-fluoro-4,5-dihydro-7H-pyrrolo[3,2,1-de]-1,5-naphthyridin-7-one and 3-oxo-3,4-dihydro-2H-pyrido[3,2-b][1,4]oxazine-6-carboxaldehyde (for a synthesis see WO2003087098, Example 31(e)), according to the general method of Example 2(h), chromatographing with dichloromethane/methanol/0.88 ammonia 95:5:0.5, in 88% yield.

MS (APCI+) m/z 483 (MH+, 80%), 203 (100%).

The free base of the title compound was converted to the hydrochloride by dissolving in chloroform and adding 1 equivalent of 1M HCl/diethyl ether, then evaporating to dryness. MS as that of free base.

Example 46

3-Fluoro-4-[(cis-3-fluoro-4-{[(3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one Hydrochloride

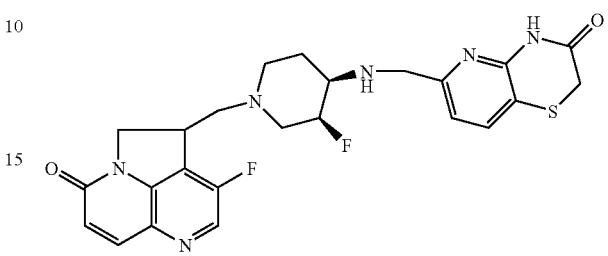

The free base of the title compound was synthesised from 4-{[cis-4-amino-3-fluoro-1-piperidinyl]methyl}-3-fluoro-4,5-dihydro-7H-pyrrolo[3,2,1-de]-1,5-naphthyridin-7-one and 3-oxo-3,4-dihydro-2H-pyrido[3,2-b][1,4]thiazine-6-carboxaldehyde (for a synthesis see WO2003087098, Example 301 (d)), according to the general method of Example 2(h), chromatographing with dichloromethane/methanol/0.88 ammonia 95:5:0.5, in 73% yield.

MS (ES+) m/z 499 (MH+, 40%), 179 (100%).

The free base of the title compound was converted to the hydrochloride by dissolving in chloroform and adding 1 equivalent of 1M HCl/diethyl ether, then evaporating to dryness. MS as that of free base.

Example 47

4-({{(cis-4-[(2,3-Dihydro-1,4-benzodioxin-6-ylmethyl)amino]-3-fluoro-1-piperidinyl}methyl)-3-fluoro-4,5-dihydro-7H-pyrrolo[3,2,1-de]-1,5-naphthyridin-7-one Hydrochloride

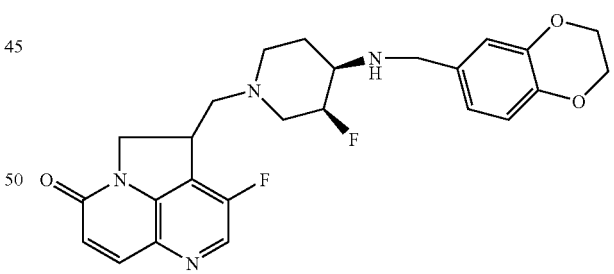

The free base of the title compound was synthesised from 4-{[cis-4-amino-3-fluoro-1-piperidinyl]methyl}-3-fluoro-4,5-dihydro-7H-pyrrolo[3,2,1-de]-1,5-naphthyridin-7-one and 2,3-dihydro-1,4-benzodioxin-6-carbaldehyde (Aldrich), according to the general method of Example 2(h), chromatographing with dichloromethane/methanol/0.88 ammonia 95:5:0.5, in 76% yield.

MS (ES+) m/z 469 (MH+, 10%), 149 (100%).

The free base of the title compound was converted to the hydrochloride by dissolving in chloroform and adding 1 equivalent of 1M HCl/diethyl ether, then evaporating to dryness. MS as that of free base.

Example 48

3-fluoro-4-{[cis-4-hydroxy-3-({[(3-oxo-3,4-dihydro-2H-pyrido[3,2-b][1,4]thiazin-6-yl)methyl]amino}methyl)-1-piperidinyl]methyl}-4,5-dihydro-7H-pyrrolo[3,2,1-de]-1,5-naphthyridin-7-one Hydrochloride

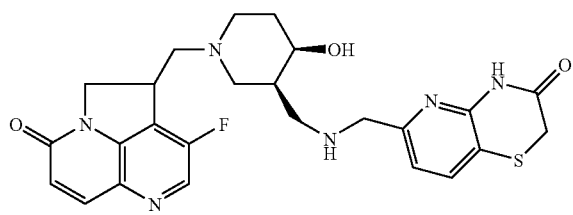

(a) Racemic ethyl 4-hydroxy-1-(phenylmethyl)-3-piperidinecarboxylate

Mixture of Cis and Trans

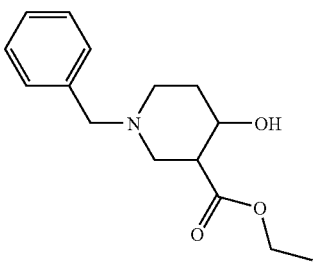

To a solution of ethyl 4-oxo-1-(phenylmethyl)-3-piperidinecarboxylate hydrochloride (50 g, 170 mmol) in methanol (1 l) was added triethylamine (28.3 ml, 204 mmol) and the mixture stiffed at room temperature for 10 min under argon. Sodium borohydride (21.32 g, 560 mmol) was then added portionwise and the reaction stirred at room temperature for 3 h. 5N HCl solution (175 ml) was added (final pH=2-3) and the mixture reduced to approx. 200 ml. The residue was neutralized with a saturated solution of sodium bicarbonate (150 ml) and the aqueous phase was extracted with dichloromethane and then a 9:1 dichloromethane:methanol mixture.

The organic layer was dried and the solvent was removed under reduced pressure. This provided the desired compound (37 g, 84%) as a mixture of cis and trans isomers in an approximately 1:1 ratio.

MS (ES+) m/z 264 (MH+, 100%).

(b) ethyl(cis)-4-hydroxy-1-(phenylmethyl)-3-piperidinecarboxylate

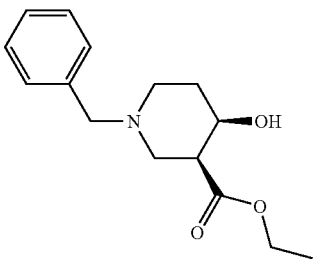

To a solution of racemic ethyl 4-hydroxy-1-(phenylmethyl)-3-piperidinecarboxylate (37 g, 140 mmol) in N,N-dimethylformamide (250 ml) was added tert-butyldimethylchlorosilane (10.6 g, 70 mmol) and imidazole (5.3 g, 77 mmol) under argon. The reaction was stirred at room temperature for 3 h; water was added and the aqueous phase was extracted with dichloromethane. The organic layer was dried and the solvent was removed under reduced pressure to afford 40 g of crude. The crude was divided into 3 batches (5 g, 17 g, 17 g) and each batch was subjected to column chromatography on silica gel using a hexane and ethyl acetate gradient (0-20% ethyl acetate in hexane). This provided the desired compound (16.67 g, 45%) and ethyl(trans)-4-{[(1,1-dimethylethyl)(dimethyl)silyl]oxy}-1-(phenylmethyl)-3-piperidinecarboxylate (15.8 g, 30%).

MS (ES+) m/z 264 (MH+, 100%).

(c) (cis)-4-hydroxy-1-(phenylmethyl)-3-piperidinecarboxylic acid sodium salt

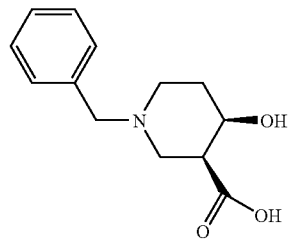

To a solution of ethyl(cis)-4-hydroxy-1-(phenylmethyl)-3-piperidinecarboxylate (16.67 g, 63.4 mmol) in THF/water (500 ml/50 ml) was added 2N sodium hydroxide solution (72 ml). The reaction mixture was stirred at room temperature for 5 h and then the pH was adjusted to 7 with 2N hydrochloric acid solution.

The mixture was reduced to approx 50 ml and the solid formed was filtered off, washed with water and dried in vacuo to afford the desired compound as its sodium salt (17 g, >100%).

MS (ES+) m/z 236 (MH+, 100%).

(d) (cis)-4-hydroxy-1-(phenylmethyl)-3-piperidinecarboxamide

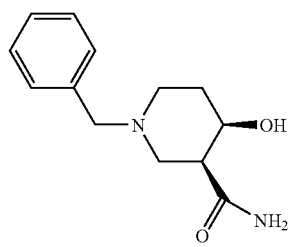

To a solution of (cis)-4-hydroxy-1-(phenylmethyl)-3-piperidinecarboxylic acid sodium salt (17 g) and 1-hydroxy-7-azabenzotriazole (5 g, 37 mmol) in N,N-dimethylformamide was added N-[3-(dimethylamino)propyl]-N'-ethylcarbodiimide hydrochloride (14.1 g, 73.4 mmol), followed by ammonium bicarbonate (21 g, 26.6 mmol). The reaction mixture was stirred at room temperature for 18 h. The solvent was then removed under reduced pressure and the residue was treated with aqueous sodium bicarbonate solution. The aqueous phase was extracted with 9:1 dichloromethane:methanol mixture. The organic layer was dried (MgSO$_4$) and the solvent was removed under reduced pressure. The residue was subjected to column chromatography on silica gel using a methanol and dichloromethane gradient (0-20% methanol/dichloromethane). This provided the desired compound (9.5 g, 62%).

MS (ES+) m/z 235 (MH$^+$, 80%), 257 (100%).

(e) (cis)-3-(aminomethyl)-1-(phenylmethyl)-4-piperidinol

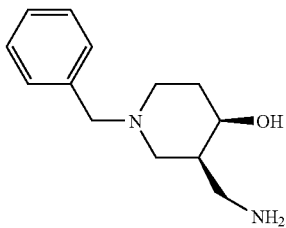

A solution of (cis)-4-hydroxy-1-(phenylmethyl)-3-piperidinecarboxamide (0.7 g, 3 mmol) in THF (6 ml) was treated with a borane-methyl sulphide complex (2M solution in THF, 3.3 ml). The reaction mixture was heated at 80° C. for 1300 s under microwave irradiation conditions. This was repeated twelve times and then the reaction mixtures were combined and the solvent was removed under reduced pressure and the residue was subjected to column chromatography on silica gel using a dichloromethane, methanol and aqueous ammonia gradient (20% methanol/dichloromethane-20% 2M ammonia in methanol/dichloromethane) to provide 4.6 g of the desired pure compound and 1.1 g of less pure material.

MS (ES+) m/z 219 (MH$^+$, 100%).

(f) 1,1-dimethylethyl {[(cis)-4-hydroxy-1-(phenylmethyl)-3-piperidinyl]methyl}carbamate

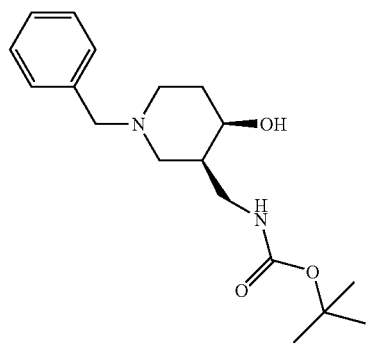

(cis)-3-(aminomethyl)-1-(phenylmethyl)-4-piperidinol (4.6 g, 21.1 mmol) was dissolved in chloroform (125 ml) and stirred over sodium bicarbonate (4.5 g, 53.6 mmol). A solution of di-tert-butyl dicarbonate (4.64 g, 21.1 mmol) in chloroform (60 ml) was then added over 0.5 h and the reaction mixture stirred at room temperature. Water was added and the two phases separated. The aqueous phase was re-extracted with 9:1 dichloromethane:methanol mixture. The combined organic fractions were dried and the solvent was removed under reduced pressure. The residue was subjected to column chromatography on silica gel using a methanol and dichloromethane gradient (0-10% methanol in dichloromethane). This provided the desired compound (5 g, 75%).

MS (ES+) m/z 321 (MH$^+$, 40%), 265 (100%).

(g) 1,1-dimethylethyl {[(cis)-4-hydroxy-1-(phenylmethyl)-3-piperidinyl]methyl}carbamate, Enantiomers 1 and 2

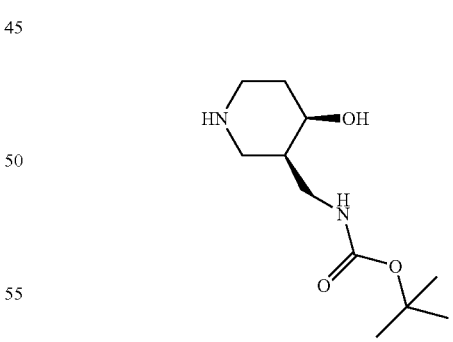

Racemic 1,1-dimethylethyl {[(cis)-4-hydroxy-1-phenylmethyl)-3-piperidinyl]methyl}carbamate (5 g) was subjected to preparative HPLC on Chiralpak AD. This procedure gave the faster running enantiomer (Enantiomer 1, 2.2 g) in >98% ee and the slower running enantiomer (Enantiomer 2, 2.2 g) in 97% ee.

(h) 1,1-dimethylethyl{([(cis)-4-hydroxy-3-piperidinyl]methyl}carbamate

A solution of 1,1-dimethylethyl{[(cis)-4-hydroxy-1-(phenylmethyl)-3-piperidinyl]methyl}carbamate Enantiomer 1 (2.2 g, 6.8 mmol) in methanol (50 ml) was stirred under hydrogen and at room temperature in presence of 20% Palladium hydroxide (0.5 g) for 18 h. After filtration through kieselguhr, the methanol was removed under reduced pressure to afford the desired product (1.6 g, 100%).

MS (ES+) m/z 231 (MH$^+$, 100%)

(j) methyl 3-{(cis-3-[({[(1,1-dimethylethyl)oxy]carbonyl}amino)methyl]-4-hydroxy-1-piperidinyl}-2-[3-fluoro-6-(methyloxy)-1,5-naphthyridin-4-yl]propanoate

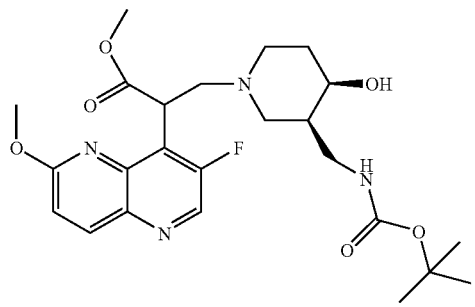

A mixture of methyl 2-[3-fluoro-6-(methyloxy)-1,5-naphthyridin-4-yl]-2-propenoate (1.05 g, 4 mmol) (Example 10(c)), 1,1-dimethylethyl{[cis-4-hydroxy-3-piperidinyl]methyl}carbamate Enantiomer 1 (1 g, 4.4 mmol) and 1,1,3,3-tetramethylguanidine (0.2 ml) in N,N-dimethylformamide (10 ml) was heated at 30° C. for 18 h, cooled and evaporated to dryness. Chromatography, eluting with methanol/dichloromethane (0-10% methanol/dichloromethane) gave 1.3 g of impure product. The residue was subjected to column chromatography on silica gel again using a different methanol and dichloromethane gradient (0-5% methanol in dichloromethane). This provided two impure batches of the desired compound (0.9 g and 0.25 g).

MS (ES+) m/z 493 (MH+, 500%), 243 (100%).

(k) 1,1-dimethylethyl[(cis-1-{2-[3-fluoro-6-(methyloxy)-1,5-naphthyridin-4-yl]-3-hydroxypropyl}-4-hydroxy-3-piperidinyl)methyl]carbamate

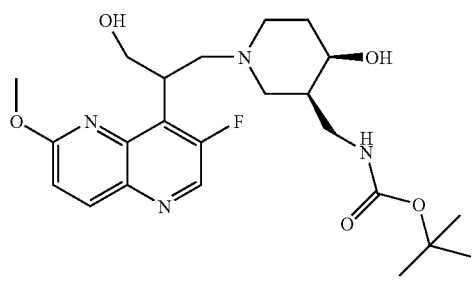

A solution of methyl 3-{(cis-3-[({[(1,1-dimethylethyl)oxy]carbonyl}amino)methyl]-4-hydroxy-1-piperidinyl}-2-[3-fluoro-6-(methyloxy)-1,5-naphthyridin-4-yl]propanoate (0.9 g, 1.83 mmol) in THF (20 ml) at −70° C. under argon was treated dropwise with a 1M solution of lithium aluminium hydride in THF (2.1 ml) and allowed to warm gradually to −10° C. and then stirred in an ice-water bath for 2 h. The solution was then treated with water (0.16 ml), 2N sodium hydroxide (0.3 ml) and water (0.34 ml), stirred 1 hour and filtered. The filtrate was evaporated and the residue chromatographed, eluting with methanol/dichloromethane gradient (0-8% methanol/dichloromethane) to give the desired product (425 mg).

MS (ES+) m/z 465 (MH+, 50%), 187 (100%).

(l) 1,1-dimethylethyl({(cis-1-[(3-fluoro-7-oxo-4,5-dihydro-7H-pyrrolo[3,2,1-de]-1,5-naphthyridin-4-yl)methyl]-4-hydroxy-3-piperidinyl}methyl)carbamate

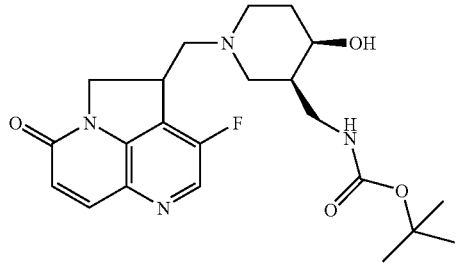

To a solution of 1,1-dimethylethyl[(cis-1-{2-[3-fluoro-6-(methyloxy)-1,5-naphthyridin-4-yl]-3-hydroxypropyl}-4-hydroxy-3-piperidinyl)methyl]carbamate (0.525 g, 1.13 mmol) in chloroform (8 ml) at 0° C. was added triethylamine (0.3 ml, 2.26 mmol) and p-toluenesulfonic anhydride (0.406 g, 1.243 mmol). The reaction was slowly warmed to room temperature and then heated at 50° C. for 24 h. The reaction mixture was then treated with aqueous saturated sodium bicarbonate solution. The aqueous phase was extracted three times with 9:1 dichloromethane:methanol mixture and the combined organic phases were dried and the solvent was removed under reduced pressure. The residue was subjected to column chromatography on silica gel using a dichloromethane and methanol gradient (0-10% methanol/dichloromethane) to provide 0.23 g of a 2:1 product: starting material mixture. This mixture was re-subjected to the same procedure as above (assuming 0.08 g of starting material); 0.043 ml of triethylamine, 0.06 g of p-toluenesulfonic anhydride, and 4 ml of chloroform were used. The reaction was slowly warmed to room temperature and then heated at 50° C. for 24 h. Work up and chromatography as above afforded the desired compound (1.48 g, 79%).

MS (ES+) m/z 433 (MH+, 60%), 333 (80%).

(m) 4-{[cis-3-(aminomethyl)-4-hydroxy-1-piperidinyl]methyl}-3-fluoro-4,5-dihydro-7H-pyrrolo[3,2,1-de]-1,5-naphthyridin-7-one

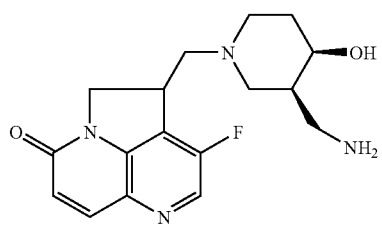

A suspension of 1,1-dimethylethyl({(cis-1-[(3-fluoro-7-oxo-4,5-dihydro-7H-pyrrolo[3,2,1-de]-1,5-naphthyridin-4-yl)methyl]-4-hydroxy-3-piperidinyl}methyl)carbamate (0.175 g, 0.405 mmol) in dichloromethane (2 ml) was treated with trifluoroacetic acid (1 ml) and stirred at room temperature for 20 min. The reaction mixture was evaporated and then redissolved using a 4:1 dichloromethane:methanol solution. The organic phase was then treated with aqueous sodium bicarbonate solution. The aqueous phase was extracted 10 times with a 4:1 dichloromethane:methanol solution and then the combined organic phases were dried and the solvent was removed under reduced pressure and the residue was subjected to column chromatography on silica gel using a dichloromethane, methanol and ammonia gradient to provide the desired compound (0.08 g).

MS (ES+) m/z 333 (MH+, 50%), 167 (100%).

(n) Title Compound

A mixture of 4-{[cis-3-(aminomethyl)-4-hydroxy-1-piperidinyl]methyl}-3-fluoro-4,5-dihydro-7H-pyrrolo[3,2,1-de]-1,5-naphthyridin-7-one (40 mg, 0.12 mmol) and 3-oxo-3,4-dihydro-2H-pyrido[3,2-h][1,4]thiazine-6-carboxaldehyde (for a synthesis see WO2003087098, Example 301 (d)) (24 mg, 0.12 mmol) and 3A molecular sieves in chloroform (1.5 ml) and methanol (1.5 ml) was heated at 80° C. for 2 h, cooled and then sodium triacetoxyborohydride (64 mg, 0.30 mmol) was added. The reaction was stirred at room temperature for 18 h and then the solids were filtered off and the solvent was removed under reduced pressure. The residue was subjected to column chromatography on silica gel using a dichloromethane and methanol gradient (0-20% methanol/dichloromethane) to provide the free base of the title compound (37 mg, 35%).

$^1$H NMR δ (MeOD) 1.7-3.2 (7H, m), 3.4-3.6 (4H, m), 3.9-4.1 (2H, m), 4.2-4.6 (6H, m), 6.84 (1H, d), 7.11 (1H, m), 7.80 (1H, m), 7.99 (1H, m), 8.34 (1H, m). MS (ES+) m/z 511 (MH+, 50%), 191 (100%).

The free base of the title compound was converted to the hydrochloride by dissolving in chloroform and adding 1 equivalent of 1M HCl/diethyl ether then evaporating to dryness. MS as that of free base.

Example 49

4-[(cis-3-{[(2,3-Dihydro[1,4]dioxino[2,3-c]pyridin-7-ylmethyl)amino]methyl}-4-hydroxy-1-piperidinyl) methyl]-3-fluoro-4,5-dihydro-7H-pyrrolo[3,2,1-de]-1,5-naphthyridin-7-one

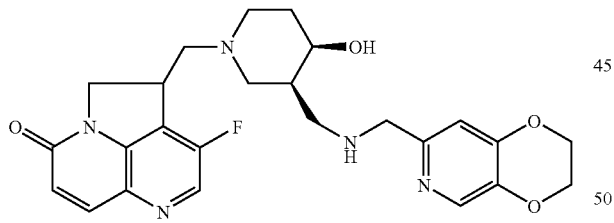

A mixture of 4-{[cis-3-(aminomethyl)-4-hydroxy-1-piperidinyl]methyl}-3-fluoro-4,5-dihydro-7H-pyrrolo[3,2,1-de]-1,5-naphthyridin-7-one (40 mg, 0.12 mmol) and 2,3-dihydro[1,4]dioxino[2,3-c]pyridine-7-carboxaldehyde (for a synthesis see WO2004058144, Example 2(c)) (20 mg, 0.12 mmol) and 3A molecular sieves in chloroform (3 ml) and methanol (3 ml) was heated at 80° C. for 2 h, cooled and then sodium triacetoxyborohydride (64 mg, 0.30 mmol) was added. The reaction was stirred at room temperature for 18 h and then the solids were filtered off and the solvent was removed under reduced pressure. The residue was subjected to column chromatography on silica gel using a dichloromethane and methanol gradient (0-20% methanol/dichloromethane) to provide the 33 mg of impure compound. MDAP purification provided 14 mg of the formate salt and subsequent solid phase, ion exchange (SCX) treatment afforded 10 mg of the title compound.

MS (ES+) m/z 482 (MH+, 50%), 241 (100%).

Example 50

4-[((2S)-2-{[(2,3-Ddihydro[1,4]dioxino[2,3-c]pyridin-7-ylmethyl)amino]methyl}-4-morpholinyl)methyl]-3-fluoro-4,5-dihydro-7H-pyrrolo[3,2,1-de]-1,5-naphthyridin-7-one Hydrochloride

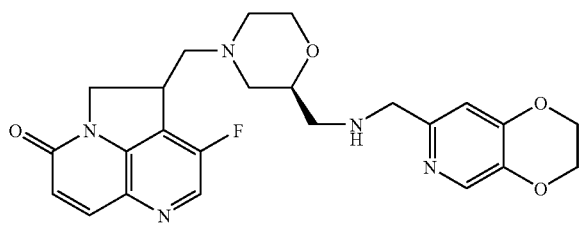

(a) 1,1-Dimethylethyl({(2S)-4-[(3,4-dichlorophenyl) methyl]-2-morpholinyl}methyl)carbamate

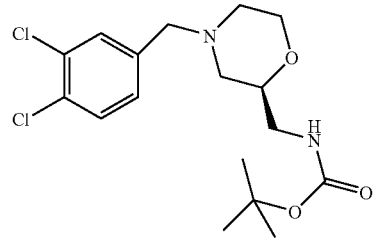

({(2S)-4-[(3,4-Dichlorophenyl)methyl]-2-morpholinyl}methyl)amine (for a synthesis see WO03/082835A1 Example 1) (4.9 g) in ethyl acetate (40 mL) was stirred with di-tert-butyl dicarbonate (5.95 g) overnight at room temperature then evaporated and chromatographed on silica gel (0-5% methanol-DCM) to give the desired product (6.05 g).

(b) Phenylmethyl (2S)-2-[({[(1,1-dimethylethyl)oxy] carbonyl}amino)methyl]-4-morpholinecarboxylate

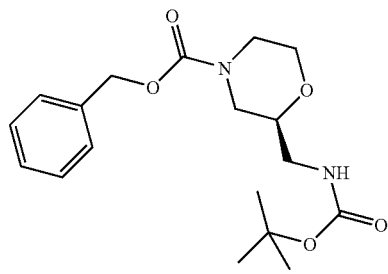

A solution of 1,1-dimethylethyl({(2S)-4-[(3,4-dichlorophenyl)methyl]-2-morpholinyl}methyl)carbamate (2.0 g) in methanol (30 mL) and triethylamine (2.2 mL) was hydrogenated over 10% palladium on charcoal (1.0 g) at 50 psi for 24 hours then filtered through Celite and evaporated. The residue was stirred in ethyl acetate (50 mL), saturated sodium bicarbonate (50 mL) and benzyl chloroformate (1.62 mL) overnight. The organic layer was separated, dried (sodium sulfate) and evaporated. Purification on silica gel (0-2% methanol-DCM) gave the desired product (1.3 g).

(c) 1,1-Dimethylethyl[(2R)-2-morpholinylmethyl]carbamate

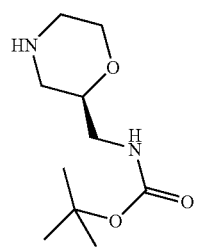

A solution of phenylmethyl (2S)-2-[({[(1,1-dimethylethyl)oxy]carbonyl}amino)methyl]-4-morpholinecarboxylate was dissolved in methanol (75 mL) and hydrogenated at atmospheric pressure over 10% palladium on charcoal (0.5 g) overnight, then filtered through Celite and evaporated to give the desired compound (0.81 g).

$^1$H NMR δ (CDCl$_3$) 1.44 (9H, s), 2.50-2.65 (1H, m), 2.70-2.95 (3H, m), 2.95-3.10 (1H, m), 3.45-3.70 (2H, m), 3.80-3.90 (1H, m), 4.88 (1H, br s).

(d) Racemic methyl 3-{(2S)-2-[({[(1,1-dimethylethyl)oxy]carbonyl}amino)methyl]-4-morpholinyl}-2-[3-fluoro-6-(methyloxy)-1,5-naphthyridin-4-yl]propanoate

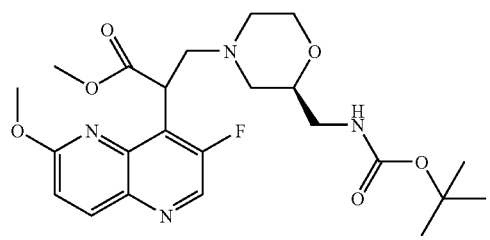

This compound was prepared from methyl 2-[3-fluoro-6-(methyloxy)-1,5-naphthyridin-4-yl]-2-propenoate and 1,1-dimethylethyl[(2R)-2-morpholinylmethyl]carbamate according to the general method of Example 2(d), in 100% yield.

MS (ES+) m/z 479 (MH$^+$, 30%), 379 (100%).

(e) Racemic 1,1-dimethylethyl[((2S)-4-{2-[3-fluoro-6-(methyloxy)-1,5-naphthyridin-4-yl]-3-hydroxypropyl}-2-morpholinyl)methyl]carbamate

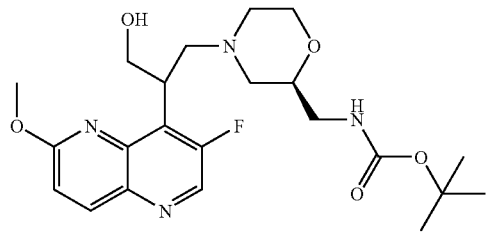

This compound was prepared from racemic methyl 3-{(2S)-2-[({[(1,1-dimethylethyl)oxy]carbonyl}amino)methyl]-4-morpholinyl}-2-[3-fluoro-6-(methyloxy)-1,5-naphthyridin-4-yl]propanoate, according to the general method of Example 48(k), in 85% yield.

MS (ES+) m/z 451 (MH$^+$, 25%).

(f) Racemic 1,1-dimethylethyl({(2S)-4-[(3-fluoro-7-oxo-4,5-dihydro-7H-pyrrolo[3,2,1-de]-1,5-naphthyridin-4-yl)methyl]-2-morpholinyl}methyl)carbamate

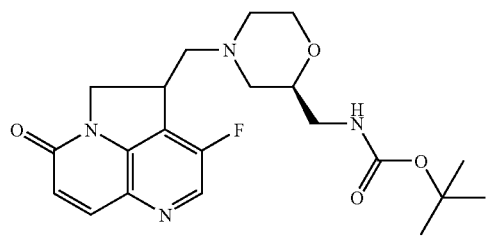

To a solution of 1,1-dimethylethyl[((2S)-4-{2-[3-fluoro-6-(methyloxy)-1,5-naphthyridin-4-yl]-3-hydroxypropyl}-2-morpholinyl)methyl]carbamate (1.2 g, 2.7 mmol) in dichloromethane (15 ml) at 0° C. was added triethylamine (0.6 ml, 4.32 mmol) and methanesulfonyl chloride (0.26 ml, 3.38 mmol). The reaction was slowly warmed to room temperature and then heated at 35° C. then at 50° C. for 18 h. The reaction mixture was then treated with aqueous saturated sodium bicarbonate solution. The aqueous phase was extracted three times with 9:1 dichloromethane:methanol mixture and the combined organic phases were dried and the solvent was removed under reduced pressure. The residue was subjected to column chromatography on silica gel using a dichloromethane and methanol gradient (0-10% methanol/dichloromethane) to provide the desired compound (0.71 g, 63%).

MS (ES+) m/z 419 (MHz, 25%).

(g) Racemic 4-{[(2S)-2-(aminomethyl)-4-morpholinyl]methyl}-3-fluoro-4,5-dihydro-7H-pyrrolo[3,2,1-de]-1,5-naphthyridin-7-one

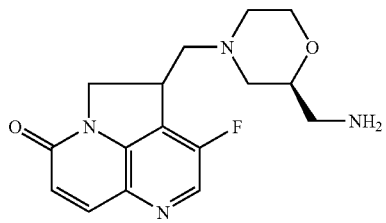

This compound was prepared from racemic 1,1-dimethylethyl({(2S)-4-[(3-fluoro-7-oxo-4,5-dihydro-7H-pyrrolo[3,2,1-de]-1,5-naphthyridin-4-yl)methyl]-2-morpholinyl}methyl)carbamate, according to the general method of Example 48(m), in 100% yield.

MS (ES+) m/z 319 (MH$^+$, 15%).

(h) Title Compound

The free base of the title compound was prepared from racemic 4-{[(2S)-2-(aminomethyl)-4-morpholinyl]methyl}-3-fluoro-4,5-dihydro-7H-pyrrolo[3,2,1-de]-1,5-naphthyridin-7-one and 2,3-dihydro[1,4]dioxino[2,3-c]pyridine-7-carbaldehyde (for a synthesis see WO2004058144, Example 2(c)) according to the general method of Example 48(n) in 5% yield.

$^1$H NMR δ (MeOD) 1.9-2.4 (4H, m), 2.6-3 (6H, m), 3.6-4 (4H, m), 4.2-4.6 (6H, m), 6.83 (1H, d), 6.95 (1H, d), 8.01 (2H, m), 8.39 (1H, s). MS (ES+) m/z 468 (MH$^+$, 40%), 234 (100%).

The free base of the title compound was converted to the hydrochloride by dissolving in chloroform and adding 1 equivalent of 1M HCl/diethyl ether then evaporating to dryness. MS as that of free base.

Example 51

3-Fluoro-4-[((2S)-2-{[([1,3]oxathiolo[5,4-c]pyridin-6-ylmethyl)amino]methyl}-4-morpholinyl)methyl]-4,5-dihydro-7H-pyrrolo[3,2,1-de]-1,5-naphthyridin-7-one hydrochloride

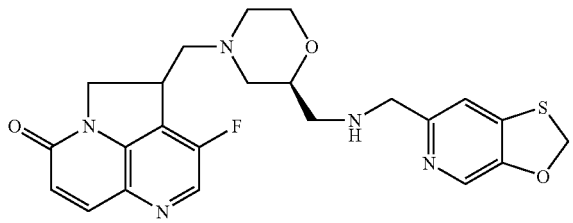

The free base of the title compound was synthesised from racemic 4-{[(2S)-2-(aminomethyl)-4-morpholinyl]methyl}-3-fluoro-4,5-dihydro-7H-pyrrolo[3,2,1-de]-1,5-naphthyridin-7-one and [1,3]oxathiolo[5,4-c]pyridine-6-carbaldehyde (for a synthesis see WO2004058144, Example 61) according to the general method of Example 48(n), in 38% yield.

MS (ES+) m/z 470 (MH$^+$, 35%), 235 (100%).

The free base of the title compound was converted to the hydrochloride by dissolving in chloroform and adding 1 equivalent of 1M HCl/diethyl ether, then evaporating to dryness. MS as that of free base.

Example 52

3-Fluoro-4-{[(2S)-2-({[(3-oxo-3,4-dihydro-2H-pyrido[3,2-b][1,4]thiazin-6-yl)methyl]amino}methyl)-4-morpholinyl]methyl}-4,5-dihydro-7H-pyrrolo[3,2,1-de]-1,5-naphthyridin-7-one Hydrochloride

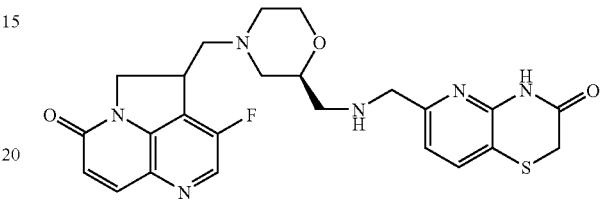

The free base of the title compound was synthesised from racemic 4-{[(2S)-2-(aminomethyl)-4-morpholinyl]methyl}-3-fluoro-4,5-dihydro-7H-pyrrolo[3,2,1-de]-1,5-naphthyridin-7-one and 3-oxo-3,4-dihydro-2H-pyrido[3,2-b][1,4]thiazine-6-carboxaldehyde (for a synthesis see WO2003087098, Example 301(d)) according to the general method of Example 48(n), in 39% yield.

MS (ES+) m/z 497 (MH$^+$, 25%), 249 (100%).

The free base of the title compound was converted to the hydrochloride by dissolving in chloroform and adding 1 equivalent of 1M HCl/diethyl ether, then evaporating to dryness. MS as that of free base.

Example 53

3-Chloro-4-({4-[i[1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one Enantiomer 2 Hydrochloride

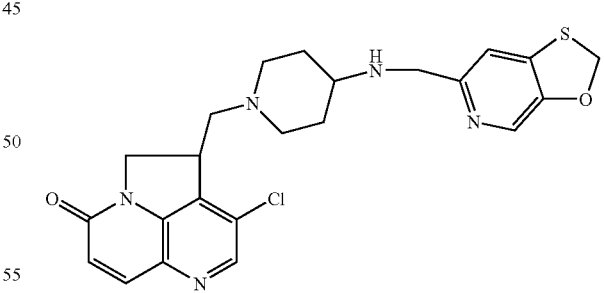

The free base of the title compound was synthesised from 4-[(4-amino-1-piperidinyl)methyl]-3-chloro-4,5-dihydro-7H-pyrrolo[3,2,1-de]-1,5-naphthyridin-7-one Enantiomer 2 and [1,3]oxathiolo[5,4-c]pyridine-6-carbaldehyde (for a synthesis see WO2004058144, Example 61) according to the general method of Example 24(b) in 72% yield.

The free base of the title compound was converted to the hydrochloride by dissolving in chloroform and adding 1 equivalent of 1M HCl/diethyl ether, then evaporating to dryness.

Example 54

3-Chloro-4-({4-[(3,4-dihydro-2H-pyrano[2,3-c]pyridin-6-ylmethyl)amino]-1-piperidinyl}methyl)-4,5-dihydro-7H-pyrrolo[3,2,1-de]-1,5-naphthyridin-7-one Enantiomer 2 Hydrochloride

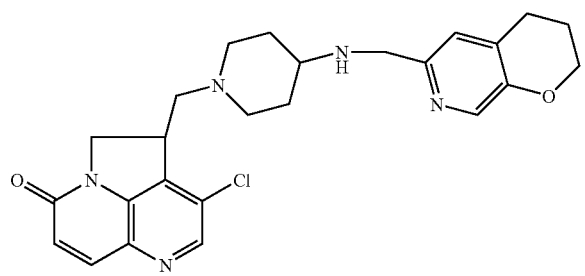

The free base of the title compound was synthesised from 4-[(4-amino-1-piperidinyl)methyl]-3-chloro-4,5-dihydro-7H-pyrrolo[3,2,1-de]-1,5-naphthyridin-7-one Enantiomer 2 and 3,4-dihydro-2H-pyrano[2,3-c]pyridine-6-carbaldehyde (for a synthesis see WO2004058144, Example 126(e)) according to the general method of Example 24(b) in 73% yield.

The free base of the title compound was converted to the hydrochloride by dissolving in chloroform and adding 1 equivalent of 1M HCl/diethyl ether, then evaporating to dryness.

Example 55

3-Chloro-4-[(4-{[(3-oxo-3,4-dihydro-2H-pyrido[3,2-b][1,4]oxazin-6-yl)methyl]amino}-1-piperidinyl)methyl]-4,5-dihydro-7H-pyrrolo[3,2,1-de]-1,5-naphthyridin-7-one Enantiomer 2 Hydrochloride

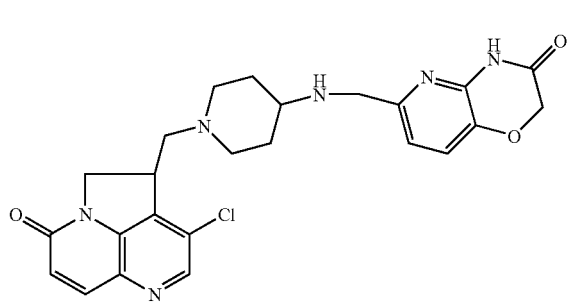

The free base of the title compound was synthesised from 4-[(4-amino-1-piperidinyl)methyl]-3-chloro-4,5-dihydro-7H-pyrrolo[3,2,1-de]-1,5-naphthyridin-7-one Enantiomer 2 and 3-oxo-3,4-dihydro-2H-pyrido[3,2-b][1,4]oxazine-6-carboxaldehyde (for a synthesis see WO2003087098, Example 31(e)) according to the general method of Example 24(b) in 73% yield.

The free base of the title compound was converted to the hydrochloride by dissolving in chloroform and adding 1 equivalent of 1M HCl/diethyl ether, then evaporating to dryness.

Example 56

3-Chloro-4-({(3R,4S)-3-hydroxy-4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one Hydrochloride

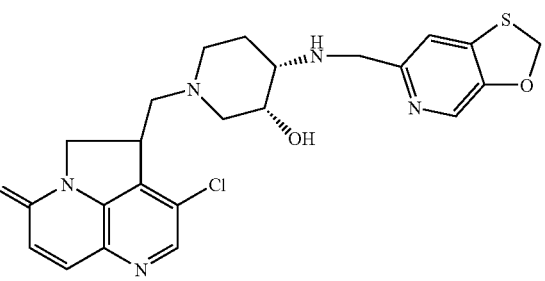

The free base of the title compound was synthesised from racemic 4-{[(3R,4S)-4-amino-3-hydroxy-1-piperidinyl]methyl}-3-chloro-4,5-dihydro-7H-pyrrolo[3,2,1-de]-1,5-naphthyridin-7-one and [1,3]oxathiolo[5,4-c]pyridine-6-carbaldehyde (for a synthesis see WO2004058144, Example 61) according to the general method of Example 24(b). The free base of the title compound was converted to the hydrochloride by dissolving in chloroform and adding 1 equivalent of 1M HCl/diethyl ether, then evaporating to dryness. MS as that of free base.

Example 57

3-Fluoro-4-({(3R,4S)-3-hydroxy-4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one Hydrochloride

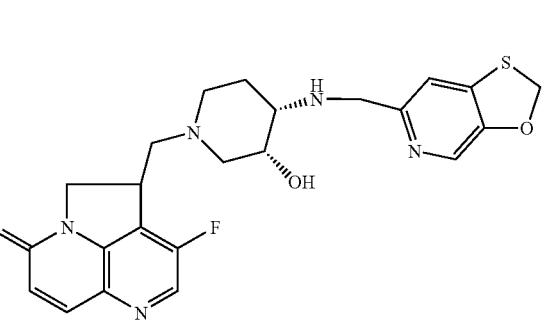

The free base of the title compound was synthesised from racemic 4-{[(3R,4S)-4-amino-3-hydroxy-1-piperidinyl]methyl}-3-fluoro-4,5-dihydro-7H-pyrrolo[3,2,1-de]-1,5-naphthyridin-7-one and [1,3]oxathiolo[5,4-c]pyridine-6-carbaldehyde (for a synthesis see WO2004058144, Example 61) according to the general method of Example 24(b). The free base of the title compound was converted to the hydrochloride by dissolving in chloroform and adding 1 equivalent of 1M HCl/diethyl ether, then evaporating to dryness. MS as that of free base.

Example 58

7-[({(3R,4S)-1-[(3-Chloro-7-oxo-4,5-dihydro-7H-pyrrolo[3,2,1-de]-1,5-naphthyridin-4-yl)methyl]-3-hydroxy-4-piperidinyl}amino)methyl]-2,3-dihydro-1,4-benzodioxin-5-carbonitrile Diastereomer 2 Hydrochloride

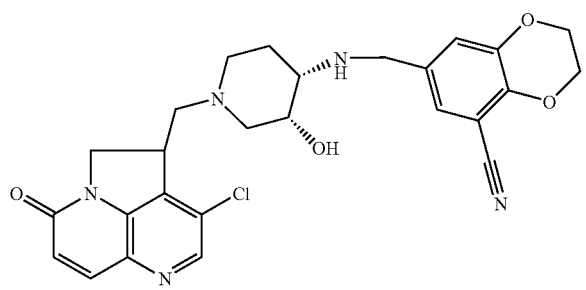

The free base of the title compound was synthesised from 4-{[(3R,4S)-4-amino-3-hydroxy-1-piperidinyl]methyl}-3-chloro-4,5-dihydro-7H-pyrrolo[3,2,1-de]-1,5-naphthyridin-7-one Diastereomer 2 and 8-cyano-2,3-dihydro-1,4-benzodioxin-6-carbaldehyde according to the general method of Example 2(h).

The free base of the title compound was converted to the hydrochloride by dissolving in chloroform and adding 1 equivalent of 1M HCl/diethyl ether, then evaporating to dryness. MS as that of free base.

Example 59

4-({4-[(2,3-Dihydro[1,4]dioxino[2,3-c]pyridin-7-ylmethyl)amino]-1-piperidinyl}methyl)-4,5-dihydro-7H-pyrrolo[3,2,1-de]-1,5-naphthyridin-7-one Hydrochloride

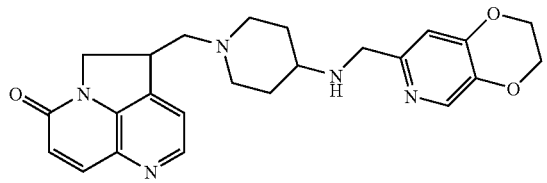

(a) 4-[(4-amino-1-piperidinyl)methyl]-4,5-dihydro-7H-pyrrolo[3,2,1-de]-1,5-naphthyridin-7-one SD104584-086

1,1-Dimethylethyl {1-[(7-oxo-4,5-dihydro-7H-pyrrolo[3,2,1-de]-1,5-naphthyridin-4-yl)methyl]-4-piperidinyl}carbamate (0.21 g) was treated with trifluoroacetic acid (2 ml) in dichloromethane (10 ml) at ambient temperature for 45 mins. The mixture was evaporated to dryness and the residue partitioned between saturated aqueous potassium carbonate solution and 10% methanol in dichloromethane (5×30 ml). The combined organics were dried, filtered and evaporated to dryness to give the desired compound.

(b) Title Compound

The free base of the title compound was synthesised from 4-[(4-amino-1-piperidinyl)methyl]-4,5-dihydro-7H-pyrrolo[3,2,1-de]-1,5-naphthyridin-7-one and 2,3-dihydro[1,4]dioxino[2,3-c]pyridine-7-carboxaldehyde (for a synthesis see WO2004058144, Example 2(c)) according to the general method of Example 2(h).

MS (ES+) m/z 434 (MH$^+$, 25%).

The free base of the title compound was converted to the hydrochloride by dissolving in chloroform and adding 1 equivalent of 1M HCl/diethyl ether, then evaporating to dryness. MS as that of free base.

Example 60

4-({4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one hydrochloride

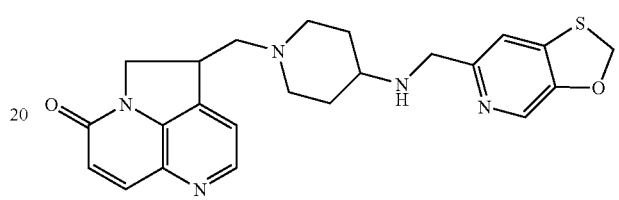

The free base of the title compound was synthesised from 4-[(4-amino-1-piperidinyl)methyl]-4,5-dihydro-7H-pyrrolo[3,2,1-de]-1,5-naphthyridin-7-one dihydrochloride salt and [1,3]oxathiolo[5,4-c]pyridine-6-carbaldehyde (for a synthesis see WO2004058144, Example 61) according to the general method of Example 2(h).

MS (ES+) m/z 436 (MH$^+$, 20%).

The free base of the title compound was converted to the hydrochloride by dissolving in chloroform and adding 1 equivalent of 1M HCl/diethyl ether, then evaporating to dryness. MS as that of free base.

Example 61

7-{[(1-{[(4R)-3-Fluoro-7-oxo-4,5-dihydro-7H-pyrrolo[3,2,1-de]-1,5-naphthyridin-4-yl]methyl}-4-piperidinyl)amino]methyl}-2,3-dihydro-1,4-benzodioxin-5-carbonitrile Enantiomer 1 Dihydrochloride

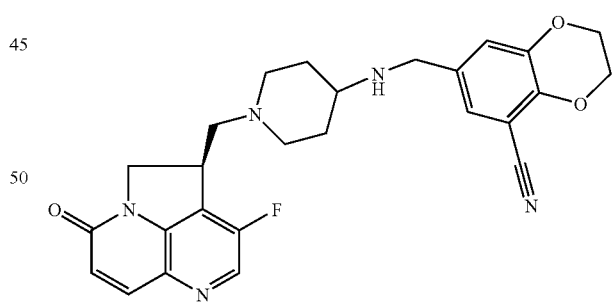

(4R)-4-[(4-amino-1-piperidinyl)methyl]-3-fluoro-4,5-dihydro-7H-pyrrolo[3,2,1-de]-1,5-naphthyridin-7-one Enantiomer 1 (50 mg, 0.166 mmol) and 8-cyano-2,3-dihydro-1,4-benzodioxin-6-carbaldehyde (31 mg, 0.166 mol) were stirred in chloroform (2 mL) and methanol (2 mL) containing acetic acid (6 drops) and 3A molecular sieves for 2 h at room temperature. Sodium cyanoborohydride (40 g) was added and the mixture was stirred for 3.5 h. The mixture was diluted with dichloromethane, basified with aqueous sodium bicarbonate and the phases were separated. The aqueous phase was extracted twice with 10% methanol/dichloromethane, and the combined organics were dried and evaporated. Chromatography on silica, eluting with 0-10% methanol/dichloromethane, gave the free base of the title compound (53 mg, 67%).

MS (+ve ion electrospray): m/z 476 [MH+]. ¹H NMR (400 MHz, CDCl₃) δ 8.33 (1H, d), 7.89 (1H, d), 7.11 (1H, d), 7.08 (1H, d), 6.84 (1H, d), 4.48 (2H, m), 4.39 (2H, m), 4.30 (2H, m), 4.08 (1H, m), 3.71 (2H, s), 2.97 (1H, d), 2.86 (1H, dd), 2.79 (1H, d), 2.55 (1H, dd), 2.49 (1H, m), 2.23 (1H, t), 2.11 (1H, t), 1.88 (2H, m), 1.40 (2H, m).

Treatment of the free base with 2 equivalents of hydrogen chloride (0.4M in 1,4-dioxane) gave the dihydrochloride salt (60 mg).

Example 62

(4R)-3-Fluoro-4-[(4-{[(2-oxo-2,3-dihydro-1H-pyrido[2,3-b][1,4]thiazin-7-yl)methyl]amino}-1-piperidinyl)methyl]-4,5-dihydro-7H-pyrrolo[3,2,1-de]-1,5-naphthyridin-7-one Hydrochloride

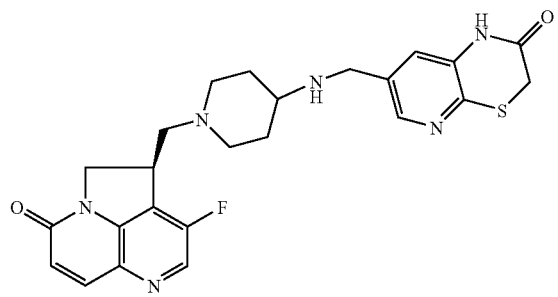

(4R)-4-[(4-amino-1-piperidinyl)methyl]-3-fluoro-4,5-dihydro-7H-pyrrolo[3,2,1-de]-1,5-naphthyridin-7-one Enantiomer 1 (50 mg, 0.166 mmol) and 2-oxo-2,3-dihydro-1H-pyrido[2,3-b][1,4]thiazine-7-carboxaldehyde (for a synthesis see WO2004058144 Example 48(e)) (32 mg, 0.166 mol) were stirred in chloroform (1 mL) and methanol (1 mL) for 2 h at room temperature. Sodium cyanoborohydride (40 g) was added and the mixture was stirred for 18 h. The mixture was filtered and evaporated. Chromatography on silica, eluting with 0-20% methanol/dichloromethane, gave the free base of the title compound (31 mg, 39%).

MS (+ve ion electrospray): m/z 481 [MH⁺].

Treatment of the free base with 1 equivalent of hydrogen chloride (0.4M in 1,4-dioxane) gave the hydrochloride salt Example 63

3-Chloro-4-[(4-[(5-oxo-1,2,3,5-tetrahydro-7-indolizinyl)methyl]amino)-1-piperidinyl)methyl]-4,5-dihydro-7H-pyrrolo[3,2,1-de]-1,5-naphthyridin-7-one hydrochloride

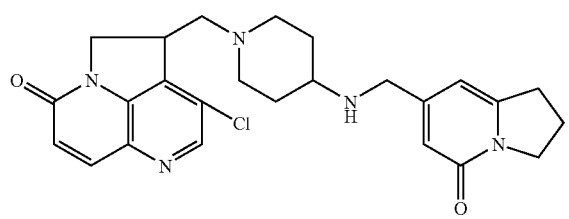

(a) 2-Chloro-4-({[(1,1-dimethylethyl)(dimethyl)silyl]oxy}methyl)-6-(methyloxy)pyridine A solution of [2-chloro-6-(methyloxy)-4-pyridinyl]methanol (for a synthesis see Adamczyk, M.; Akireddy, S. R.; Reddy, Rajarathnam E. Tetrahedron 2002, 58(34), 6951)(8.02 g, 46.22 mmol) in dry DMF (100 ml) was treated with tert-butyldimethylsilyl chloride (8.36 g, 55.46 mmol) and imidazole (3.77 g, 55.46 mmol) and stirred at rt for 2 h. The reaction mixture was treated with water extracted three times with dichloromethane, dried (magnesium sulphate), evaporated and chromatographed on silica gel (100 g), eluting with 1:4 ethyl acetate-hexane to give the desired product (12.38 g, 93%).

MS (+ve ion electrospray) m/z 288/290 (MH⁺).

(b) Butyl (2E)-3-[4-({[(1,1-dimethylethyl)(dimethyl)silyl]oxy}methyl)-6-(methyloxy)-2-pyridinyl]-2-propenoate A solution of 2-chloro-4-({[(1,1-dimethylethyl)(dimethyl)silyl]oxy}methyl)-6-(methyloxy)pyridine (9.20 g, 32.01 mmol) in 1,4-dioxane (100 ml) was treated with Pd(Pt-Bu₃)₂ (327 mg, 0.64 mmol), Pd₂(dba)₃ (293 mg, 0.32 mmol), Cy₂NMe (7.53 ml, 35.21 mmol) and n-butyl acrylate (5.96 ml, 41.62 mmol). The reaction was heated at 120° C. for 1 h and was then treated with water extracted 3× with diethyl ether, dried (magnesium sulphate), evaporated and chromatographed on silica gel (250 g), eluting with 1:4 ethyl acetate-hexane to give the desired product (8.25 g, 68%).

MS (+ve ion electrospray) m/z 380 (MH⁺).

(c) Butyl 3-[4-({[(1,1-dimethylethyl)(dimethyl)silyl]oxy}methyl)-6-(methyloxy)-2-pyridinyl]propanoate A mixture of butyl (2E)-3-[4-({[(1,1 dimethylethyl)(dimethyl)silyl]oxy}methyl)-6-(methyloxy)-2-pyridinyl]-2-propenoate (4.84 g, 12.49 mmol) and 10% palladium on carbon in methanol (200 ml) was stirred at rt over one atmosphere of hydrogen for 3 h. The mixture was filtered through Celite and evaporated to give the desired product (4.76 g, 98%).

MS (+ve ion electrospray) m/z 382 (MH⁺).

(d) 3-[4-({[(1,1-Dimethylethyl)(dimethyl)silyl]oxy}methyl)-6-(methyloxy)-2-pyridinyl]-1-propanol A solution of butyl 3-[4-({[(1,1-dimethylethyl)(dimethyl)silyl]oxy}methyl)-6-(methyloxy)-2-pyridinyl]propanoate (4.76 g, 12.49 mmol) in THF (120 ml) was treated with LiAlH₄ soln (1M in THF, 12.49 ml, 12.49 mmol) at −78° C. The reaction mixture was allowed warm to −20° C. and after stirring at −20° C. for 15 min, the mixture was treated with water (9 ml) and allowed to stir for 1 h before being filtered and evaporated to give a slightly impure product (3.98 g, 102%).

MS (+ve ion electrospray) m/z 312 (MH⁺).

(e) 7-({[(1,1-dimethylethyl)(dimethyl)silyl]oxy}methyl)-2,3-dihydro-5(1H)-indolizinone A solution of 3-[4-({[(1,1-dimethylethyl)(dimethyl)silyl]oxy}methyl)-6-(methyloxy)-2-pyridinyl]-1-propanol (5.16 g, 16.59 mmol) in dichloromethane (250 ml) was treated with pyridine (2.94 ml, 36.47 mmol) and trifluoromethanesulfonic anhydride (3.1 ml, 19.88 mmol) and stirred at room temperature for 10 min before being treated with tetrabutylammonium iodide (30.61 g, 82.95 mmol) and stirred at room temperature for a further 4 h. Water was then added and the mixture was extracted three times with diethyl ether and the combined organic extracts washed again with water. The organic extracts were dried with magnesium sulphate and evaporated. The residue was chromatographed on silica eluting with 0-10% methanol in dichloromethane to give the desired product (3.93 g, 14.09 mmol)

MS (+ve ion electrospray) m/z 280 (MH+).

(i) 7-(hydroxymethyl)-2,3-dihydro-5(1H)-indolizinone

A solution of 7-({[(1,1-dimethylethyl)(dimethyl)silyl]oxy}methyl)-2,3-dihydro-5(1H)-indolizinone (3.93 g, 14.09 mmol) in tetrahydrofuran (100 ml) was treated with acetic acid (1.61 ml, 28.17 mmol) and tetrabutylammonium fluoride (1M in THF, 21 ml, 21.13 mmol) and stirred at room temperature for 1 h before being evaporated. The residue was chromatographed on silica eluting with 0-20% methanol in dichloromethane to give the desired product (1.87 g, 80%)

MS (+ve ion electrospray) m/z 166 (MH+).

(g) 5-oxo-1,2,3,5-tetrahydro-7-indolizinecarbaldehyde

A solution of 7-(hydroxymethyl)-2,3-dihydro-5(1H)-indolizinone (237 mg, 1.44 mmol) in acetone (12 ml) was treated with IBX (603 mg, 2.16 mmol) and heated at reflux for 1 h. The mixture was then evaporated, dissolved in dichloromethane and filtered, redissolved in dichloromethane and filtered again to provide the slightly impure desired product (238 mg, 101%)

MS (+ve ion electrospray) m/z 164 (MH+).

(h) Title Compound

4-[(4-amino-1-piperidinyl)methyl]-3-chloro-4,5-dihydro-7H-pyrrolo[3,2,1-de]-1,5-naphthyridin-7-one Enantiomer 1 (111 mg, 0.349 mmol) and 5-oxo-1,2,3,5-tetrahydro-7-indolizinecarbaldehyde (57 mg, 0.349 mol) were heated at reflux in chloroform (5 mL) and DMF (0.2 mL) for 2 h before cooling to room temperature and addition of NaBH(OAc)3 (150 mg, 0.708 mmol). The mixture was then stirred for 0.5 h at room temperature and for 1 h at 50° C. The mixture was cooled, filtered and evaporated. Chromatography on silica, eluting with 0-20% methanol/dichloromethane, gave the free base of the title compound (99 mg, 61%).

MS (+ve ion electrospray) m/z 466 (MH+). δH (CDCl3, 400 MHz) 1.35-1.50 (2H, m), 1.80-1.95 (2H, m), 2.2-2.15 (1H, m) 2.15-2.35 (3H, m), 2.45-2.60 (2H, m), 2.70-2.75 (1H, m), 2.95-3.11 (4H, m), 3.55 (2H, s), 3.94-4.08 (1H, m), 4.10-4.14 (2H, t), 4.40-4.42 (1H, m), 4.52-4.60 (1H, m), 6.21 (1H, s), 6.33 (1H, s), 6.86 (1H, d), 7.88 (1H, d), 8.35 (1H, m).

The free base of the title compound in methanol and chloroform was converted to the hydrochloride salt by adding an equivalent of 4M hydrogen chloride in 1,4-dioxane, followed by evaporation to dryness.

Example 64

3-Chloro-4-[(4-{[(2-methyl-1-oxo-1,2,3,4-tetrahydro-7-isoquinolinyl)methyl]amino}-1-piperidinyl)methyl]-4,5-dihydro-7H-pyrrolo[3,2,1-de]-1,5-naphthyridin-7-one hydrochloride

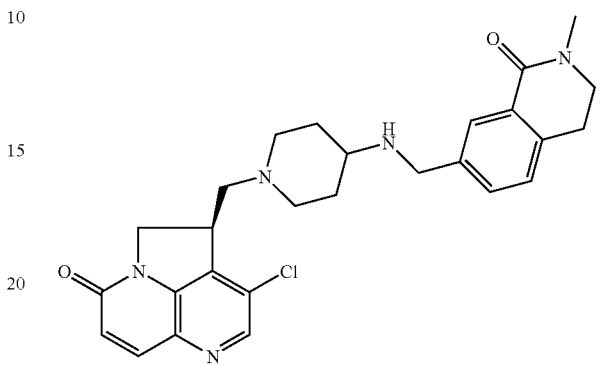

(a) 7-bromo-3,4-dihydro-1(2H)-isoquinolinone

To a solution of 7-amino-3,4-dihydro-1(2H)-isoquinolinone, (0.77 g, 4.77 mmol)(for a synthesis see Girard, Yves; Atkinson, Joseph G.; Belanger, Patrice C.; Fuentes, Jose J.; Rokach, Joshua; Rooney, C. Stanley; Remy, David C.; Hunt, Cecilia A *J. Org. Chem.* (1983), 48(19), 3220) in acetonitrile (10 ml) at 0° C. was added 48% aqueous HBr (10 ml, pre-cooled to 0° C.). The mixture was stirred at 0° C. for 0.5 h before addition of a solution of NaNO2 (0.379 g, 5.49 mmol) in water (2 ml) over 0.4 h. The reaction was then stirred at 0° C. for 0.5 h and then CuBr (0.822 g, 5.726 mmol) was added portionwise over 10 min. The reaction mixture was then warmed to room temperature, stirred at room temperature for 0.5 h and then at 70° C. for 1 h. The reaction mixture was then cooled to 0° C., water (60 ml) was added and the mixture stirred at 0° C. for 1 h before filtering and drying in vacuo. The residue was dissolved in 10% methanol/dichloromethane, dried with magnesium sulphate and evaporated to give the desired product (0.679 g, 63%).

MS (+ve ion electrospray) m/z 227 (MH+).

(b) 7-ethenyl-3,4-dihydro-1(2H)-isoquinolinone

A solution of 7-bromo-3,4-dihydro-1(2H)-isoquinolinone (0.679 g, 3.004 mmol) and tetrakis(triphenylphosphine)palladium(0) (174 mg, 0.150 mmol) in 1,2-dimethoxyethane (30 ml) was stirred at room temperature for 0.5 h before addition of 2,4,6-trivinylcyclotriboroxane.pyridine complex (for a synthesis see Kerins, Fergal; O'Shea, Donal F. *J. Org. Chem.* (2002), 67(14), 4968) (295 mg, 1.218 mmol), K2CO3 (415 mg, 3.004 mmol) and water (10 ml). The reaction was heated at reflux for 1.5 h before cooling to room temperature and addition of water (50 ml). The mixture was extracted with 10% methanol/dichloromethane (3×100 ml), the organic layers were dried with magnesium sulphate and evaporated. Chromatography on silica, eluting with 0-100% ethyl acetate/hexane, gave the product (456 mg, 88%).

MS (+ve ion electrospray) m/z 173 (MH+).

(c) 7-ethenyl-2-methyl-3,4-dihydro-1(2H)-isoquinolinone

To a solution of 7-ethenyl-3,4-dihydro-1(2H)-isoquinolinone (224 mg, 1.295 mmol) in toluene (2 ml) and tetrahydrofuran (2 ml) at 0° C. was added sodium hydride (60% in oil, 37 mg, 1.554 mmol). The reaction mixture was warmed to room temperature and stirred for 0.5 h before addition of iodomethane (242 µl, 3.885 mmol). The reaction mixture was stirred at room temperature for 1 h before addition of additional iodomethane (242 µl, 3.885 mmol). The reaction mixture was then stirred at room temperature for a further 1 h before addition of water (20 ml). The mixture was extracted with 10% methanol/dichloromethane (3×100 ml), the organic layers were dried with magnesium sulphate and evaporated. Chromatography on silica, eluting with 0-100% ethyl acetate/hexane, gave the product (181 mg, 75%).

MS (+ve ion electrospray) m/z 188 (MH+).

(d) 2-methyl-1-oxo-1,2,3,4-tetrahydro-7-isoquinolinecarbaldehyde

To a solution of 7-ethenyl-2-methyl-3,4-dihydro-1(2H)-isoquinolinone (181 mg, 0.968 mmol) in 1,4-dioxane (I 5 ml) and water (3 ml) at 0° C. was added sodium periodate (476 mg, 2.226 mmol) and osmium tetroxide (1.1 ml of a 4% aqueous solution). The reaction mixture was warmed to room temperature and stirred for 0.5 h before evaporation of the reaction mixture. The residue was dissolved in 1,4-dioxane (20 ml) and evaporated again. The mixture was then dissolved in dichloromethane (100 ml), dried with magnesium sulphate and evaporated. Chromatography on silica, eluting with 0-100% Ethyl Acetate/Hexane, gave the product (136 mg, 74%).

MS (+ve ion electrospray) m/z 190 (MH+).

(e) Title Compound

4-[(4-amino-1-piperidinyl)methyl]-3-chloro-4,5-dihydro-7H-pyrrolo[3,2,1-de]-1,5-naphthyridin-7-one Enantiomer 1 (133 mg, 0.418 mmol) and 2-methyl-1-oxo-1,2,3,4-tetrahydro-7-isoquinolinecarbaldehyde (79 mg, 0.418 mmol) were stirred in chloroform (5 mL) and methanol (0.5 mL) for 1 h at room temperature before addition of NaBH(OAc)$_3$ (266 mg, 1.254 mmol). The mixture was then stirred for 0.5 h at room temperature and before addition of sat. aqueous NaHCO$_3$ (50 ml). The mixture was extracted with 10% methanol/dichloromethane (3×100 ml), the organic layers were dried with magnesium sulphate and evaporated. Chromatography on silica, eluting with 0-20% methanol/dichloromethane, gave the product (79 mg, 39%).

MS (+ve ion electrospray) m/z 492 (MH+). δH (CDCl$_3$, 400 MHz) 1.36-1.49 (2H, m), 1.82-1.95 (2H, m), 2.08-2.12 (1H, m) 2.21-2.31 (1H, m), 2.40-2.59 (2H, m), 2.65-2.75 (1H, m), 2.96-3.08 (4H, m), 3.15 (3H, s), 3.55-3.57 (2H, t), 3.85 (2H, s), 3.94-4.08 (1H, m), 4.38-4.42 (1H, m), 4.53-4.60 (1H, m), 6.86 (1H, d), 7.14 (1H, d), 7.41 (1H, d), 7.88 (1H, d), 7.99 (1H, s), 8.40 (1H, s).

The free base of the title compound in methanol and chloroform was converted to the hydrochloride salt by adding an equivalent of 4M hydrogen chloride in 1,4-dioxane, followed by evaporation to dryness.

Example 65

(4R)-3-Fluoro-4-[(4-{[(3-oxo-3,4-dihydro-2H-1,4-benzoxazin-6-yl)methyl]amino}-1-piperidinyl)methyl]-4,5-dihydro-7 if-pyrrolo[3,2,1-de]-1,5-naphthyridin-7-one Dihydrochloride

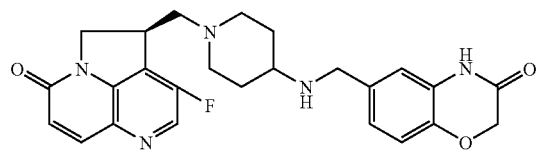

A mixture of (4R)-4-[(4-amino-1-piperidinyl)methyl]-3-fluoro-4,5-dihydro-7H-pyrrolo[3,2,1-de]-1,5-naphthyridin-7-one Enantiomer 1 (50 mg, 0.16 mmol) and 3-oxo-3,4-dihydro-2H-benzo[1,4]oxazine-6-carboxaldehyde (for a synthesis see WO2002056882, Example 5(b)) (29 mg, 016 mmol) in anhydrous dichloromethane (1.5 mL) and anhydrous methanol (0.1 mL) was treated with triacetoxyborohydride (105 mg, 0.49 mmol). The reaction mixture was stirred at room temperature, under argon, for 20 hours. Solvents were evaporated and then chromatographed on silica eluting with a 0-100% gradient of dichloromethane in ethyl acetate then a 0-20% gradient of methanol in ethyl acetate to afford the free base of the title compound as a white solid (10 mg, 13%).

MS (+ve ion electrospray) m/z 492 (MH+).

The free base of the title compound was converted to the dihydrochloride salt (15 mg) by adding an excess of 1M HCl in diethyl ether then evaporating to dryness.

Example 66

(4R)-4-[(4-{[(7-Chloro-3-oxo-3,4-dihydro-2H-pyrido[3,2-b][1,4]oxazin-6-yl)methyl]amino}-1-piperidinyl)methyl]-3-fluoro-4,5-dihydro-7H-pyrrolo[3,2,1-de]-1,5-naphthyridin-7-one Hydrochloride

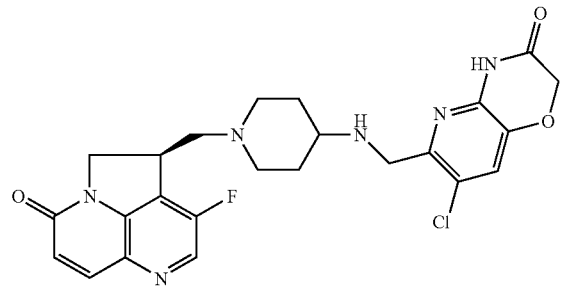

A mixture of (4R)-4-[(4-amino-1-piperidinyl)methyl]-3-fluoro-4,5-dihydro-7H-pyrrolo[3,2,1-de]-1,5-naphthyridin-7-one Enantiomer 1 (50 mg, 016 mmol) and 7-chloro-3-oxo-3,4-dihydro-2H-pyrido[3,2-b][1,4]oxazine-6-carboxaldehyde (for a synthesis see WO2003064421, Example 15(c)) (33 mg, 0.16 mmol) in anhydrous dichloromethane (1.5 mL) and anhydrous methanol (0.1 mL) was treated with triacetoxyborohydride (105 mg, 0.49 mmol). After 16 hours, an aqueous solution of sodium bicarbonate was added. The free base of the title compound came out of solution and was isolated by filtration, washed with water and dried in vacuo (50 mg, 60%).

MS (+ve ion electrospray) m/z 492 (MH+).

The free base of the title compound was converted to the hydrochloride salt by dissolving in chloroform and adding an excess of 1M HCl/diethyl ether then evaporating to dryness.

Example 67

(4R)-3-Fluoro-4-[(4-{[(8-fluoro-2,3-dihydro-1,4-benzodioxin-6-yl)methyl]amino}-1-piperidinyl)methyl]-4,5-dihydro-7H-pyrrolo[3,2,1-de]-1,5-naphthyridin-7-one hydrochloride

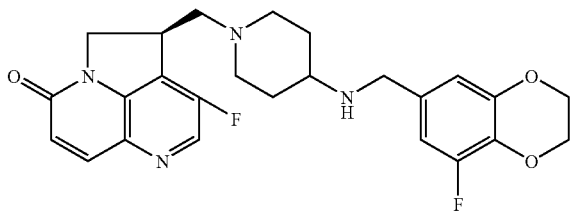

A mixture of (4R)-4-[(4-amino-1-piperidinyl)methyl]-3-fluoro-4,5-dihydro-7H-pyrrolo[3,2,1-de]-1,5-naphthyridin-7-one Enantiomer 1 (50 mg, 016 mmol) and 8-fluoro-2,3-dihydro-1,4-benzodioxin-6-carboxaldehyde (33 mg, 0.16 mmol) in anhydrous dichloromethane (1.5 mL) and anhydrous methanol (0.1 mL) was treated with triacetoxyborohydride (105 mg, 0.49 mmol). After 18 hours, the reaction mixture was worked-up and the residue was chromatographed (20 g of silica) on silica eluting with a 0-30% gradient of methanol in dichloromethane affording the free base of the title compound (24 mg, 31%).

MS (+ve ion electrospray) m/z 492 (MH+).

The free base of the title compound was converted to the hydrochloride salt by dissolving in methanol and adding 0.3 mL of 1M HCl/diethyl ether then evaporating to dryness Example 68

(4R)-4-[(4-{[(7-Bromo-3-oxo-3,4-dihydro-2H-pyrido[3,2-b][1,4]thiazin-6-yl)methyl]amino}-1-piperidinyl)methyl]-3-fluoro-4,5-dihydro-7H-pyrrolo[3,2,1-de]-1,5-naphthyridin-7-one Enantiomer 1 Dihydrochloride

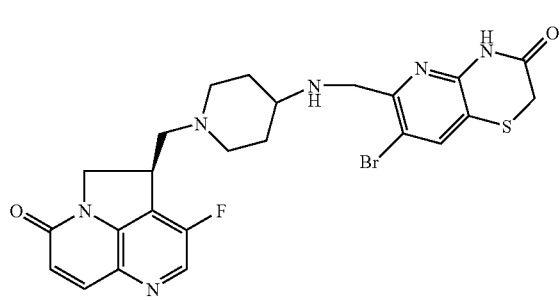

A mixture of (4R)-4-[(4-amino-1-piperidinyl)methyl]-3-fluoro-4,5-dihydro-7H-pyrrolo[3,2,1-de]-1,5-naphthyridin-7-one Enantiomer 1 (50 mg; 0.165 mmol), 7-bromo-3-oxo-3,4-dihydro-2H-pyrido[3,2-b][1,4]thiazine-6-carboxaldehyde (for a synthesis, see WO 2002056882 Example 33(e)) (45 mg; 0.1656 mmol) in methanol (1 ml), chloroform (1 ml) and acetic acid (3 drops) was heated at 70° C. for 3 hours with 3A molecular sieves. It was cooled, sodium cyanoborohydride (40 mg; 0.635 mmol) was added, and the mixture was stirred at room temperature overnight. Sodium carbonate solution was added and the solution was extracted with 10% methanol-chloroform, dried (sodium sulphate), evaporated and chromatographed on silica, eluting with 10% methanol-dichloromethane to afford the free base of the title compound (62 mg)

MS (ES+) m/z 559/561 (MH+).

The free base of the title compound was converted to the dihydrochloride by dissolving in chloroform-methanol, adding excess 4M HCl in 1,4-dioxane and then evaporating to dryness. The residue was triturated with ether to give a solid (51 mg), with MS as that of free base.

Example 69

4-({(3S,4R)-4-[([1,3]oxathiolo[5,4-c]pyridin-6-ylmethyl)amino]-3-hydroxy-1-piperidinyl}methyl)-3-fluoro-4,5-dihydro-7H-pyrrolo[3,2,1-de]-1,5-naphthyridin-7-one Diastereomer 1 Hydrochloride

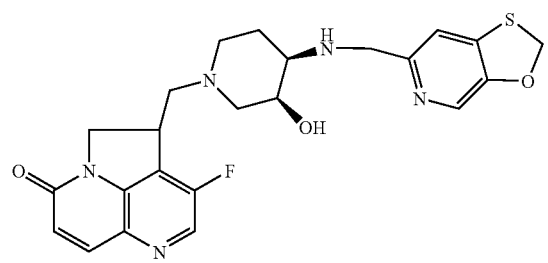

(a) Racemic methyl 2-[3-fluoro-6-(methyloxy)-1,5-naphthyridin-4-yl]-3-[(3S,4R)-4-({[(1,1-dimethylethyl)oxy]carbonyl}amino-3-hydroxy-1-piperidinyl}propanoate A mixture of methyl 2-[3-fluoro-6-(methyloxy)-1,5-naphthyridin-4-yl]-2-propenoate (27.96 g, 107 mmol), 1,1-dimethylethyl[(3S,4R)-3-hydroxy-4-piperidinyl]carbamate (for a synthesis see WO2004058144, Example 5(c), cis-(3-hydroxy-piperidin-4-yl-carbamic acid tert-butyl ester Enantiomer 2) (25 g, 116 mmol) and 1,1,3,3-tetramethylguanidine (2.5 ml) in DMF (122 ml) was heated at 80° C. under argon for 6 hours, cooled, evaporated and kept under high vacuum for 3 days. Chromatography of the residue (eluting with a methanol/dichloromethane gradient) gave the product (57.7 g), about 90% pure (major impurity DMF).

MS (ES+) m/z 479 (MH+, 100%).

(b) Racemic 1,1-dimethylethyl((3S,4R)-1-{2-[3-fluoro-6-(methyloxy)-1,5-naphthyridin-4-yl]-3-hydroxypropyl}-3-hydroxy-4-piperidinyl)carbamate A solution of racemic methyl 2-[3-fluoro-6-(methyloxy)-1,5-naphthyridin-4-yl]-3-[(3S,4R)-4-({[(1,1-dimethylethyl)oxy]carbonyl}amino-3-hydroxy-1-piperidinyl)propanoate (107 mmol) in THF (1200 ml) at −70° C. under argon was treated over 10 minutes with a 1M solution of lithium aluminium hydride in THF (123 ml), allowed to warm to −20° C. and stirred in an ice bath for 2 hours. The mixture was treated with water (9.22 ml), 2N NaOH solution (17.3 ml) and water (19.9 ml), stirred 1 hour and filtered through kieselguhr. The filtrate was evaporated and the residue chromatographed using a methanol/dichloromethane gradient to give the product (34.28 g, 71%).

MS (ES+) m/z 451 (MH+, 100%).

(c) Racemic 1,1-dimethylethyl{(3S,4R)-1-[(3-fluoro-7-oxo-4,5-dihydro-7H-pyrrolo[3,2,1-de]-1,5-naphthyridin-4-yl)methyl]-3-hydroxy-4-piperidinyl}carbamate To a solution of racemic 1,1-dimethylethyl((3S,4R)-1-{2-[3-fluoro-6-(methyloxy)-1,5-naphthyridin-4-yl]-3-hydroxypropyl}-3-hydroxy-4-piperidinyl)carbamate (2 g, 4.45 mmol) in chloroform (23 ml) at 0° C. was added diisopropylethylamine (1.74 ml, 10 mmol) and toluenesulfonic anhydride (1.67 g, 5.13 mmol). The reaction was warmed to room temperature while stirring for 2 h and heated at 50° C. for 3 days, when LCMS indicated an essentially complete reaction. The solution was washed with aqueous sodium bicarbonate solution, the aqueous phase was extracted twice with chloroform and the combined organic phases were dried and the solvent was removed. The residue was subjected to column chromatography on silica gel using a dichloromethane and methanol gradient to provide the desired compound (1.093 g, 59%).

MS (ES+) m/z 419 (MH+, 40%), 319 (100%).

(d) Racemic 4-{[(3S,4R)-4-amino-3-hydroxy-1-piperidinyl]methyl}-3-fluoro-4,5-dihydro-7H-pyrrolo[3,2,1-de]-1,5-naphthyridin-7-one A solution of racemic 1,1-dimethylethyl{(3S,4R)-1-[(3-fluoro-7-oxo-4,5-dihydro-7H-pyrrolo[3,2,1-de]-1,5-naphthyridin-4-yl)methyl]-3-hydroxy-4-piperidinyl}carbamate (15.57 g) in dichloromethane (170 ml) was cooled in ice-water, treated with trifluoracetic acid (137 ml), stirred 1 hour at room temperature and evaporated to dryness. After keeping under high vacuum for 1 hour, the crude material was dissolved in methanol and run through a column of Amberlyst A21 basic resin (500 ml) (Sigma-Aldrich Co.), eluting with methanol. The solution containing the product was evaporated and the residue chromatographed on silica gel, eluting with dichloromethane/methanol/0.88 ammonia (9:1:0.1) to give product (8.96 g, 76%).

(e) 4-{[(3S,4R)-4-Amino-3-hydroxy-1-piperidinyl]methyl}-3-fluoro-4,5-dihydro-7H-pyrrolo[3,2,1-de]-1,5-naphthyridin-7-one Diastereomer 1 and Diastereomer 2

Racemic 4-{[(3S,4R)-4-amino-3-hydroxy-1-piperidinyl]methyl}-3-fluoro-4,5-dihydro-7H-pyrrolo[3,2,1-de]-1,5-naphthyridin-7-one (9.4 g) was subjected to preparative HPLC on Chiralpak AD. This procedure gave the faster running diastereomer (Diastereomer 1, 4.7 g) in >99% de and the slower running diastereomer (Diastereomer 2, 4.2 g) in 99% de.

(f) Title Compound

A mixture of 4-{[(3S,4R)-4-amino-3-hydroxy-1-piperidinyl]methyl}-3-fluoro-4,5-dihydro-7H-pyrrolo[3,2,1-de]-1,5-naphthyridin-7-one Diastereomer 1 (60 mg, 0.188 mmol), [1,3]oxathiolo[5,4-c]pyridine-6-carbaldehyde (for a synthesis see WO2004058144, Example 61) (26.2 mg, 0.157 mmol) and 3A molecular sieves in chloroform (1 ml) and methanol (1 ml) was heated at 65° C. for 4 h, cooled and then sodium triacetoxyborohydride (66.5 mg, 0.314 mmol) was added. The reaction was stirred at room temperature for 18 h, filtered through kieselguhr and evaporated. The residue was treated with aqueous sodium bicarbonate solution and a 4:1 dichloromethane:methanol mixture, shaken and separated. The aqueous phase was extracted with a 4:1 dichloromethane:methanol mixture and then the combined organic phases were dried and the solvent was removed under reduced pressure. The residue was subjected to column chromatography on silica gel with dichloromethane/methanol/0.88 ammonia 95:5:0.5 to provide the free base of the title compound (51 mg, 69%).

¹H NMR δ (CDCl₃) 1.5-2.0 (m including exchangeables), 2.25-2.35 (2H, m), 2.55-2.65 (2H, m), 2.82 (1H, broad d), 2.89 (1H, dd, J 13 and 6 Hz), 3.02 (1H, broad d), 3.87 (3H, s), 4.05-4.15 (1H, m), 4.40 (1H, dd, J 13 and 4 Hz), 4.52 (1H, dd, J 13 and 9 Hz), 5.74 (2H, s), 6.83 (1H, d, J 10 Hz), 7.24 (1H, s), 7.89 (1H, d, J 10 Hz), 8.01 (1H, s), 8.34 (1H, d, J=1.6 Hz). MS (ES+) m/z 470 (MH+, 100%).

The free base of the title compound was converted to the hydrochloride by dissolving in chloroform and adding 1 equivalent of 1M HCl/diethyl ether then evaporating to dryness. MS as that of free base.

Example 70

4-({(3S,4R)-4-[([1,3]Oxathiolo[5,4-c]pyridin-6-ylmethyl)amino]-3-hydroxy-1-piperidinyl}methyl)-3-fluoro-4,5-dihydro-7H-pyrrolo[3,2,1-de]-1,5-naphthyridin-7-one Diastereomer 2 Hydrochloride

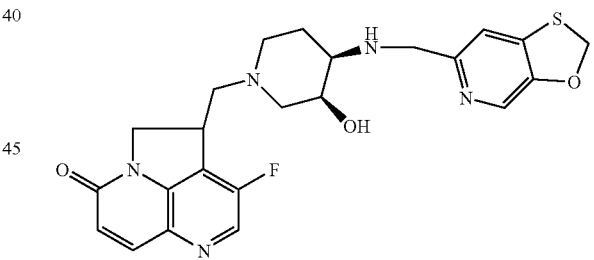

The free base of the title compound was prepared from 4-{[(3S,4R)-4-amino-3-hydroxy-1-piperidinyl]methyl}-3-fluoro-4,5-dihydro-7H-pyrrolo[3,2,1-de]-1,5-naphthyridin-7-one Diastereomer 2 and [1,3]oxathiolo[5,4-c]pyridine-6-carbaldehyde (for a synthesis see WO2004058144, Example 61) according to the general method of Example 69 in 55% yield.

MS (ES+) m/z 470 (MH+, 100%).

The free base of the title compound was converted to the hydrochloride by dissolving in chloroform and adding 1 equivalent of 1M HCl/diethyl ether, then evaporating to dryness. MS as that of free base.

Example 71

4-({(3R,4S)-4-[([1,3]Oxathiolo[5,4-c]pyridin-6-ylmethyl)amino]-3-hydroxy-1-piperidinyl}methyl)-3-fluoro-4,5-dihydro-7H-pyrrolo[3,2,1-de]-1,5-naphthyridin-7-one Diastereomer 1 Hydrochloride

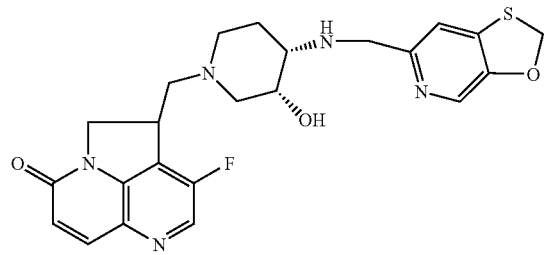

(a) 4-{[(3R,4S)-4-Amino-3-hydroxy-1-piperidinyl]methyl}-3-fluoro-4,5-dihydro-7H-pyrrolo[3,2,1-de]-1,5-naphthyridin-7-one Diastereomer 1 and Diastereomer 2

Racemic 4-{[(3R,4S)-4-amino-3-hydroxy-1-piperidinyl]methyl}-3-fluoro-4,5-dihydro-7H-pyrrolo[3,2,1-de]-1,5-naphthyridin-7-one (2.6 g) was subjected to preparative HPLC on Chiralpak AD, eluting with 60% acetonitrile/40% methanol containing 20 mmol ammonium acetate. This procedure gave the faster running diastereomer (Diastereomer 1, 850 mg) in 98% de and the slower running diastereomer (Diastereomer 2, 1.18 g) in 97% de.

(b) Title Compound

A mixture of 4-{[(3R,4S)-4-amino-3-hydroxy-1-piperidinyl]methyl}-3-fluoro-4,5-dihydro-7H-pyrrolo[3,2,1-de]-1,5-naphthyridin-7-one Diastereomer 1 (340 mg, 1.07 mmol), [1,3]oxathiolo[5,4-c]pyridine-6-carbaldehyde (for a synthesis see WO2004058144, Example 61) (131 mg, 0.787 mmol) and 3A molecular sieves in chloroform (5 ml) and methanol (5 ml) was heated at 65° C. for 4 h, cooled and then sodium triacetoxyborohydride (332 mg, 1.56 mmol) was added. The reaction was stirred at room temperature for 18 h, filtered through kieselguhr and evaporated. The residue was treated with aqueous sodium bicarbonate solution and a 4:1 dichloromethane:methanol mixture, shaken and separated. The aqueous phase was extracted with a 4:1 dichloromethane:methanol mixture and then the combined organic phases were dried and the solvent was removed under reduced pressure. The residue was subjected to column chromatography on silica gel with dichloromethane/methanol/0.88 ammonia 95:5:0.5 to provide the free base of the title compound (308 mg, containing about 7.5% by weight of dichloromethane, 77%).

$^1$H NMR δ (CDCl$_3$) 1.5-2.0 (m including exchangeables), 2.19 (1H, dt, J 11.2 and 3.2 Hz), 2.44 (1H, d, J 10.4 Hz), 2.8-3.0 (3H, m), 3.86 (3H, s), 4.05-4.15 (1H, m), 4.42 (1H, dd, J 13 and 4 Hz), 4.52 (1H, dd, J 13 and 9 Hz), 5.74 (2H, s), 6.83 (1H, d, J 10 Hz), 7.23 (1H, s), 7.89 (1H, d, J 10 Hz), 8.01 (1H, s), 8.33 (1H, d, J 1.6 Hz). MS (ES+) m/z 470 (MH$^+$, 100%).

The free base of the title compound was converted to the hydrochloride by dissolving in dichloromethane and adding 1 equivalent of 1M HCl/diethyl ether then evaporating to dryness. MS as that of free base.

Example 72

4-({(3R,4S)-4-[(2,3-dihydro[1,4]dioxino[2,3-c]pyridin-7-ylmethyl)amino]-3-hydroxy-1-piperidinyl}methyl)-3-fluoro-4,5-dihydro-7H-pyrrolo[3,2,1-de]-1,5-naphthyridin-7-one Diastereomer 1 Hydrochloride

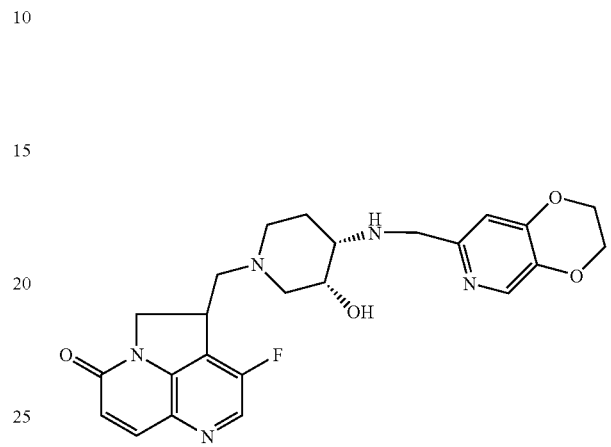

A mixture of 4-{[(3R,4S)-4-amino-3-hydroxy-1-piperidinyl]methyl}-3-fluoro-4,5-dihydro-7H-pyrrolo[3,2,1-de]-1,5-naphthyridin-7-one Diastereomer 1 (50 mg, 0.157 mmol), 2,3-dihydro[1,4]dioxino[2,3-c]pyridine-7-carboxaldehyde (for a synthesis see WO2004058144, Example 2(c)) (26 mg, 0.157 mmol) and 3A molecular sieves in chloroform (1 ml) and methanol (1 ml) was heated at 65° C. for 5 h, cooled and then sodium triacetoxyborohydride (66.5 mg, 0.314 mmol) was added. The reaction was stirred at room temperature for 18 h, filtered through kieselguhr and evaporated. The residue was treated with aqueous sodium bicarbonate solution and a 4:1 dichloromethane:methanol mixture, shaken and separated. The aqueous phase was extracted with a 4:1 dichloromethane:methanol mixture and then the combined organic phases were dried and the solvent was removed under reduced pressure. The residue was subjected to column chromatography on silica gel with dichloromethane/methanol/0.88 ammonia 95:5:0.5 to provide the free base of the title compound (24 mg, 33%).

$^1$H NMR δ (CDCl$_3$) 1.5-2.0 (m including exchangeables), 2.15-2.25 (1H, m), 2.45 (1H, d, J 11.6 Hz), 2.55-2.65 (2H, m), 2.8-3.0 (3H, m), 3.84 (3H, s), 4.05-4.15 (1H, m), 4.25-4.35 (4H, m), 4.42 (1H, dd, J 13 and 5 Hz), 4.52 (1H, dd, J 13 and 9 Hz), 6.81-6.85 (2H, m), 7.89 (1H, d, J 10 Hz), 8.11 (1H, s), 8.33 (1H, d, J 1.6 Hz). MS (ES+) m/z 468 (MH$^+$, 100%).

The free base of the title compound was converted to the hydrochloride by dissolving in dichloromethane and adding 1 equivalent of 1M HCl/diethyl ether then evaporating to dryness. MS as that of free base.

Example 73

4-({(3R,4S)-4-[(2,3-Dihydro[1,4]oxathiino[2,3-c]pyridin-7-ylmethyl)amino]-3-hydroxy-1-piperidinyl}methyl)-3-fluoro-4,5-dihydro-7H-pyrrolo[3,2,1-de]-1,5-naphthyridin-7-one Diastereomer 1 Hydrochloride

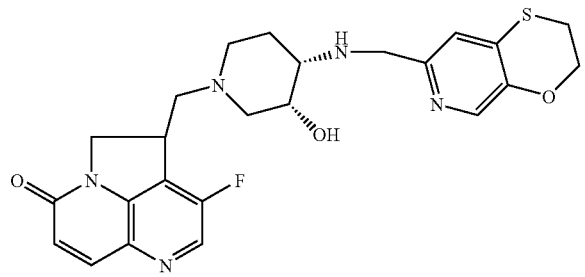

A mixture of 4-{[(3R,4S)-4-amino-3-hydroxy-1-piperidinyl]methyl}-3-fluoro-4,5-dihydro-7H-pyrrolo[3,2,1-de]-1,5-naphthyridin-7-one Diastereomer 1 (54 mg), 2,3-dihydro[1,4]oxathiino[2,3-c]pyridine-7-carbaldehyde (for a synthesis see WO2004058144, Example 60) (22.8 mg) and 3A molecular sieves in chloroform (1 ml) and methanol (1 ml) was heated at 65° C. for 5 h, cooled and then sodium triacetoxyborohydride (53 mg) was added. The general procedure of Example 72 was then followed to obtain the free base of the title compound (25 mg, 41%).

$^1$H NMR δ (CDCl$_3$) 1.5-2.0 (m including exchangeables), 2.15-2.25 (1H, m), 2.45 (1H, d, J 10.8 Hz), 2.55-2.65 (2H, m), 2.8-3.0 (3H, m), 3.15-3.19 (2H, m), 3.82 (2H, s), 3.86 (1H, broad s), 4.05-4.15 (1H, m), 4.38-4.45 (3H, m), 4.52 (1H, dd, J 13 and 9 Hz), 6.83 (1H, d, J 10 Hz), 7.03 (1H, s), 7.89 (1H, d, J 10 Hz), 8.03 (1H, s), 8.33 (1H, d, J 1.2 Hz). MS (ES+) m/z 484 (MH$^+$, 100%).

The free base of the title compound was converted to the hydrochloride by dissolving in dichloromethane and adding 1 equivalent of 1M HCl/diethyl ether then evaporating to dryness. MS as that of free base.

Example 74

3-Fluoro-4-({(3R,4S)-4-[(3,4-dihydro-2H-pyrano[2,3-c]pyridin-6-ylmethyl)amino]-3-hydroxy-1-piperidinyl}methyl)-4,5-dihydro-7H-pyrrolo[3,2,1-de]-1,5-naphthyridin-7-one Hydrochloride

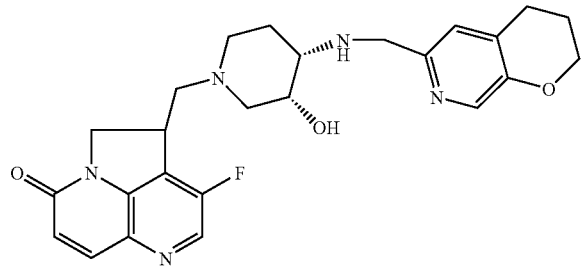

A mixture of 4-{[(3R,4S)-4-amino-3-hydroxy-1-piperidinyl]methyl}-3-fluoro-4,5-dihydro-7H-pyrrolo[3,2,1-de]-1,5-naphthyridin-7-one Diastereomer 1 (54 mg), 3,4-dihydro-2H-pyrano[2,3-c]pyridine-6-carbaldehyde (for a synthesis see WO2004058144, Example 126(c)) (20.6 mg) and 3A molecular sieves in chloroform (1 ml) and methanol (1 ml) was heated at 65° C. for 5 h, cooled and then sodium triacetoxyborohydride (53 mg) was added. The general procedure of Example 72 was then followed to obtain the free base of the title compound (41 mg, 70%).

$^1$H NMR δ (CDCl$_3$) 1.5-2.0 (m including exchangeables), 1.99-2.06 (2H, m), 2.15-2.25 (1H, m), 2.45 (1H, d, J 10.8 Hz), 2.57-2.66 (2H, m), 2.77 (2H, t, J 6.4 Hz), 2.8-2.9 (2H, m), 2.93 (1H, dd, J 12.4 and 5.2 Hz), 3.84 (2H, s), 3.86 (1H, broad s), 4.05-4.15 (1H, m), 4.22 (2H, t, J 5.2 Hz), 4.43 (1H, dd, J 13 and 4 Hz), 4.52 (1H, dd, J 13 and 9 Hz), 6.83 (1H, d, J 10 Hz), 7.00 (1H, s), 7.89 (1H, d, J 10 Hz), 8.08 (1H, s), 8.33 (1H, d, J 1.2 Hz). MS (ES+) m/z 466 (MH$^+$, 100%).

The free base of the title compound was converted to the hydrochloride by dissolving in dichloromethane and adding 1 equivalent of 1M HCl/diethyl ether then evaporating to dryness. MS as that of free base.

Example 75

(4R)-3-Fluoro-4-[(4-{[(3-oxo-3,4-dihydro-2H-1,4-benzothiazin-6-yl)methyl]amino}-1-piperidinyl)methyl]-4,5-dihydro-7H-pyrrolo[3,2,1-de]-1,5-naphthyridin-7-one Enantiomer 1 Hydrochloride

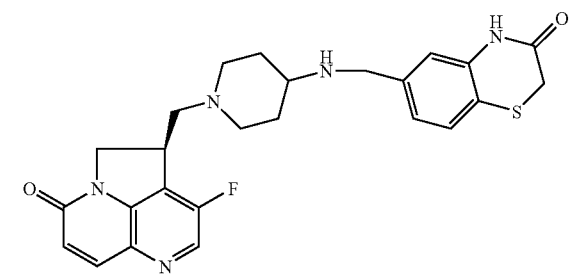

The free base of the title compound was prepared from (4R)-4-[(4-amino-1-piperidinyl)methyl]-3-fluoro-4,5-dihydro-7H-pyrrolo[3,2,1-de]-1,5-naphthyridin-7-one Enantiomer 1 and 3-oxo-3,4-dihydro-2H-benzo[1,4]thiazine-6-carboxaldehyde (for a synthesis see WO2002056882, Example 6(c)) according to the general method of Example 24(b) in 28% yield.

$^1$H NMR δ (CDCl$_3$) 1.3-1.6 (m, including exchangeables), 1.8-2.0 (2H, m), 2.11 (1H, dt), 2.24 (1H, dt), 2.45-2.65 (2H, m), 2.75-3.05 (3H, m), 3.42 (2H, s), 3.78 (2H, s), 4.0-4.15 (1H, m), 4.4-4.55 (2H, m), 6.8-6.9 (2H, m), 6.98 (1H, dd, J 8 and 1.5 Hz), 7.26 (1H, d, J 8 Hz), 7.89 (1H, d, J 10 Hz), 8.13 (1H, br s), 8.32 (1H, d, J 1.5 Hz). MS (ES+) m/z 480 (MH$^+$, 70%), 290 (100%).

The free base of the title compound was converted to the hydrochloride by dissolving in dichloromethane and adding 1 equivalent of 1M HCl/diethyl ether then evaporating to dryness. MS as that of free base.

Example 76

5-{[(1-{[(4R)-3-Fluoro-7-oxo-4,5-dihydro-7H-pyrrolo[3,2,1-de]-1,5-naphthyridin-4-yl]methyl}-4-piperidinyl)amino]methyl}-2,3-dihydro-1-benzofuran-7-carbonitrile Enantiomer 1 Hydrochloride

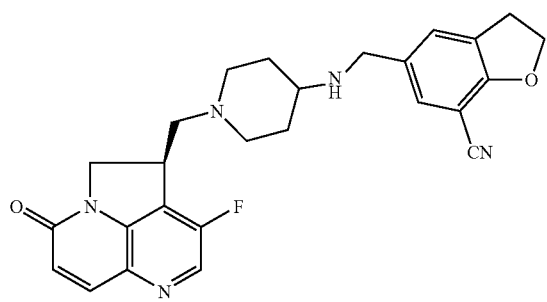

(a) 7-bromo-2,3-dihydro-1-benzofuran-5-carbaldehyde

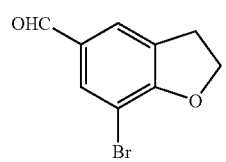

To a solution of 2,3-dihydro-1-benzofuran-5-carbaldehyde (1.0 g, 6.75 mmol) in glacial acetic acid (8 mL) was added sodium acetate (664 mg, 8.1 mmol) and bromine (0.7 ml, 13.5 mmol) at 10° C. slowly. The reaction was stirred for 2 hours at ambient temperature. The reaction was diluted with a saturated aqueous solution of sodium thiosulfate (10 mL), washed with a saturated aqueous solution of sodium bicarbonate, and then extracted with ethyl acetate. Organics were combined, dried over sodium sulfate and dried in vacuo to give the desired compound (1.4 g, 91%).

MS (+ve ion electrospray): m/z 227 (M+H)$^+$.

(b) 5-formyl-2,3-dihydro-1-benzofuran-7-carbonitrile

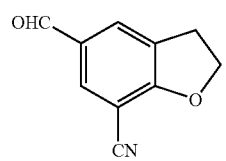

To a solution of 7-bromo-2,3-dihydro-1-benzofuran-5-carbaldehyde (1.3 g, 4.7 mmol) in dimethylacetamide (2 mL) was added copper(I) cyanide (0.41 g g, 4.7 mmol). The reaction was refluxed for 18 hours, and then concentrated under reduced pressure. The residue was washed well with warm ethyl acetate. The combined ethyl acetate layer were concentrated and dried. The crude product was purified by flash column chromatography (silica gel, 4:1 and 2:1 hexane:ethyl acetate gradient) to afford the desired product (0.5 g, 50%).

MS (+ve ion electrospray): m/z 174 (M+H)$^+$.

(c) Title Compound

A mixture of (4R)-4-[(4-amino-1-piperidinyl)methyl]-3-fluoro-4,5-dihydro-7H-pyrrolo[3,2,1-de]-1,5-naphthyridin-7-one Enantiomer 1 (50 mg, 0.17 mmol) and 5-formyl-2,3-dihydro-1-benzofuran-7-carbonitrile (30 mg, 0.17 mmol) and 3A molecular sieves in chloroform (2 ml) and methanol (2 ml) was heated at 80° C. for 5 h, cooled and then sodium triacetoxyborohydride (72 mg, 0.34 mmol) was added. The reaction was stirred at room temperature for 18 h and then the solids were filtered off and the solvent was removed under reduced pressure. The residue was subjected to column chromatography on silica gel using a dichloromethane and methanol gradient (0-20% methanol/dichloromethane) to provide the free base of the title compound (27 mg, 36%).

MS (ES+) m/z 460 (MH$^+$, 50%), 158 (100%).

The free base of the title compound was converted to the hydrochloride salt by dissolving in chloroform and adding 1 equivalent of 4M HCl/1,4-dioxane then evaporating to dryness.

Example 77

4-{[(3R,4S)-4-[(2,3-Dihydro[1,4]dioxino[2,3-c]pyridin-7-ylmethyl)amino]-3-(methyloxy)-1-piperidinyl]methyl}-3-fluoro-4,5-dihydro-7H-pyrrolo[3,2,1-de]-1,5-naphthyridin-7-one (1:1 mixture of Diastereomer 1 and Diastereomer 2) Hydrochloride

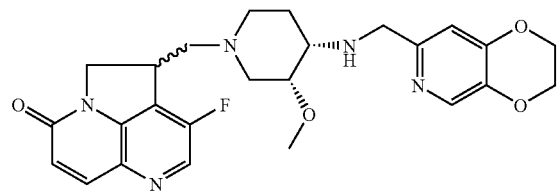

(a) Phenylmethyl (3R,4S)-4-({[(1,1-dimethylethyl)oxy]carbonyl}amino)-3-(methyloxy)-1-piperidinecarboxylate

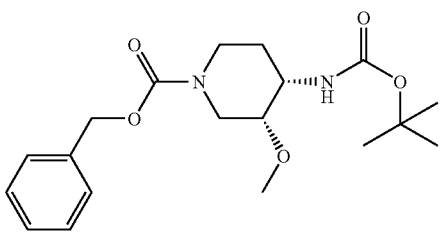

Phenylmethyl (3R,4S)-4-({[(1,1-dimethylethyl)oxy]carbonyl}amino)-3-hydroxy-1-piperidinecarboxylate (for a synthesis, see WO2004058144, Example 5 (b) cis-4-tertbutoxycarbonylamino-3-hydroxy-piperidine-1-carboxylic acid benzyl ester, Enantiomer 1) (2.2 g, 6.28 mmol) in THF (12 ml) was treated with 50% sodium hydroxide solution (12 ml), benzyltriethylammonium chloride (0.04 g) and dimethyl sulphate (1.31 g, 10.43 mmol) and stirred at RT for 60 hours. Water (100 ml) was added and the product was extracted with ethyl acetate (150 ml). The organic phase was separated and dried. Filtration and evaporation to dryness gave the title compound (2.2 g).

MS (ES+) m/z 387 (M+Na, 25%).

(b) 1,1-Dimethylethyl[(3R,4S)-3-(methyloxy)-4-piperidinyl]carbamate

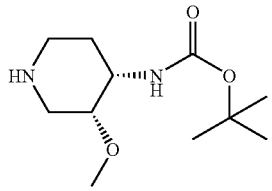

Phenylmethyl (3R,4S)-4-({[(1,1-dimethylethyl)oxy]carbonyl}amino)-3-(methyloxy)-1-piperidinecarboxylate (2.204 g, 8.3 mmol) was dissolved in ethanol (100 ml) and hydrogenated at atmospheric pressure for 18 hours over 10% palladium on carbon paste. Filtration and evaporation of the filtrate to dryness gave the title compound (1.3 g).

(c) Methyl 3-[(3R,4S)-4-({[(1,1-dimethylethyl)oxy]carbonyl}amino)-3-(methyloxy)-1-piperidinyl]-2-[3-fluoro-6-(methyloxy)-1,5-naphthyridin-4-yl]propanoate Diastereomer 1 and Diastereomer 2 Mixture

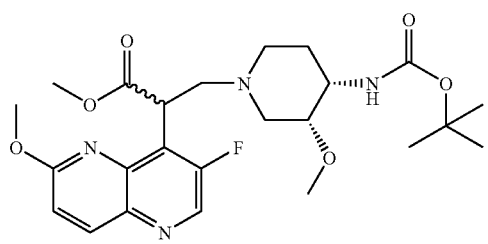

The title compound was prepared according to the general method of Example 2(d) from 1,1-dimethylethyl[(3R,4S)-3-(methyloxy)-4-piperidinyl]carbamate (1.29 g, 5.63 mmol) and methyl 2-[3-fluoro-6-(methyloxy)-1,5-naphthyridin-4-yl]-2-propenoate (1.48 g, 5.63 mmol) to give the desired product (1.98 g, 71%).

MS (ES+) m/z 493 (MH+, 100%).

(d) 1,1-Dimethylethyl[(3R,4S)-1-{2-[3-fluoro-6-(methyloxy)-1,5-naphthyridin-4-yl]-3-hydroxypropyl}-3-(methyloxy)-4-piperidinyl]carbamate Diastereomer 1 and Diastereomer 2 Mixture

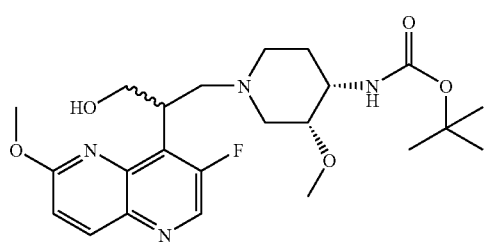

The title compound was prepared according to the general method of Example 2(e) from methyl 3-[(3R,4S)-4-({[(1,1-dimethylethyl)oxy]carbonyl}amino)-3-(methyloxy)-1-piperidinyl]-2-[3-fluoro-6-(methyloxy)-1,5-naphthyridin-4-yl]propanoate Diastereomer 1 and Diastereomer 2 mixture (1.98 g, 4 mmol) to give the desired product (0.71 g, 38%)

MS (ES+) m/z 465 (MH+, 100%).

(e) 1,1-Dimethylethyl[(3R,4S)-1-[(3-fluoro-7-oxo-4,5-dihydro-7H-pyrrolo[3,2,1-de]-1,5-naphthyridin-4-yl)methyl]-3-(methyloxy)-4-piperidinyl]carbamate Diastereomer 1 and Diastereomer 2 Mixture

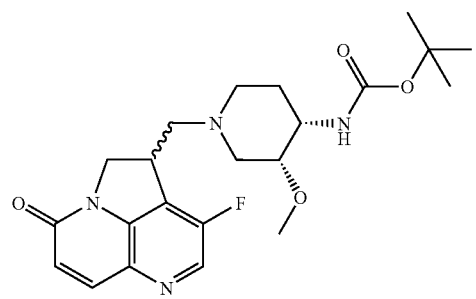

1,1-Dimethylethyl[(3R,4S)-1-{2-[3-fluoro-6-(methyloxy)-1,5-naphthyridin-4-yl]-3-hydroxypropyl}-3-(methyloxy)-4-piperidinyl]carbamate Diastereomer 1 and Diastereomer 2 mixture (0.71 g, 1.5 mmol) was dissolved in chloroform (15 ml) and treated with diisopropylethylamine (0.4 ml, 2.2 mmol) and methanesulphonic anhydride (0.31 g, 1.8 mmol) and heated under reflux for 18 hrs. The mixture was allowed to cool then washed with saturated sodium bicarbonate solution, separated then dried. Chromatography on silica gel using a methanol/dichloromethane gradient gave the title compound (0.213 g. 32%).

MS (ES+) m/z 433 (MH+, 30%).

(f) 4-{[(3R,4S)-4-Amino-3-(methyloxy)-1-piperidinyl]methyl}-3-fluoro-4,5-dihydro-7H-pyrrolo[3,2,1-de]-1,5-naphthyridin-7-one Diastereomer 1 and Diastereomer 2 Mixture

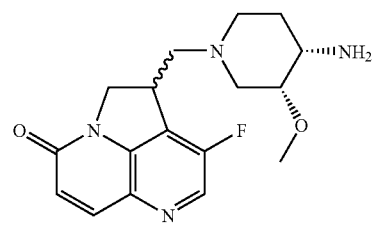

The title compound was prepared from 1,1-dimethylethyl[(3R,4S)-1-[(3-fluoro-7-oxo-4,5-dihydro-7H-pyrrolo[3,2,1-de]-1,5-naphthyridin-4-yl)methyl]-3-(methyloxy)-4-piperidinyl]carbamate Diastereomer 1 and Diastereomer 2 mixture (0.43 g, 0.99 mmol) according to the general method of Example 2(g). After evaporation of the reaction mixture the residue was dissolved in methanol and passed through Amberlyst A21 ion exchange resin then evaporated to dryness. Further purification on silica gel eluting with a dichloromethane/methanol/ammonia gradient gave the title compound (0.2 g, 60%).

MS (ES+) m/z 333 (MH+, 50%).

(g) Title Compound

The free base of the title compound was prepared from 4-{[(3R,4S)-4-amino-3-(methyloxy)-1-piperidinyl]methyl}-3-fluoro-4,5-dihydro-7H-pyrrolo[3,2,1-de]-1,5-naphthyridin-7-one Diastereomer 1 and Diastereomer 2 mixture and 2,3-dihydro[1,4]dioxino[2,3-c]pyridine-7-carboxaldehyde (for a synthesis see WO2004058144 Example 2(c)) according to the general method of Example 2(h) in 92% yield.

MS (ES+) m/z 482 (MH+, 100%).

The free base of the title compound was converted to the hydrochloride by dissolving in chloroform and adding 1 equivalent of 1M HCl/diethyl ether, then evaporating to dryness. MS as that of free base.

Example 78

4-{[(3R,4S)-4-[(3,4-Dihydro-2H-pyrano[2,3-c]pyridin-6-ylmethyl)amino]-3-(methyloxy)-1-piperidinyl]methyl}-3-fluoro-4,5-dihydro-7H-pyrrolo[3,2,1-de]-1,5-naphthyridin-7-one (1:1 mixture of Diastereomer 1 and Diastereomer 2) Hydrochloride

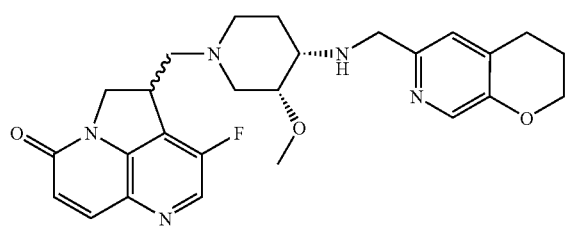

The free base of the title compound was prepared from 4-{[(3R,4S)-4-amino-3-(methyloxy)-1-piperidinyl]methyl}-3-fluoro-4,5-dihydro-7H-pyrrolo[3,2,1-de]-1,5-naphthyridin-7-one Diastereomer 1 and Diastereomer 2 mixture and 3,4-dihydro-2H-pyrano[2,3-c]pyridine-6-carbaldehyde (for a synthesis, see WO2004058144 Example 126(e)) according to the general method of Example 2(h) in 97% yield.

MS (ES+) m/z 480 (MH+, 100%).

The free base of the title compound was converted to the hydrochloride by dissolving in chloroform and adding 1 equivalent of 1M HCl/diethyl ether, then evaporating to dryness. MS as that of free base.

Example 79

3-Fluoro-4-({(3R,4S)-3-(methyloxy)-4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one (1:1 Mixture of Diastereomer 1 and Diastereomer 2) Hydrochloride

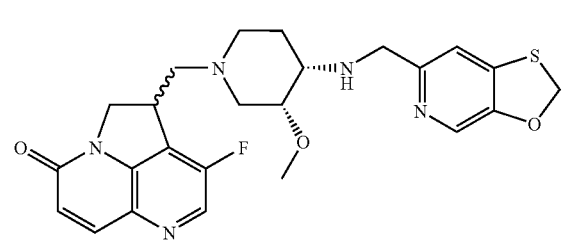

The free base of the title compound was prepared from 4-{[(3R,4S)-4-amino-3-(methyloxy)-1-piperidinyl]methyl}-3-fluoro-4,5-dihydro-7H-pyrrolo[3,2,1-de]-1,5-naphthyridin-7-one Diastereomer 1 and Diastereomer 2 mixture and [1,3]oxathiolo[5,4-c]pyridine-6-carbaldehyde (for a synthesis see WO2004058144 Example 61) according to the general method of Example 2(h) in 85% yield.

MS (ES+) m/z 484 (MH+, 100%).

The free base of the title compound was converted to the hydrochloride by dissolving in chloroform and adding 1 equivalent of 1M HCl/diethyl ether, then evaporating to dryness. MS as that of free base.

Example 80

5-({[(3R,4S)-1-[(3-Fluoro-7-oxo-4,5-dihydro-7H-pyrrolo[3,2,1-de]-1,5-naphthyridin-4-yl)methyl]-3-(methyloxy)-4-piperidinyl]amino}methyl)-2,3-dihydro-1-benzofuran-7-carbonitrile (1:1 Mixture of Diastereomer 1 and Diastereomer 2) Hydrochloride

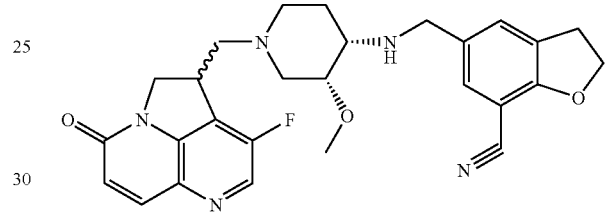

The free base of the title compound was prepared from 4-{[(3R,4S)-4-amino-3-(methyloxy)-1-piperidinyl]methyl}-3-fluoro-4,5-dihydro-7H-pyrrolo[3,2,1-de]-1,5-naphthyridin-7-one Diastereomer 1 and Diastereomer 2 mixture and 5-formyl-2,3-dihydro-1-benzofuran-7-carbonitrile according to the general method of Example 2(h) in 28% yield.

MS (ES+) m/z 490 (MH+, 80%).

The free base of the title compound was converted to the hydrochloride by dissolving in chloroform and adding 1 equivalent of 1M HCl/diethyl ether, then evaporating to dryness. MS as that of free base.

Example 81

4-[((3R,4S)-4-{[(7-bromo-2,3-dihydro-1,4-benzodioxin-6-yl)methyl]amino}-3-hydroxy-1-piperidinyl)methyl]-3-fluoro-4,5-dihydro-7H-pyrrolo[3,2,1-de]-1,5-naphthyridin-7-one Diastereomer 1 Hydrochloride

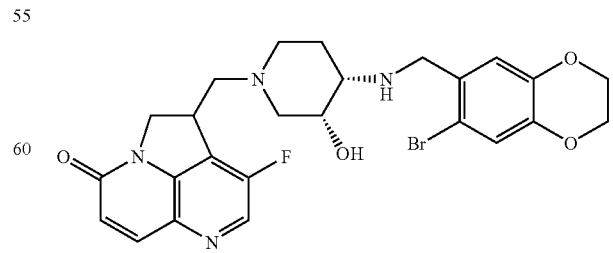

The title compound was prepared from 4-{[(3R,4S)-4-amino-3-hydroxy-1-piperidinyl]methyl}-3-fluoro-4,5-dihydro-7H-pyrrolo[3,2,1-de]-1,5-naphthyridin-7-one Diastereomer 1 and 7-bromo-2,3-dihydro-1,4-benzodioxin-6-carbaldehyde (for a synthesis see Guillaumet et al *Tetrahedron Letters* (1988), 29(22), 2665-2666) according to the general method of Example 2(h) in 72% yield.

MS (ES+) m/z 545 and 547 (MH+, 90 and 100% respectively).

Example 82

4-({(3R,4S)-4-[(5,6-Dihydro-4H-cyclopenta[b]thien-2-ylmethyl)amino]-3-hydroxy-1-piperidinyl}methyl)-3-fluoro-4,5-dihydro-7H-pyrrolo[3,2,1-de]-1,5-naphthyridin-7-one Diastereomer 1 Hydrochloride

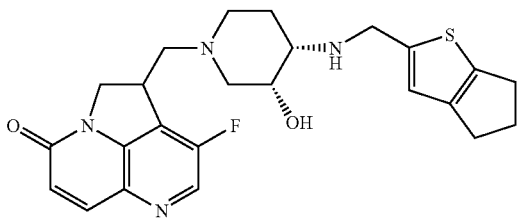

(a) 5,6-dihydro-4H-cyclopenta[b]thiophene-2-carbaldehyde

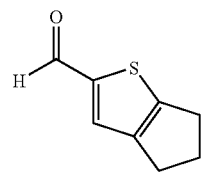

5,6-dihydro-4H-cyclopenta[b]thiophene-2-carboxylic acid (commercially available: Matrix Chemicals) (0.5 g, 2.97 mmol) was suspended in dry diethyl ether (16 ml) and treated dropwise with a solution of lithium aluminium hydride (1.0 M solution in diethyl ether, 4.0 ml, 4.0 mol). The mixture was heated to reflux for 3 h and then cooled, treated dropwise with water (1.0 ml), then 1M HCl to dissolve the precipitated white solid. The product was extracted into diethyl ether (3×10 ml), dried over anhydrous magnesium sulphate and evaporated to afford 5,6-dihydro-4H-cyclopenta[b]thien-2-ylmethanol as a white solid (420 mg). This was dissolved in dichloromethane (60 ml) and treated with manganese dioxide (2.0 g). After stirring at room temperature overnight, the mixture was filtered through Kieselguhr and the solvent evaporated to afford the title compound as a yellow oil, (0.295 g, 64%).

MS (AP+) m/z 153 (MH+, 100%).

(b) Title Compound

The title compound was prepared from 4-{[(3R,4S)-4-amino-3-hydroxy-1-piperidinyl]methyl}-3-fluoro-4,5-dihydro-7H-pyrrolo[3,2,1-de]-1,5-naphthyridin-7-one Diastereomer 1 and 5,6-dihydro-4H-cyclopenta[b]thiophene-2-carbaldehyde according to the general method of Example 2(h) in 53% yield.

MS (ES+) m/z 455 (MH+, 20%).

Example 83

(4R)-3-Fluoro-4-[(4-{[(7-fluoro-3-oxo-3,4-dihydro-2H-1,4-benzoxazin-6-yl)methyl]amino}-1-piperidinyl)methyl]-4,5-dihydro-7H-pyrrolo[3,2,1-de]-1,5-naphthyridin-7-one Enantiomer 1 Hydrochloride

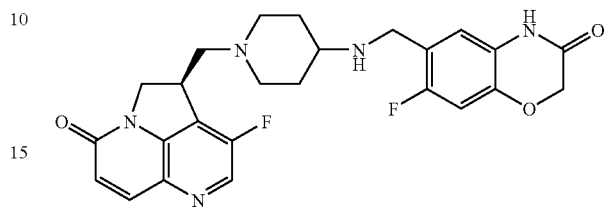

The title compound was prepared from (4R)-4-[(4-amino-1-piperidinyl)methyl]-3-fluoro-4,5-dihydro-7H-pyrrolo[3,2,1-de]-1,5-naphthyridin-7-one Enantiomer 1 and 7-fluoro-3-oxo-3,4-dihydro-2H-benzo[1,4]oxazine-6-carboxaldehyde (for a synthesis, see WO2002056882 Example 8(e)) according to the general method of Example 2(h) in 29% yield.

MS (ES+) m/z 482 (MH+, 30%).

Example 84

(4R)-3-fluoro-4-[(4-{[(7-fluoro-3-oxo-3,4-dihydro-2H-1,4-benzothiazin-6-yl)methyl]amino}-1-piperidinyl)methyl]-4,5-dihydro-7H-pyrrolo[3,2,1-de]-1,5-naphthyridin-7-one Enantiomer 1 Hydrochloride

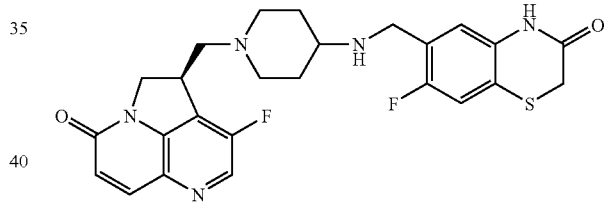

The title compound was prepared from (4R)-4-[(4-amino-1-piperidinyl)methyl]-3-fluoro-4,5-dihydro-7H-pyrrolo[3,2,1-de]-1,5-naphthyridin-7-one Enantiomer 1 and 7-fluoro-3-oxo-3,4-dihydro-2H-benzo[1,4]thiazine-6-carboxaldehyde (for a synthesis, see WO2002056882 Example 22(g)) according to the general method of Example 2(h) in 23% yield.

MS (ES+) m/z 498 (MH+, 50%).

Example 85

(4R)-3-Fluoro-4-[(4-{[(8-fluoro-3-oxo-3,4-dihydro-2H-1,4-benzoxazin-6-yl)methyl]amino}-1-piperidinyl)methyl]-4,5-dihydro-7H-pyrrolo[3,2,1-de]-1,5-naphthyridin-7-one Enantiomer 1 Hydrochloride

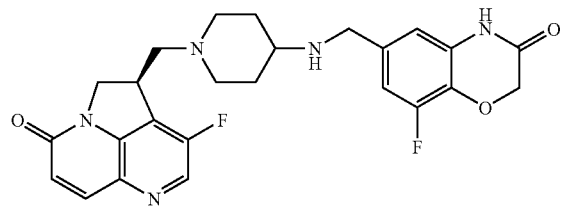

The title compound was prepared from (4R)-4-[(4-amino-1-piperidinyl)methyl]-3-fluoro-4,5-dihydro-7H-pyrrolo[3,2,1-de]-1,5-naphthyridin-7-one Enantiomer 1 and 8-fluoro-3-oxo-3,4-dihydro-2H-1,4-benzoxazine-6-carbaldehyde (for a synthesis, see WO2004052373 Example 45 (intermediate 24)) according to the general method of Example 2(h) in 17% yield.

MS (ES+) m/z 482 (MH+, 35%).

Example 86

(4R)-4-({4-[(2,3-Dihydro[1,4]dioxino[2,3-b]pyridin-7-ylmethyl)amino]-1-piperidinyl}methyl)-3-fluoro-4,5-dihydro-7H-pyrrolo[3,2,1-de]-1,5-naphthyridin-7-one Enantiomer 1 Hydrochloride

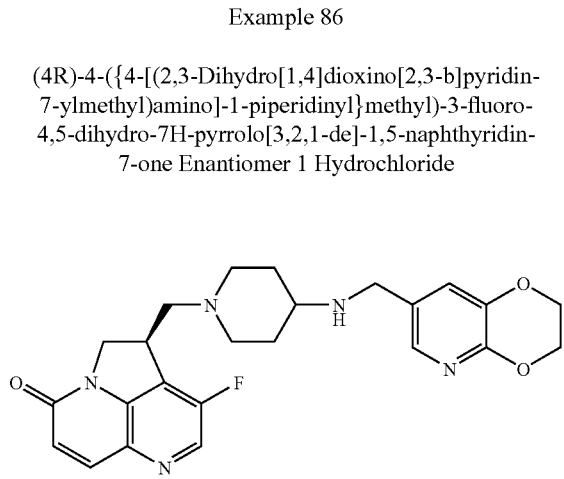

The title compound was prepared from (4R)-4-[(4-amino-1-piperidinyl)methyl]-3-fluoro-4,5-dihydro-7H-pyrrolo[3,2,1-de]-1,5-naphthyridin-7-one Enantiomer 1 and 2,3-dihydro[1,4]dioxino[2,3-b]pyridine-7-carboxaldehyde (for a synthesis, see WO02056882 Example 40(e)) according to the general method of Example 2(h) in 28% yield.

MS (ES+) m/z 452 (MH+, 10%).

Example 87

(4R)-4-({4-[(5,6-Dihydro-4H-cyclopenta[b]thien-2-ylmethyl)amino]-1-piperidinyl}methyl)-3-fluoro-4,5-dihydro-7H-pyrrolo[3,2,1-de]-1,5-naphthyridin-7-one Enantiomer 1 Hydrochloride

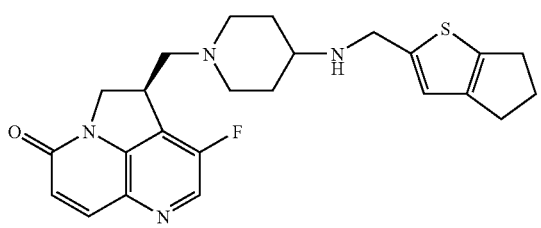

The title compound was prepared from (4R)-4-[(4-amino-1-piperidinyl)methyl]-3-fluoro-4,5-dihydro-7H-pyrrolo[3,2,1-de]-1,5-naphthyridin-7-one Enantiomer 1 and 5,6-dihydro-4H-cyclopenta[b]thiophene-2-carbaldehyde according to the general method of Example 2(h) in 21% yield.

MS (ES+) m/z 437 (MH+, 35%).

Example 88

(4R)-4-({4-[(6,7-Dihydro-5H-thieno[3,2-b]pyran-2-ylmethyl)amino]-1-piperidinyl}methyl)-3-fluoro-4,5-dihydro-7H-pyrrolo[3,2,1-de]-1,5-naphthyridin-7-one Enantiomer 1 Hydrochloride

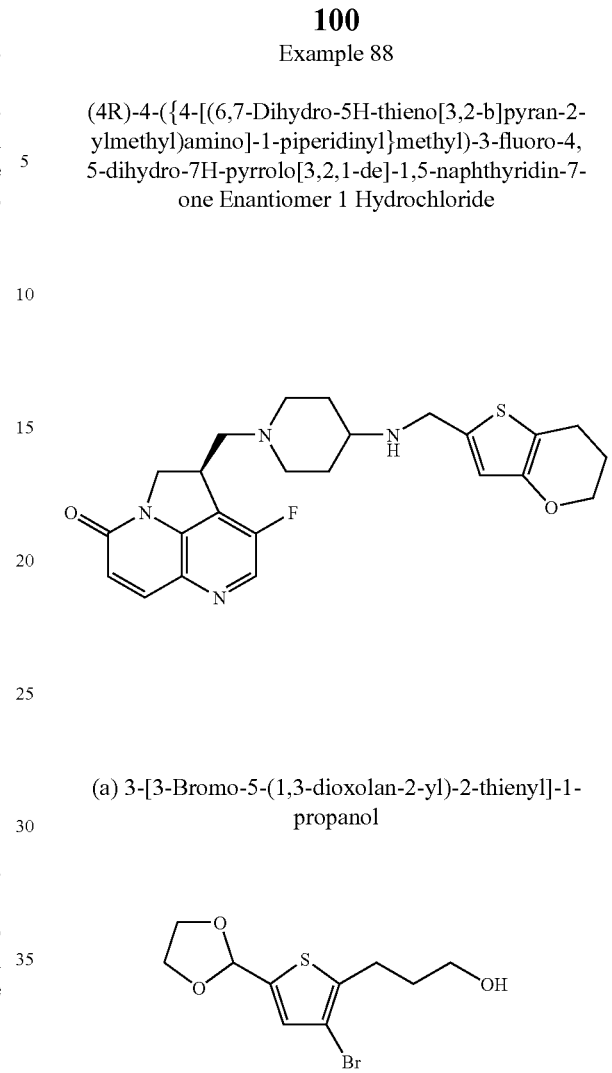

(a) 3-[3-Bromo-5-(1,3-dioxolan-2-yl)-2-thienyl]-1-propanol 2-(4,5-Dibromo-2-thienyl)-1,3-dioxolane (for a synthesis, see J Org Chem, 1976, 41, 8) (6.05 g, 19.2 mmol) was dissolved in dry THF (500 ml) and cooled to −78° C. After 15 min the reaction mixture was treated with 3-(tert-butyldimethylsilyloxy)-1-iodopropane (6.3 g, 1.1 equiv.) (for a synthesis, see J. Chem. Soc. Perkin Trans. 1, 1190, 1111). After a further 15 min. the cooling bath was removed and the reaction allowed warm to room temperature overnight. The reaction was quenched with saturated aqueous ammonium chloride, and partitioned between ethyl acetate and water. The organic phase was dried over anhydrous magnesium sulphate and evaporated. The residue was chromatographed on silica gel eluting with 0-10% ethyl acetate in hexane. Product-containing fractions were combined and evaporated to a colourless oil) 5.61 g. This was dissolved in THF (100 ml) and treated with tetra-n-butyl ammonium fluoride (2M solution in THF, 16 ml) and stirred at room temperature overnight. The solvent was evaporated and the residue partitioned between water and ethyl acetate. The organic phase was separated, washed with brine, dried over anhydrous magnesium sulphate and evaporated. The residue was chromatographed on silica gel eluting with 1-100% ethyl acetate in hexane, to afford the title compound (2.48 g, 44%).

MS (ES+) m/z 295 (MH+, 100%).

(b) 2-(1,3-Dioxolan-2-yl)-6,7-dihydro-5H-thieno[3,2-b]pyran

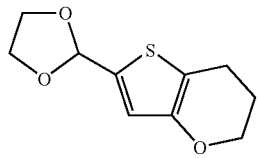

3-[3-Bromo-5-(1,3-dioxolan-2-yl)-2-thienyl]-1-propanol (1.86 g, 6.3 mmol) was dissolved in dry toluene (150 ml), caesium carbonate (3.58 g, 1.5 equiv.) added, and the mixture evacuated and purged with Argon. The evacuation/purge procedure was repeated twice more. In a separate flask, were placed rac-2-di-tert-butylphosphino-1,1'-binaphthyl (Strem chemicals, 257 mg) and palladium(II) acetate (148 mg) in toluene (50 ml). The flask was evacuated and purged with argon and the procedure repeated twice more. After 10 min, the resultant yellow solution of catalyst was added to the flask containing the thiophene via syringe and the flask once more evacuated and purged with argon. The reaction mixture was heated to 100° C. under an argon atmosphere for 3 days. The reaction mixture was cooled, filtered through Kieselguhr and evaporated to low volume. The residue was chromatographed on silica gel eluting with 0-50% ethyl acetate in hexane, to afford the desired compound as a white solid (0.48 g, 36%).

MS (ES+) l/z 213 (MH$^+$, 50%), 169 (100%).

(c) 6,7-Dihydro-5H-thieno[3,2-b]pyran-2-carbaldehyde

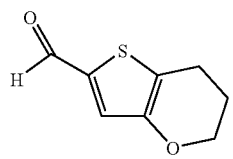

2-(1,3-Dioxolan-2-yl)-6,7-dihydro-5H-thieno[3,2-b]pyran (0.48 g, 2.24 mmol) was dissolved in acetone (25 ml) and water (25 drops) and stirred with polystyrene-sulfonic acid resin (MP-TsOH, Argonaut Technologies inc, 1.35 mmol/g, 200 mg, 0.27 mmol) overnight. The reaction mixture was filtered, the filtrate evaporated and azeotroped with toluene. The title compound was obtained as a pale orange oil (0.44 g).

$^1$H NMR δ (CDCl$_3$) 2.03-2.12 (2H, m), 2.84 (2H, appears as t, J 6.4 Hz), 4.20 (2H, dd, J 5.2, 6.4 Hz), 7.24, (1H, s), 9.75 (1H, s).

(d) Title Compound

The title compound was prepared from (4R)-4-[(4-amino-1-piperidinyl)methyl]-3-fluoro-4,5-dihydro-7H-pyrrolo[3,2,1-de]-1,5-naphthyridin-7-one Enantiomer 1 and 6,7-dihydro-5H-thieno[3,2-b]pyran-2-carbaldehyde according to the general method of Example 2(h) in 14% yield.

MS (ES+) m/z 453 (MH$^+$, 100%).

Example 89

(4R)-4-({4-[(2,3-Dihydro-1,4-benzodioxin-6-ylmethyl)amino]-1-piperidinyl}methyl)-3-fluoro-4,5-dihydro-7H-pyrrolo[3,2,1-de]-1,5-naphthyridin-7-one Dihydrochloride

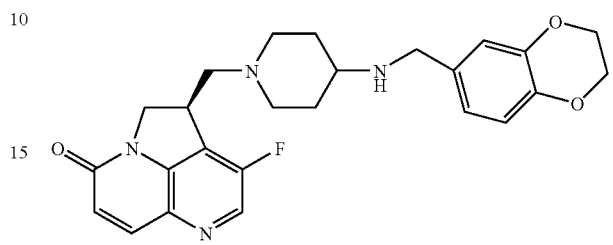

The title compound was prepared from (4R)-4-[(4-amino-1-piperidinyl)methyl]-3-fluoro-4,5-dihydro-7H-pyrrolo[3,2,1-de]-1,5-naphthyridin-7-one Enantiomer 1 and 2,3-dihydro-1,4-benzodioxin-6-carboxaldehyde (Aldrich) according to the general method of Example 2(h) (except that the dihydrochloride was prepared) in 71% yield.

MS (ES+) m/z 451 (MH$^+$, 100%).

Example 90

(4R)-3-Fluoro-4-({4-[([1,2,3]thiadiazolo[5,4-b]pyridin-6-ylmethyl)amino]-1-piperidinyl}methyl)-4,5-dihydro-7H-pyrrolo[3,2,1-de]-1,5-naphthyridin-7-one Dihydrochloride

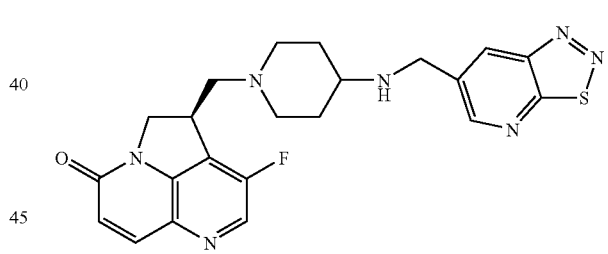

To a solution of [1,2,3]thiadiazolo[5,4-b]pyridin-6-ylmethanol (for a synthesis see WO2003064431, Example 1(b (iv)) (28 mg, 0.166 mmol) in THF (1 ml) was added triethylamine (0.023 ml, 0.166 mmol) and then methanesulfonyl chloride (0.013 ml, 0.166 mmol) and the reaction was then stirred at room temperature for 2 h. DMF (1 ml) was then added followed by (4R)-4-[(4-amino-1-piperidinyl)methyl]-3-fluoro-4,5-dihydro-7H-pyrrolo[3,2,1-de]-1,5-naphthyridin-7-one Enantiomer 1 (50 mg, 0.166 mmol) and potassium carbonate (0.166 mmol) and the reaction was stirred at room temperature for a further 72 h before evaporation. The residue was subjected to column chromatography on silica gel using a dichloromethane, methanol gradient to provide the free base of the title compound (20 mg, 27%).

MS (ES+) m/z 452 (MH$^+$, 100%).

The free base of the title compound was converted to the dihydrochloride by dissolving in chloroform-methanol, adding excess 4M HCl in 1,4-dioxane and then evaporating to dryness. MS as that of free base.

Biological Activity

Antimicrobial Activity Assay:

Whole-cell antimicrobial activity was determined by broth microdilution using the Clinical and Laboratory Standards Institute (CLSI) recommended procedure, Document M7-A7, "Methods for Dilution Susceptibility Tests for Bacteria that Grow Aerobically". The compounds were tested in serial two-fold dilutions ranging from 0.016 to 16 mcg/mL.

Compounds were evaluated against a panel of Gram-positive organisms, including *Staphylococcus aureus, Streptococcus pneumoniae, Streptococcus pyogenes, Enterococcus faecalis* and *Enterococcus faecium*.

In addition, compounds were evaluated against a panel of Gram-negative organisms including *Haemophilus influenzae, Moraxella catarrhalis, Escherichia coli, Pseudomonas aeruginosa, Proteus mirabilis, Legionellapneumophila, Chlamydia pneumoniae, Enterobacter cloacae, Enterobacter aerogenes, Klebsiella pneumoniae* and *Stenotrophomonas maltophilia*.

The *L. pneumophila* isolates were tested using a modified CLSI procedure for broth microdilution. For this assay, compounds were tested in serial doubling dilutions over a concentration range of 0.03 to 32 mcg/mL. An inoculum of each test isolate was prepared in buffered yeast broth and adjusted to a density equivalent to a 0.5 McFarland standard. After inoculation, the microtitre plates were incubated at 37° C. for 72 hours.

For the *C. pneumoniae* isolates, stocks were thawed and diluted in CCM to yield an inoculum containing ~1×10$^4$ inclusion forming units/ml (IFUs/ml). A 100 µL aliquot of the inoculum was added to all wells of a microtitre plate containing HEp-2 cells grown to confluence. Microtitre plates were centrifuged for 1 hour at 1700 g., then incubated for 1 hour at 35° C. in 5% $CO_2$. One hundred microliters of diluted test compounds, prepared as a 2-fold dilution series in CCM/cycloheximide was then added to the microtiter plates. After 72 hours incubation at 35° C. in 5% $CO_2$, the microtitre plates were stained with a murine monoclonal fluorescein-conjugated antibody (Kallestad Cat. #532 Roche Biomedical Products) in accordance with the manufacturer recommendations. Upon staining, the IFUs produced an apple-green color, visible against the red counter stained HEp-2 cells when viewed at 100× magnification. The MIC was defined as the lowest concentration of compound at which no IFUs were seen.

The minimum inhibitory concentration (MIC) was determined as the lowest concentration of compound that inhibited visible growth. A mirror reader was used to assist in determining the MIC endpoint.

Each of the listed Examples as identified in the present application, were tested in at least one exemplified salt form except Example 49 which was tested as the free base, and had a MIC ≦2 µg/ml against a strain of at least one of the organisms listed above. For at least one strain of every organism listed above, at least one Example had a MIC ≦2 µg/ml with the exception of strains of *Pseudomonas aeruginosa*, for which at least some Examples had a MIC ≦4 µg/ml.

The invention claimed is:

1. A compound of formula (I) or a pharmaceutically acceptable salt; N-oxide thereof:

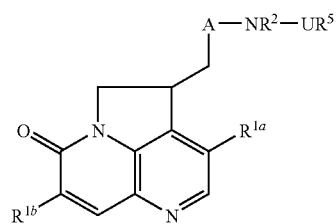

(I)

wherein:

$R^{1a}$ and $R^{1b}$ are independently selected from hydrogen; halogen; cyano; $(C_{1-6})$alkyl; $(C_{1-6})$alkylthio; trifluoromethyl; trifluoromethoxy; carboxy; hydroxy optionally substituted with $(C_{1-6})$alkyl or $(C_{1-6})$alkoxy-substituted $(C_{1-6})$alkyl; $(C_{1-6})$alkoxy-substituted$(C_{1-6})$alkyl; hydroxy $(C_{1-6})$alkyl; an amino group optionally N-substituted by one or two $(C_{1-6})$alkyl, formyl, $(C_{1-6})$alkylcarbonyl or $(C_{1-6})$alkylsulphonyl groups; and aminocarbonyl wherein the amino group is optionally substituted by $(C_{1-4})$alkyl;

$R^2$ is hydrogen, or $(C_{1-4})$alkyl, or together with $R^6$ forms Y as defined below;

A is a group (i):

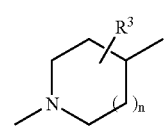

(ia)

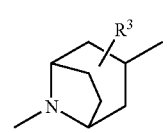

(ib)

in which:

$R^3$ is as defined for $R^{1a}$ or $R^{1b}$ or is oxo and n is 1 or 2;

or A is a group (ii):

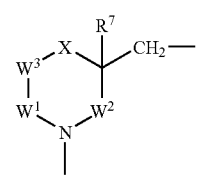

(ii)

in which:

$W^1$, $W^2$ and $W^3$ are $CR^4R^8$;

or $W^2$ and $W^3$ are $CR^4R^8$ and $W^1$ represents a bond between $W^3$ and N;

X is O, $CR^4R^8$, or $NR^6$;

one $R^4$ is as defined for $R^{1a}$ and $R^{1b}$ and the remainder and $R^8$ are hydrogen, or one $R^4$ and $R^8$ are together oxo and the remainder are hydrogen;

$R^6$ is hydrogen or $(C_{1-6})$alkyl; or together with $R^2$ forms Y;

$R^7$ is hydrogen; halogen; hydroxy optionally substituted with $(C_{1-6})$alkyl; or $(C_{1-6})$alkyl;

Y is $CR^4R^8CH_2$; $CH_2CR^4R^8$; (C=O); $CR^4R^8$; $CR^4R^8$(C=O); or (C=O)$CR^4R^8$;
or when X is $CR^4R^8$, $R^8$ and $R^7$ together represent a bond;
U is selected from CO and $CH_2$ and
$R^5$ is an optionally substituted bicyclic carbocyclic or heterocyclic ring system (B):

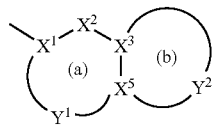

(B)

containing up to four heteroatoms in each ring in which:
at least one of rings (a) and (b) is aromatic;
$X^1$ is C or N when part of an aromatic ring, or $CR^{14}$ when part of a non-aromatic ring;
$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;
$X^3$ and $X^5$ are independently N or C;
$Y^1$ is a 0 to 4 atom linker group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring;
$Y^2$ is a 2 to 6 atom linker group, each atom of $Y^2$ being independently selected from N, $NR^{13}$, O, $S(O)_x$, CO, and $CR^{14}$ when part of an aromatic or non-aromatic ring or may additionally be $CR^{14}R^{15}$ when part of a non aromatic ring;
each of $R^{14}$ and $R^{15}$ is independently selected from: H; $(C_{1-4})$alkylthio; halo; carboxy$(C_{1-4})$alkyl; $(C_{1-4})$alkyl; $(C_{1-4})$alkoxycarbonyl; $(C_{1-4})$alkylcarbonyl; $(C_{1-4})$alkoxy$(C_{1-4})$alkyl; hydroxy; hydroxy$(C_{1-4})$alkyl; $(C_{1-4})$alkoxy; nitro; cyano; carboxy; amino and aminocarbonyl, wherein the amino or aminocarbonyl are optionally mono- or di-substituted by $(C_{1-4})$alkyl; or
$R^{14}$ and $R^{15}$ may together represent oxo;
each $R^{13}$ is independently H; trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; $(C_{1-4})$alkoxycarbonyl; $(C_{1-4})$alkylcarbonyl; $(C_{1-6})$alkylsulphonyl; or aminocarbonyl wherein the amino group is optionally mono or disubstituted by $(C_{1-4})$alkyl; and
each x is independently 0, 1 or 2.

2. A compound of formula (I) according to claim 1 or a pharmaceutically acceptable salt thereof or N-oxide thereof wherein $R^{1a}$ is hydrogen, chloro or fluoro and $R^{1b}$ is hydrogen.

3. A compound of formula (I) according to claim 1 or a pharmaceutically acceptable salt thereof or N-oxide thereof wherein $R^2$ is hydrogen.

4. A compound of formula (I) according to claim 1 or a pharmaceutically acceptable salt thereof or N-oxide thereof wherein A is a group (ia) in which n is 1 and $R^3$ is hydrogen or hydroxy.

5. A compound of formula (I) according to claim 1 or a pharmaceutically acceptable salt thereof or N-oxide thereof wherein U is $CH_2$.

6. A compound of formula (I) according to claim 1 or a pharmaceutically acceptable salt thereof or N-oxide thereof wherein $R^5$ is an aromatic heterocyclic ring (B) having 8-11 ring atoms, 2-4 of which ring atoms are heteroatoms, at least one of which is N or $NR^{13}$; wherein $Y^2$ contains 2-3 heteroatoms, one of which is S and 1-2 of which are N, with one N bonded to $X^3$, or the heterocyclic ring (B) has ring (a) aromatic selected from optionally substituted benzo and pyrido and pyridazino and ring (b) non aromatic and $Y^2$ has 3-5-atoms at least one of which is a heteroatom, with O, S, $CH_2$ or $NR^{13}$ bonded to $X^5$ where $R^{13}$ is other than hydrogen, and either NHCO bonded via N to $X^3$, or O, S, $CH_2$ or NH bonded to $X^3$.

7. A compound of formula (I) according to claim 1 or a pharmaceutically acceptable salt thereof or N-oxide thereof wherein $R^5$ is selected from the group consisting of:
3-oxo-3,4-dihydro-2H-pyrido[3,2-b][1,4]oxazin-6-yl;
3-oxo-3,4-dihydro-2H-pyrido[3,2-b][1,4]thiazin-6-yl;
2,3-dihydro-[1,4]dioxino[2,3-c]pyridin-7-yl;
[1,3]oxathiolo[5,4-c]pyridin-6-yl;
3,4-dihydro-2H-pyrano[2,3-c]pyridine-6-yl;
[1,2,3]thiadiazolo[5,4-b]pyridin-6-yl;
2,3-dihydro-1,4-benzodioxin-5-carbonitro-7-yl;
8-fluoro-2,3-dihydro-1,4-benzodioxin-6-yl;
3-oxo-3,4-dihydro-2H-benzo[1,4]thiazin-6-yl; and
2,3-dihydro[1,4]oxathiino[2,3-c]pyridin-7-yl.

8. A compound selected from the group consisting of:
4-[(4-{[(3-oxo-3,4-dihydro-2H-pyrido[3,2-b][1,4]thiazin-6-yl)methyl]amino]-1-piperidinyl)methyl]-4,5-dihydro-7H-pyrrolo[3,2,1-de]-1,5-naphthyridin-7-one;
3-chloro-4-({4-[(2,3-dihydro[1,4]dioxino[2,3-c]pyridin-7-ylmethyl)amino]-1-piperidinyl}methyl)-4,5-dihydro-7H-pyrrolo[3,2,1-de]-1,5-naphthyridin-7-one;
3-chloro-4-[(4-{[(3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one or an enantiomer thereof;
3-chloro-4-[(4-{[(3-oxo-3,4-dihydro-2H-pyrido[3,2-b][1,4]oxazin-6-yl)methyl]amino-1-piperidinyl)methyl]-4,5-dihydro-7H-pyrrolo[3,2,1-de]-1,5-naphthyridin-7-one;
3-chloro-4-[(4-{[(7-chloro-3-oxo-3,4-dihydro-2,1-pyrido[3,2-b][1,4]oxazin-6-yl)methyl]amino}-1-piperidinyl)methyl]-4,5-dihydro-7H-pyrrolo[3,2,1-de]-1,5-naphthyridin-7-one;
3-chloro-4-[(4-{[(8-fluoro-2,3-dihydro-1,4-benzodioxin-6-yl)methyl]amino}-1-piperidinyl)methyl]-4,5-dihydro-7H-pyrrolo[3,2,1-de]-1,5-naphthyridin-7-one;
N-{1-[(3-chloro-7-oxo-4,5-dihydro-7H-pyrrolo[3,2,1-de]-1,5-naphthyridin-4-yl)methyl]-4-piperidinyl)-3-oxo-3,4-dihydro-2H-pyrido[(3,2-b][1,4]thiazine-6-carboxamide;
4-({4-[(2,3-dihydro[1,4]dioxino[2,3-c]pyridin-7-ylmethyl)amino]-1-piperidinyl}methyl)-3-fluoro-4,5-dihydro-7H-pyrrolo[3,2,1-de]-1,5-naphthyridin-7-one;
3-fluoro-4-[(4-{[(3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one;
N-{1-[(3-fluoro-7-oxo-4,5-dihydro-7H-pyrrolo[3,2,1-de]-1,5-naphthyridin-4-yl)methyl]-4-piperidinyl}-3-oxo-3,4-dihydro-2H-pyrido[3,2-b]4]oxazine-6-carboxamide; 3-chloro-4-[((3R,4S)-4-{[(7-fluoro-2,3-dihydro-1,4-benzodioxin-6-yl)methyl]amino}-3-hydroxy-1-piperidinyl)methyl)-4,5-dihydro-7H-1-pyrrolo[3,2,1-de]-1,5-naphthyridin-7-one or a diastereomer thereof;

4-({(3R,4S)-4-((2,3-dihydro[1,4]dioxino[2,3-c]pyridin-7-ylmethyl)amino)-3-hydroxy-1-piperidinyl}methyl)-3-fluoro-4,5-dihydro-7H-pyrrolo[3,2,1-de]-1,5-naphthyridin-7-one;

4-({(3R,4S)-4-[(2,3-dihydro-1-benzofuran-5-ylmethyl)amino]-3-hydroxy-1-piperidinyl}methyl)-3-fluoro-4,5-dihydro-7H-pyrrolo[3,2,1-de]-1,5-naphthyridin-7-one;

4-({(3R,4S)-4-[(2,3-dihydro-1,4-benzodioxin-6-ylmethyl)amino]-3-hydroxy-1-piperidinyl}methyl)-3-fluoro-4,5-dihydro-7H-pyrrolo[3,2,1-de]-1,5-naphthyridin-7-one;

3-chloro-4-[((3R,4S)-4-{[(7-fluoro-3-oxo-3,4-dihydro-2H-1,4-benzothiazin-6-yl)methyl]amino}-3-hydroxy-1-piperidinyl)methyl]-4,5-dihydro-7H-pyrrolo[3,2,1-de]-1,5-naphthyridin-7-one or a diastereomer thereof;

3-chloro-4-[((3R,4S)-3-hydroxy-4-{[(3-oxo-3,4-dihydro-2H-pyrido-3,2-b][1,4]thiazin-6-yl)methyl]amino}-1-piperidinyl)methyl]-4,5-dihydro-7H-pyrrolo[3,2,1-de]-1,5-naphthyridin-7-one;

N-{(3R,4S)-1-[(3-chloro-7-oxo-4,5-dihydro-7H-pyrrolo[3,2,1-de]-1,5-naphthyridin-4-yl)methyl]-3-hydroxy-4-piperidinyl}-3-oxo-3,4-dihydro-2H-pyrido[3,2-b][1,4]thiazine-6-carboxamide;

3-chloro-4-({(3R,4S)-4-[(2,3-dihydro[1,4]dioxino[2,3-c]pyridin-7-ylmethyl)amino]-3-hydroxy-1-piperidinyl}methyl)-4,5-dihydro-7H-pyrrolo[3,2,1-de]-1,5-naphthyridin-7-one;

3-chloro-4-[(4-{[(3-oxo-3,4-dihydro-2H-1,4-benzoxazin-6-yl)methyl]amino}-1-piperidinyl)methyl]-4,5-dihydro-7H-pyrrolo[3,2,1-de]-1,5-naphthyridin-7-one;

3-chloro-4-({4-[(2,3-dihydro[1,4]dioxino[2,3-c]pyridin-7-ylmethyl)amino]-1-piperidinyl}methyl)-4,5-dihydro-7H-pyrrolo[3,2,1-de]-1,5-naphthyridin-7-one or an enantiomer thereof;

3-chloro-4-[(4-{[(3-oxo-3,4-dihydro-2H-1,4-benzothiazin-6-yl)methyl]amino}-1-piperidinyl)methyl]-4,5-dihydro-7H-pyrrolo[3,2,1-de]-1,5-naphthyridin-7-one or an enantiomer thereof; 3-chloro-4-[(4-{[(2-oxo-2,3-dihydro-1H-pyrido[2,3-b][1,4]thiazin-7-yl)methyl]amino}-1-piperidinyl)methyl]-4,5-dihydro-7H-pyrrolo[3,2,1-de]-1,5-naphthyridin-7-one or an enantiomer thereof;

3-chloro-4-({(3R,4S)-3-hydroxy-4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one or a diastereomer thereof;

3-chloro-4 ({(3R,4S)-4-[(3,4-dihydro-2H-pyrano[2,3-c]pyridin-6-ylmethyl)amino]-3-hydroxy-1-piperidinyl}methyl)-4,5-dihydro-7H-pyrrolo[3,2,1-de]-1,5-naphthyridin-7-one;

3-chloro-4-({4-[(2,3-dihydro[1,4]oxathiino[2,3-c]pyridin-7-ylmethyl)amino]-1-piperidinyl}methyl)-4,5-dihydro-7H-pyrrolo[3,2,1-de]-1,5-naphthyridin-7-one or an enantiomer thereof;

3-chloro-4-({4-[(2,3-dihydrofuro[2,3-c]pyridin-5-ylmethyl)amino]-1-piperidinyl}methyl)4,5-dihydro-7H-pyrrolo[3,2,1-de]-1,5-naphthyridin-7-one;

(4R)-4-({4-[(2,3-dihydro[1,4]dioxino[2,3-c]pyridin-7-ylmethyl)amino]-1-piperidinyl}methyl)-3-fluoro-4,5-dihydro-7H-pyrrolo[3,2,1-de]-1,5-naphthyridin-7-one;

(4R)-4-({4-[(3,4-Dihydro-2H-pyrano[2,3-c]pyridin-6-ylmethyl)amino]-1-piperidinyl}methyl)-3-fluoro-4,5-dihydro-7H-pyrrolo[3,2,1-de]-1,5-naphthyridin-7-one;

(4R)-3-fluoro-4-({4-[([1,3]oxathiolo[5,4-c]pyridin-6-ylmethyl)amino]-1-piperidinyl methyl)-4,5-dihydro-7H-pyrrolo[3,2,1-de]-1,5-naphthyridin-7-one;

(4R)-3-fluoro-4-[(4-{[(3-oxo-3,4-dihydro-2H-pyrido[3,2-b][1,4]oxazin-6-yl)methyl]amino}-1-piperidinyl)methyl]-4,5-dihydro-7H-pyrrolo[3,2,1-de]-1,5-naphthyridin-7-one;

(4R)-3-fluoro-4-[(4-{[(3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one;

(4S)-4-({4-[2,3-dihydro[1,4]-dioxino[2,3-c]pyridin-7-ylmethyl)amino]-1-piperidinyl}methyl)-3-fluoro-4,5-dihydro-7H-pyrrolo[3,2,1-de]-[1,5-naphthyridin-7-one;

(4R)-4-({4-[(2,3-dihydro[1,4]oxathiino[2,3-c]pyridin-7-ylmethyl)amino]-1-piperidinyl}methyl)-3-fluoro-4,5-dihydro-7H-pyrrolo[3,2,1-de]-1,5-naphthyridin-7-one;

(4R)-4-({4-[(2,3-dihydrofuro[2,3c]-pyridin-5-ylmethyl)amino]-1-piperidinyl}methyl)-3-fluoro-4,5-dihydro-7H-pyrrolo[3,2,1-de]-1,5-naphthyridin-7-one; 4-({cis-4-[(2,3-dihydro[1,4]dioxino[2,3c]pyridin-7-ylmethyl)amino]-3-fluoro-1-piperidinyl}methyl)-3-fluoro-4,5-dihydro-7H-pyrrolo[3,2,1-de][1,5-naphthyridin-7-one;

3-fluoro-4-[(cis-3-fluoro-4-{[(3-oxo-3,4-dihydro-2H-pyrido[3,2-b][1,4]oxazin-6-yl)methyl]amino}-1-piperidinyl)methyl]-4,5-dihydro-7H-pyrrolo[3,2,1-de]-1,5-naphthyridin-7-one;

3-fluoro-4-[(cis-3-fluoro-4-{[3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one;

4-[{(cis-4-[(2,3-dihydro[1,4-benzodioxin-6-ylmethyl)amino]-3-fluoro-1-piperidinyl}methyl)-3-fluoro-4,5-dihydro-7H-pyrrolo[3,2,1-de]-1,5-naphthyridin-7-one;

3-fluoro-4-{cis-4-hydroxy-3-({[(3-oxo-3,4-dihydro-2H-pyrido-[3,2-b][1,4]thiazin-6-yl)methyl]amino}methyl)-1-piperidinyl]methyl}-4,5-dihydro-7H-pyrrolo[3,2,1-de]-1,5-naphthyridin-7-one;

4-[(cis-3-{[2,3-dihydro1,4]dioxino[2,3-c]pyridin-7-ylmethyl)amino]methyl}4-hydroxy-1-piperidinyl)methyl]-3-fluoro-4,5-dihydro-7H-pyrrolo[3,2,1-de]-1,5-naphthyridin-7-one;

4-[((2S)-2-{[(2,3-dihydro[1,4]dioxino[2,3-c]pyridin-7-ylmethyl)amino]methyl-4-morpholinyl)methyl]-3-fluoro-4,5-dihydro-7H-pyrrolo[3,2,1-de]-1,5-naphthyridin-7-one;

3-fluoro-4-[((2S)-2-{[([1,3]oxathiolo[5,4-c]pyridin-6-ylmethyl)amino]methyl}-4-morpholinyl)methyl]-4,5-dihydro-7H-pyrrolo[3,2,1-de]-1,5-naphthyridin-7-one;

3-fluoro-4-{[(2S)-2-({[(3-oxo-3,4-dihydro-2H-pyrido[32-b][1,4]thiazin-6-yl)methyl]amino}methyl)-4-morpholinyl]methyl-4,5-dihydro-7H-pyrrolo[3,2,1-de]-1,5-naphthyridin-7-one;

3-chloro-4-({4-[([1,3]oxathiolo[5,4-c]pyridin-6-ylmethyl)amino]-1-piperidinyl]methyl)-4,5-dihydro-7H-pyrrolo[3,2,1-de]-1,5-naphthyridin-7-one or an enantiomer thereof;

3-chloro-4-({4-[(3,4-dihydro-2H-pyrano[2,3-c]pyridin-6-ylmethyl)amino]-1-piperidinyl}methyl)-4,5-dihydro-7H-pyrrolo[3,2,1-de]-1,5-naphthyridin-7-one or an enantiomer thereof;

3-chloro-4-[(4-{[(3-oxo-3,4-dihydro-2H-pyrido[3,2-b][1,4]oxazin-6-yl)methyl]amino}-1-piperidinyl)methyl]-4,5-dihydro-7H-pyrrolo[3,2,1-de]-1,5-naphthyridin-1-7-one; or an enantiomer thereof;

3-chloro-4-({(3R,4S)-3-hydroxy-4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one or a diastereomer thereof;

3-fluoro-4-((3R,4S)-3-hydroxy-4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one or a diastereomer thereof;

7-[({3R,4S)-1-[(3-chloro-7-oxo-4,5-dihydro-7H-pyrrolo[3,2,1-de]-1,5-naphthyridin-4-yl)methyl]-3-hydroxy-4-piperidinyl}amino)methyl]-2,3-dihydro-1,4-benzodioxin-5-carbonitrile or a diastereomer thereof;

4-({4-[(2,3-dihydro[1,4]dioxino[2,3-c]pyridin-7-ylmethyl)amino]-1-piperidinyl}methyl)-4,5-dihydro-7H-pyrrolo[3,2,1-de]-1,5-naphthyridin-7-one;

4-({4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one;

7-{[(1-{[(4R)-3-fluoro-7-oxo-4,5-dihydro-7H-pyrrolo[3,2,1-de)-1,5-naphthyridin-4-yl]methyl}-4-piperidinyl)amino]methyl}-2,3-dihydro-1,4-benzodioxin-5-carbonitrile;

(4R)-3-fluoro-4-[(4-{[(2-oxo-2,3-dihydro-1H-pyrido[2,3-b][1,4]thiazin-7-yl)methyl]amino}-1-piperidinyl)methyl]-4,5-dihydro-7H-pyrrolo[3,2,1-de]-1,5-naphthyridin-7-one;

3-chloro-4-{(4-{[(5-oxo-1,2,3,5-tetrahydro-7-indolizinyl)methyl]amino}-1-piperidinyl)methyl-4,5-dihydro-7H-pyrrolo[3,2,1-de]-1,5-naphthyridin-7-one;

3-chloro-4-[(4-{((2-methyl-1-oxo-1,2,3,4-tetrahydro-7-isoquinolinyl)methyl]amino}-1-piperidinyl)methyl]-4,5-dihydro-7H-pyrrolo[3,2,1-de]-1,5-naphthyridin-7-one;

(4R)-3-fluoro-4-[(4-{((3-oxo-3,4-dihydro-2H-1,4-benzoxazin-6-yl)methyl]amino}-1-piperidinyl)methyl]-4,5-dihydro-7H-pyrrolo[3,2,1-de]-1,5-naphthyridin-7-one; (4R)-4-[(4-{[(7-chloro-3-oxo-3,4-dihydro-2H-pyrido[3,2-b][1,4]oxazin-6-yl)methyl]amino}-1-piperidinyl)methyl]-3-fluoro-4,5-dihydro-7H-pyrrolo[3,2,1-de]-1,5-naphthyridin-7-one;

(4R)-3-fluoro-4-[(4-{[(8-fluoro-2,3-dihydro-1,4-benzodioxin-6-yl)methyl]amino}-1-piperidinyl)methyl]-4,5-dihydro-7H-pyrrolo[3,2,1-de]-1,5-naphthyridin-7-one;

(4R)-4-[(4-{[(7-bromo-3-oxo-3,4-dihydro-2H-pyrido[3,2-b][1,4]thiazin-6-yl)methyl]amino}-1-piperidinyl)methyl]-3-fluoro-4,5-dihydro-7H-pyrrolo[3,2,1-de]-1,5-naphthyridin-7-one; 4-({3S,4R)-4-[([1,3]oxathiolo[5,4-c]pyridin-6-ylmethyl)amino]-3-hydroxy-1-piperidinyl}methyl)-3-fluoro-4,5-dihydro-7H-pyrrolo[3,2,1-de]-1,5-naphthyridin-7-one or a diastereomer thereof;

4-({(3R,4S)-4-[([1,3]oxathiolo[5,4-c]pyridin-6-ylmethyl)amino]-3-hydroxy-1-piperidinyl}methyl)-3-fluoro-4,5-dihydro-7H-pyrrolo[3,2,1-de]-1,5-naphthyridin-7-one or a diastereomer thereof; 4-({(3R,4S)-4-[2,3-dihydro[1,4]dioxino[2,3-c]pyridin-7-ylmethyl)amino]-3-hydroxy-1-piperidinyl}methyl)-3-fluoro-4,5-dihydro-7H-pyrrolo[3,2,1-de]-1,5-naphthyridin-7-one or a diastereomer thereof;

4-(3R,4S)-4-[(2,3-dihydro[1,4]oxathiino[2,3-c]pyridin-7-ylmethyl)amino]-3-hydroxy-1-piperidinyl}methyl)-3-fluoro-4,5-dihydro-7H-pyrrolo[3,2,1-de]-1,5-naphthyridin-7-one or a diastereomer thereof; 3-fluoro-4-({(3R,4S)-4-[(3,4-dihydro-2H-pyrano[2,3-c]pyridin-6-ylmethyl)amino]-3-hydroxy-1-piperidinyl}methyl)-4,5-dihydro-7H-pyrrolo[3,2,1-de]-1,5-naphthyridin-7-one; (4R)-3-fluoro-4-[(4-{[(3-oxo-3,4-dihydro-2H-1,4-benzothiazin-6-yl)methyl]amino}-1-piperidinyl)methyl]-4,5-dihydro-7H-pyrrolo[3,2,1-de]-1,5-naphthyridin-7-one;

5-{[(1-{[(4R)-3-fluoro-7-oxo-4,5-dihydro-7H-pyrrolo[3,2,1-de]-1,5-naphthyridin-4-yl]methyl}-4-piperidinyl)amino]methyl}-2,3-dihydro-1-benzofuran-7-carbonitrile;

4-{[(3R,4S)-4-[(2,3-dihydro[1,4]dioxino[2,3-c]pyridin-7-ylmethyl)amino]-3-(methyloxy)-1-piperidinyl]methyl}-3-fluoro-4,5-dihydro-7H-pyrrolo[3,2,1-de]-1,5-naphthyridin-7-one; 4-{[(3R,4S)-4-[(3,4-dihydro-2H-pyrano[2,3-c]pyridin-6-ylmethyl)amino]-3-(methyloxy)-1-piperidinyl]methyl}-3-fluoro-4,5-dihydro-7H-pyrrolo[3,2,1-de]-1,5-naphthyridin-7-one;

3-fluoro-4-((3R,4S)-3-(methyloxy)-4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one;

5-({[(3R,4S)-1-[(3-fluoro-7-oxo-4,5-dihydro-7H-pyrrolo[3,2,1-de]-1,5-naphthyridin-4-yl)methyl]-3-(methyloxy)-4-piperidinyl]amino}methyl)-2,3-dihydro-1-benzofuran-7-carbonitrile;

4-[((3R,4S)-4-{[(7-bromo-2,3-dihydro-1,4-benzodioxin-6-yl)methyl]amino}-3-hydroxy-1-piperidinyl)methyl]-3-fluoro-4,5-dihydro-7H-pyrrolo[3,2,1-de]-1,5-naphthyridin-7-one or a diastereomer thereof; 4-({(3R,4S)-4-[(5,6-dihydro-4H-cyclopenta[b]thien-2-ylmethyl)amino]-3-hydroxy-1-piperidinyl}methyl)-3-fluoro-4,5-dihydro-7H-pyrrolo[3,2,1-de]-1,5-naphthyridin-7-one or a diastereomer thereof;

(4R)-3-fluoro-4-[(4-{[(7-fluoro-3-oxo-3,4-dihydro-2H-1,4-benzoxazin-6-yl)methyl]amino}-1-piperidinyl)methyl]-4,5-dihydro-7H-pyrrolo[3,2,1-de]-1,5-naphthyridin-7-one;

(4R)-3-fluoro-4-[(4-{[(7-fluoro-3-oxo-3,4-dihydro-2H-1,4-benzothiazin-6-yl)methyl]amino}-1-piperidinyl)methyl]-4,5-dihydro-7H-pyrrolo[3,2,1-de]-1,5-naphthyridin-7-one; (4R)-3-fluoro-4-{[(4-{[(8-fluoro-3-oxo-3,4-dihydro-2H-1,4-benzoxazin-6-yl)methyl]amino}-1-piperidinyl)methyl]-4,5-dihydro-7H-pyrrolo[3,2,1-de]-1,5-naphthyridin-7one;

(4R)-4-({4-[(2,3-dihydro(1,4]dioxino[2,3-b]pyridin-7-ylmethyl)amino]-1-piperidinyl}methyl)-3-fluoro-4,5-dihydro-7H-pyrrolo[3,2,1-de]-1,5-naphthyridin-7-one;

(4R)-4-({4-[(5,6-dihydro-4H-cyclopenta[b]thien-2-ylmethyl)amino]-1-piperidinyl}methyl)-3-fluoro-4,5-dihydro-7H-pyrrolo[3,2,1-de]-1,5-naphthyridin-7-one;

(4R)-4-({4-[(6,7-dihydro-5H-thieno[3,2-b]pyran-2-ylmethyl)amino]-1-piperidinyl}methyl)-3-fluoro-4,5-dihydro-7H-pyrrolo[3,2,1-de]-1,5-naphthyridin-7-one;

(4R)-4-({4-[(2,3-dihydro-1,4-benzodioxin-6-ylmethyl)amino]-1-piperidinyl}methyl)-3-fluoro-4,5-dihydro-7H-pyrrolo[3,2,1-de]-1,5-naphthyridin-7-one; and (4R)-3-fluoro-4-({4-[([1,2,3]thiadiazolo[5,4-b]pyridin-6-ylmethyl)amino]-1-piperidinyl}methyl)-4,5-dihydro-7H-pyrrolo[3,2,1-de]-1,5-naphthyridin-7-one;

or a pharmaceutically acceptable salt thereof.

9. A method of treatment of a bacterial infection which method comprises administering to a mammal in need of such treatment an effective amount of a compound of formula (I) according to claim 1 or a pharmaceutically acceptable salt thereof or an N-oxide thereof, wherein the bacterial infection is selected from the group consisting of *Staphylococcus aureus, Streptococcus pneumoniae, Streptococcus pyogenes, Enterococcus faecalis, Enterococcus faecium, Haemophilus influenzae, Moraxella catarrhalis, Escherichia coli, Pseudomonas aeruginosa, Proteus mirabilis, Legionella pneumophila, Chlamydia pneumoniae, Enterobacter cloacae, Enterobacter aerogenes, Klebsiella pneumoniae* and *Stenotrophomonas maltophilia*.

10. A pharmaceutical composition comprising a compound of formula (I) according to claim 1 or a pharmaceutically acceptable salt thereof of N-oxide thereof; and a pharmaceutically acceptable carrier.

11. A method according to claim 9 wherein the mammal is a human.

12. A compound of formula (I) according to claim 1 or a pharmaceutically acceptable salt thereof or N-oxide thereof wherein:
- $R^{1a}$ is hydrogen, chloro or fluoro and $R^{1b}$ is hydrogen;
- $R^2$ is hydrogen;
- A is a group (ia) in which n is 1 and $R^3$ is hydrogen or hydroxy;
- U is $CH_2$; and
- $R^5$ is an aromatic heterocyclic ring (B) having 8-11 ring atoms 2-4 of which ring atoms are heteroatoms, at least one of which is N or $NR^{13}$; wherein $Y^2$ contains 2-3 heteroatoms, one of which is S and 1-2 are N, with one N bonded to $X^3$, or the heterocyclic ring (B) has ring (a) aromatic selected from optionally substituted benzo and pyrido and pyridazino and ring (b) non aromatic and $Y^2$ has 3-5 atoms at least one of which is a heteroatom, with O, S, $C_2$ or $NR^{13}$ bonded to $X^5$ where $R^{13}$ is other than hydrogen, and either NHCO bonded via N to $X^3$, or O, S, $CH_2$ or NH bonded to $X^3$.

13. A compound according to claim 12 or a pharmaceutically acceptable salt thereof or N-oxide thereof wherein $R^5$ is selected from the group consisting of:
- 3-oxo-3,4-dihydro-2H-pyrido[3,2-b][1,4]oxazin-6-yl;
- 3-oxo-3,4-dihydro-2H-pyrido[3,2-b][1,4]thiazin-6-yl;
- 2,3-dihydro-[1,4]dioxino[2,3-c]pyridin-7-yl;
- [1,3]oxathiolo[5,4-c]pyridin-6-yl;
- 3,4-dihydro-2H-pyrano[2,3-c]pyridine-6-yl;
- [1,2,3]thiadiazolo[5,4-b]pyridin-6-yl;
- 2,3-dihydro-1,4-benzodioxin-5-carbonitro-7-yl;
- 8-fluoro-2,3-dihydro-1,4-benzodioxin-6-yl;
- 3-oxo-3,4-dihydro-2H-benzo[1,4]thiazin-6-yl; and
- 2,3-dihydro[1,4)oxathiino[2,3-c]pyridin-7-yl.

14. A compound of formula (I) according to claim 1 or a pharmaceutically acceptable salt thereof or N-oxide thereof wherein $R^5$ is selected from the group consisting of:
- [1,2,3]thiadiazolo[5,4-b]pyridin-6-yl;
- 1H-pyrrolo[2,3-b]pyridin-2-yl;
- 2,3-dihydro-[1,4]dioxino[2,3-b]pyridin-6-yl;
- 2,3-dihydro-[1,4]dioxino[2,3-b]pyridin-7-yl;
- 2,3-dihydro-[1,4]dioxino[2,3-c]pyridin-7-yl;
- 2,3-dihydro-benzo[1,4]dioxin-6-yl;
- 2-oxo-2,3-dihydro-1H-pyrido[2,3-b][1,4)oxazin-7-yl;
- 2-oxo-2,3-dihydro-1H-pyrido[2,3-b][1,4]thiazin-7-yl;
- 3,4-dihydro-2H-benzo[1,4]oxazin-6-yl;
- 3-methyl-2-oxo-2,3-dihydro-benzooxazol-6-yl;
- 3-oxo-3,4-dihydro-2H-benzo[1,4]oxazin-6-yl;
- 3-oxo-3,4-dihydro-2H-pyrido[3,2-b][1,4]oxazin-6-yl;
- 3-oxo-3,4-dihydro-2H-benzo[1,4]thiazin-6-yl (4H-benzo[1,4]thiazin-3-one-6-yl);
- 4-oxo-4H-pyrido[1,2-a]pyrimidin-2-yl;
- 6-nitro-benzo[1,3]dioxol-5-yl;
- 7-fluoro-3-oxo-3,4-dihydro-2H-benzo[1,4]oxazin-6-yl;
- 8-hydroxy-1-oxo-1,2-dihydro-isoquinolin-3-yl;
- 8-hydroxyquinolin-2-yl;
- benzo[1,2,3]thiadiazol-5-yl;
- benzo[1,2,5]thiadiazol-5-yl;
- benzothiazol-5-yl;
- thiazolo-[5,4-b]pyridin-6-yl;
- 3-oxo-3,4-dihydro-2H-pyrido[3,2-b][1,4]thiazin-6-yl;
- 7-chloro-3-oxo-3,4-dihydro-2H-pyrido[3,2-b][1,4]thiazin-6-yl;
- 7-fluoro-3-oxo-3,4-dihydro-2H-pyrido(3,2-b][1,4]thiazin-6-yl;
- 2-oxo-2,3-dihydro-1H-pyrido[3,4-b][1,4]thiazin-7-yl;
- [1,3]oxathiolo[5,4-c]pyridin-6-yl;
- 3,4-dihydro-2H-pyrano[2,3-c]pyridine-6-yl;
- 2,3-dihydro-1,4-benzodioxin-5-carbonitro-7-yl;
- 2,3-dihydro[1,4]oxathiino[2,3-c]pyridin-7-yl;
- 2,3-dihydrofuro[2,3-c]pyridin-5-yl;
- 5-fluoro-2,3-dihydro-1,4-benzodioxino-7-yl;
- 2,3-dihydro-1-benzofuran-5-yl;
- 6,7-dihydro-5H-thieno[3,2-b]pyran-2-yl;
- 6-oxo-6,7-dihydro-5H-pyridazino[3,4-b)[1,4]thiazin-3-yl;
- 5-oxo-1,2,3,5-tetrahydro-7-indolizinyl;
- 2-methyl-1-oxo-1,2,3,4-tetrahydro-7-isoquinolinyl;
- 8-fluoro-2,3-dihydro-1,4-benzodioxin-6-yl;
- 2,3-dihydro-1-benzofuran-7-carbonitrile;
- 5,6-dihydro-4H-cyclopenta[b]thien-2-yl; and
- 6,7-dihydro-5H-thieno[3,2-b]pyran-2-yl.

15. (4R)-4-({4-[(2,3-dihydro[1,4]dioxino[2,3-c]pyridin-7-ylmethyl)amino]-1-piperidinyl}methyl)-3-fluoro-4,5-dihydro-7H-pyrrolo[3,2,1-de]-1,5-naphthyridin-7-one or a pharmaceutically acceptable salt thereof.

* * * * *